US008148577B2

(12) United States Patent
Woster et al.

(10) Patent No.: US 8,148,577 B2
(45) Date of Patent: Apr. 3, 2012

(54) POLYAMINES USEFUL AS ANTI-PARASITIC AND ANTI-CANCER THERAPEUTICS AND AS LYSINE-SPECIFIC DEMETHYLASE INHIBITORS

(75) Inventors: Patrick M. Woster, Canton, MI (US); Tracey Boncher, Rockford, MI (US); Robert A. Casero, Glen Arm, MD (US)

(73) Assignees: The Johns Hopkins University, Baltimore, MD (US); Wayne State University, Detroit, MI (US)

( * ) Notice: Subject to any disclaimer, the term of this patent is extended or adjusted under 35 U.S.C. 154(b) by 0 days.

(21) Appl. No.: 12/763,722

(22) Filed: Apr. 20, 2010

(65) Prior Publication Data

US 2010/0273745 A1 Oct. 28, 2010

Related U.S. Application Data

(62) Division of application No. 11/463,840, filed on Aug. 10, 2006, now abandoned.

(60) Provisional application No. 60/707,420, filed on Aug. 10, 2005.

(51) Int. Cl.
*C07C 279/12* (2006.01)
*C07C 279/18* (2006.01)
*A61K 31/155* (2006.01)

(52) U.S. Cl. ........ 564/235; 564/236; 564/237; 514/634; 514/635

(58) Field of Classification Search .................. None
See application file for complete search history.

(56) References Cited

U.S. PATENT DOCUMENTS

| 4,252,951 A * | 2/1981 | Jackson et al. ............... 540/220 |
| 5,541,230 A | 7/1996 | Basu et al. |
| 5,656,671 A | 8/1997 | Bergeron, Jr. |
| 5,681,837 A | 10/1997 | Bergeron |
| 5,753,714 A | 5/1998 | Stemerick et al. |
| 5,889,061 A | 3/1999 | Frydman et al. |
| 7,001,925 B1 | 2/2006 | Phanstiel |
| 2005/0027016 A1 | 2/2005 | Fahl et al. |

FOREIGN PATENT DOCUMENTS

| WO | WO-98/17624 A1 | 4/1998 |
| WO | WO-00/66587 A2 | 11/2000 |
| WO | WO-02/10142 A1 | 2/2002 |
| WO | WO-03050072 A1 | 6/2003 |
| WO | WO-2006071608 A2 | 7/2006 |

OTHER PUBLICATIONS

Braga et al., Chem. Commun. (2005), 29, p. 3635-3645.*
Database CAPLUS on STN, Acc. No. 2004:1013391, Zahariev et al., Tetrahedron Letters (2004), 45(51), p. 9423-9426 (abstract).*
N. Seiler et al., "Pharmacological aspects of cytotoxic polyamine analogs and derivatives for cancer therapy", Pharmacology & Therapeutics, 107(1), pp. 99-119 (2005).
V.K. Reddy et al., "Conformationally Restricted Analogues of 1N,12N-Bisethylsperimine: Synthesis and Growth Inhibitory Effects on Human Tumor Cell Lines", J. Med. Chem., 41(24), pp. 4723-4732 (1998).
S.M. Oredsson et al., "Polyaminies, The Elusive Cancer Markers", Clinics in Laboratory Medicine, 2(3), pp. 507-518 (1982).
B. Frydman et al., "Polyamine-based Chemotheraphy of Cancer", Expert Opinion on Therapeutic Patents, vol. 9, pp. 1055-1068 (1999).
A.M. Dance et al., "Synthesis and biological activities of bisnaphthalimido polyamines derivatives: cytotoxicity, DNA binding, DNA damage and drug localization in breast cancer MCF 7 cells", Biochemical Pharmacology, 69(1), pp. 19-27 (2005).
R.A. Casero, Jr. et al., "Terminally Alkylated Polyamine Analogues as Chemotherapeutic Agents", Journal of Medicinal Chemistry, 44(1), pp. 1-26 (2001).
A. Valasinas et al., "Conformationally Restricted Analogues of 1N,14N-Bisethylhomospermine (BE-4-4-4): Synthesis and Growth Inhibitory Effects on Human Prostate Cancer Cells", J. Med. Chem., 44(3), pp. 390-403 (2001).
C. Dardonville et al., "Bisguanidine, Bis(2-aminoimidazoline), and Polyamine Derivatives as Potent and Selective Chemotherapeutic Agents against Trypanosoma brucei rhodesiense. Synthesis and In Vitro Evaluation", J. Med. Chem., vol. 47, pp. 2296-2307 (2004).
D. Braga et al., "Making crystals from crystals: a green route to crystal engineering and polymorphism", Chem. Commun., vol. 29, pp. 3635-3645 (2005).
Database CAPLUS on STN, Acc. No. 1953:39584, GB 685019 (Dec. 31, 1952) (abstract).
Database CAPLUS on STN, Acc. No. 1985:533893, Clay et al., Inorganic Chemistry, 24(21), pp. 3330-3336 (abstract) (1985).
Casero, et al., "Significance of targeting polyamine metabolism as an antineoplastic strategy: unique targets for polyamine analogues." *Proc West Pharmacol Soc.* 2005;48:24-30.
Lee, et al., "Histone H3 Lysine 4 Demethylation Is a Target of Nonselective Antidepressive Medications." *Chemistry & Biology.* 13, 563-567, Jun. 2006.
Shi, et al., "Histone demethylation mediated by the nuclear amine oxidase homolog LSD1." *Cell*, Dec. 29, 2004;119(7):941-53.
Tomomatsu, et al., "Antitumor activities of polyguanidino compounds: screeing test and biological and biochemical activities."*Acta Medica Univeritatis Kagoshimaensis*, vol. 17, No. 2 (1975).
Wang and Casero, "Mammalian polyamine catabolism: a therapeutic target, a pathological problem, or both?" *J. Biochem.* 139, 17-25 (2006).

* cited by examiner

*Primary Examiner* — Brian J Davis
(74) *Attorney, Agent, or Firm* — Edwards Wildman Palmer LLP; Peter F. Corless; Melissa Hunter-Ensor, Esq.

(57) ABSTRACT

Polyamine, polyamine/guanidino, and polyamine/biguanide compounds are disclosed. The compounds are useful as anti-cancer and anti-parasitic treatments. The compounds are also useful as inhibitors of the enzyme lysine-specific demethylase-1.

12 Claims, 33 Drawing Sheets

FIG. 11
39-TDW-3
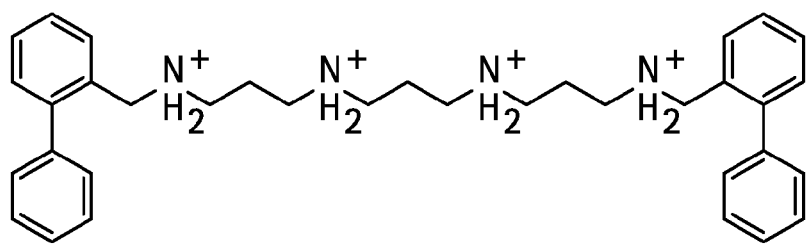
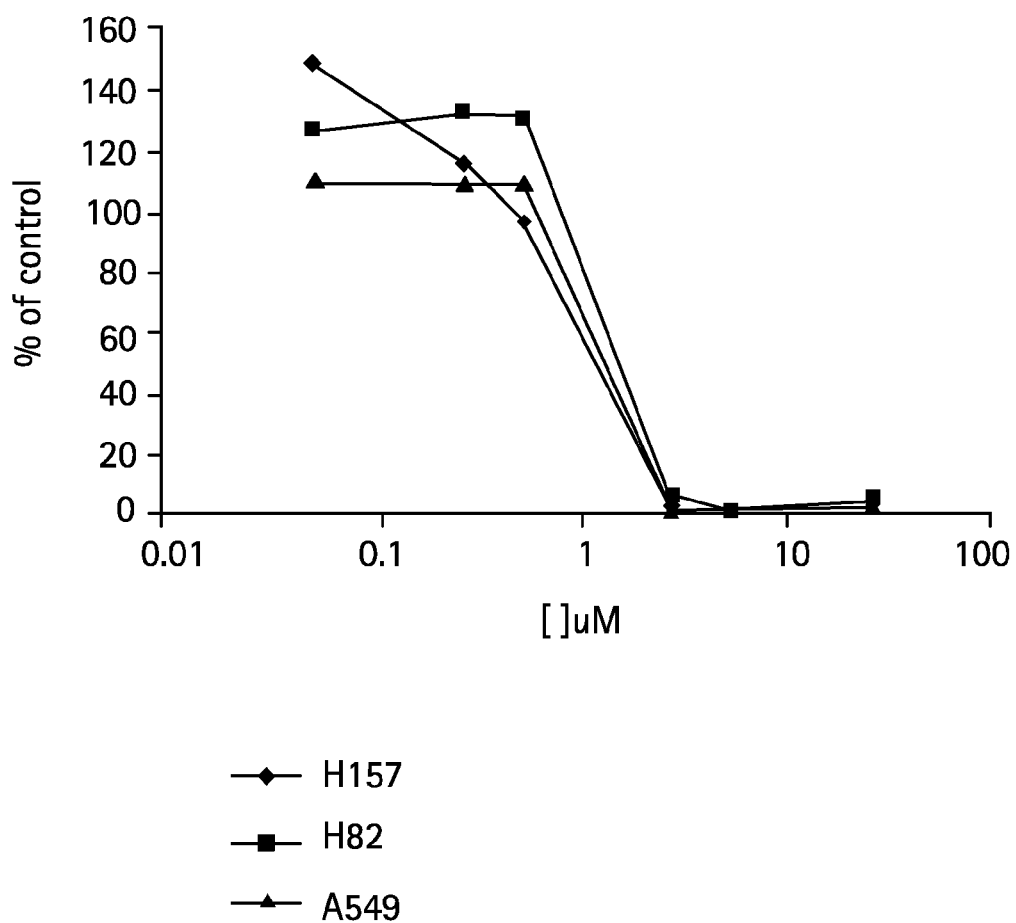
- ♦ H157
- ■ H82
- ▲ A549

FIG. 14
TDWs 96hr-H157
39-TDW-47c
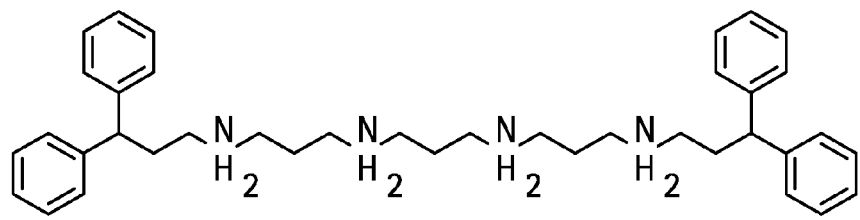
39-TDW-43
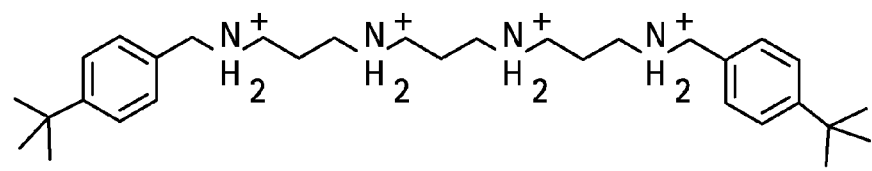
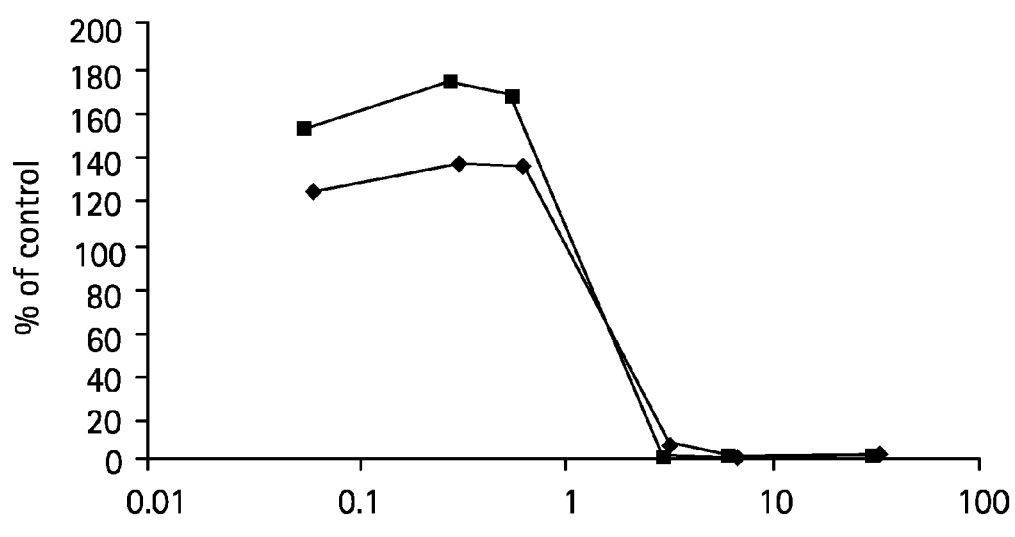

Effects of XB1-54-13B on tumor cell growth

| XB1-54-13B | Vmax (umol/mg protein/min) | Km (uM) |
| --- | --- | --- |
| 0 | 279 | 0.125 |
| 0.1 | 212 | 0.11 |
| 0.25 | 105 | 0.11 |
| 0.5 | 54.3 | 0.107 |
| 1 | 26.5 | 0.131 |

FIG. 33
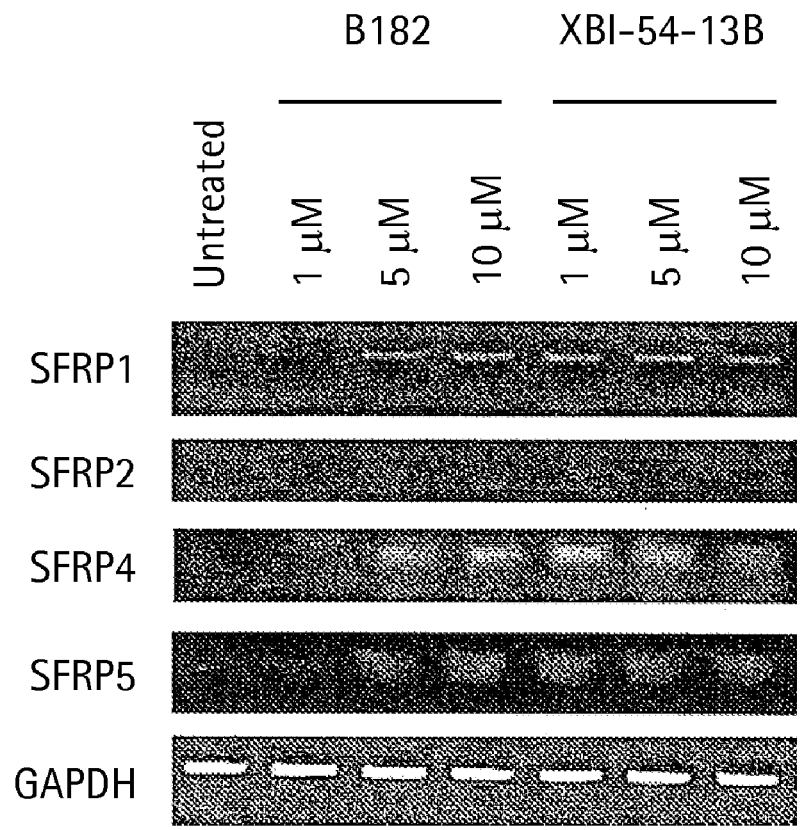
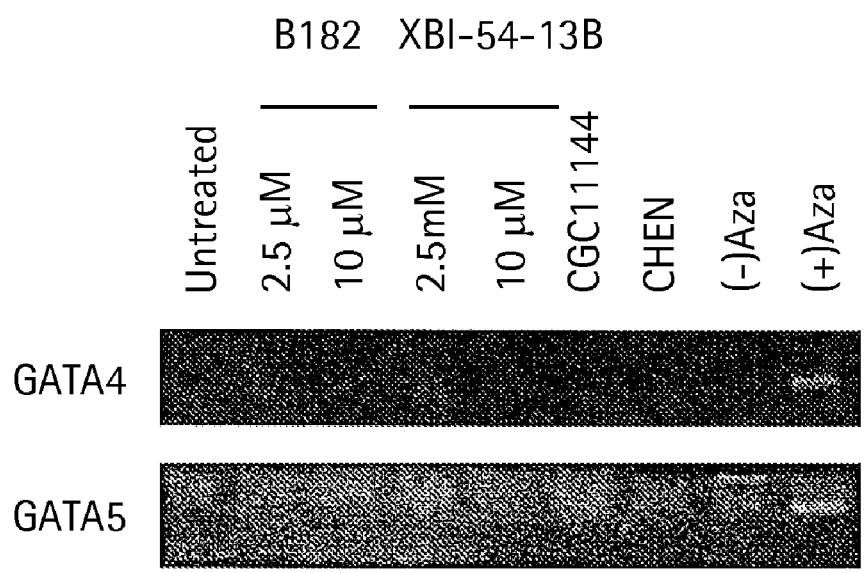

POLYAMINES USEFUL AS ANTI-PARASITIC AND ANTI-CANCER THERAPEUTICS AND AS LYSINE-SPECIFIC DEMETHYLASE INHIBITORS

CROSS REFERENCE TO RELATED APPLICATIONS

This application claims priority benefit of U.S. Provisional Patent Application No. 60/707,420, filed Aug. 10, 2005. The entire contents of that application are hereby incorporated by reference herein.

TECHNICAL FIELD

This invention pertains to polyamine compounds, including polyamine/guanidine and polyamine/biguanide compounds, useful for treatment of cancer and/or parasitic infections, and for inhibition of lysine-specific demethylase.

BACKGROUND

Polyamines are found in both eukaryotic and prokaryotic cells and figure prominently in regulation of the cell cycle and cell division. Agents specifically targeting polyamine biosynthesis, such as polyamine analogs, have been shown to have therapeutic effect in treatment of cancer, parasitic diseases, and other indications. These antiproliferatvie effects have been demonstrated to be, in part, a result of agent-induced decreases in the natural intracellular polyamines resulting from inhibition, down-regulation of polyamine biosynthesis and/or up regulation of polyamine catabolism. See, e.g., Wang and Casero, J, Biochem. 139:17 (2006); Casero et al., Proc. West. Pharmacol. Soc. 48:24 (2005); Casero et al., J. Med. Chem. 44:1 (2001); U.S. Pat. Nos. 5,889,061, 6,392,098, and 6,794,545; U.S. Patent Application Publication Nos. 2003/0072715, 2003/0195377, and International Patent Applications WO 98/17624, WO 00/66587, WO 02/10142, and WO 03/050072. Bi et al., Bioorgan. Med. Chem. Letters 16:3229 (2006) discuss novel alkylpolyaminoguanidines and alkylpolyaminobiguanides with potent antitrypanosomal activity.

The enzyme lysine-specific demethylase-1 (LSD1) has been shown to play an important role in regulation of gene expression; see Shi et al., Cell 119:941 (2004). WO 2006/071608 discusses certain methods involving lysine-specific demethylase-1. In view of the importance of gene regulation in areas such as cancer therapy and cancer prophylaxis, inhibitors of LSD1 are of great interest in the treatment and prevention of cancer and uncontrolled cell growth.

DISCLOSURE OF THE INVENTION

The invention embraces polyamine, polyamine/guanidine, and polyamine/biguanide compounds, and uses of those compounds for treatment and prevention of cancer. The invention also embraces uses of those compounds for inhibition of lysine-specific demethylase-1, and treatment of diseases involving lysine-specific demethylase-1.

In one embodiment, the invention embraces compounds of the formula (M):

where each E is independently selected from hydrogen, $C_1$-$C_8$ substituted or unsubstituted alkyl, $C_4$-$C_{15}$ substituted or unsubstituted cycloalkyl, $C_3$-$C_{15}$ substituted or unsubstituted branched alkyl, $C_6$-$C_{20}$ substituted or unsubstituted aryl or heteroaryl, $C_7$-$C_{24}$ substituted or unsubstituted aralkyl or heteroalkyl or heteroaralkyl, $C_3$-$C_{24}$ substituted or unsubstituted heteroaryl; each A is independently a $C_1$-$C_8$ n-alkyl; B is independently selected from $C_1$-$C_{12}$ n-alkyl or $C_3$-$C_8$ cycloalkyl; and each X is independently selected from —NH—, —NH—C(=NH)—NH—, and —NH—C(=NH)—NH—C(=NH)—NH—; and all salts, solvates, hydrates, and stereoisomers thereof.

In another embodiment, B is independently selected from $C_1$-$C_8$ n-alkyl.

In another embodiment, at least one X is selected from —NH—C(=NH)—NH— and —NH—C(=NH)—NH—C(=NH)—NH—. In another embodiment, at least one X is —NH—C(=NH)—NH—. In another embodiment, at least one X is —NH—C(=NH)—NH—C(=NH)—NH—. In another embodiment, each X is independently selected from —NH—C(=NH)—NH— and —NH—C(=NH)—NH—C(=NH)—NH—. In another embodiment, both X groups are —NH—C(=NH)—NH—. In another embodiment, both X groups are —NH—C(=NH)—NH—C(=NH)—NH—. In another embodiment, one X is —NH—C(=NH)—NH— and another X is —NH—C(=NH)—NH—C(=NH)—NH—.

In one embodiment, the invention embraces polyamine/guanidine or N-alkylated polyamine/guanidine compounds, such as a polyaminobisguanidine or polyaminobiguanide or N-alkylated variation thereof. An N-alkylated polyaminoguanidine intends a polyaminoguanidine wherein the imine nitrogen of the guanidine is alkylated, such as in a 2-methylguanadine derivative. In one embodiment, each A is —(CH$_2$)$_3$— and B is —(CH$_2$)$_4$—. In another embodiment, each A is —(CH$_2$)$_3$— and B is —(CH$_2$)$_7$—.

In one embodiment, the compound is a polyaminoguanidine of the formula (I):

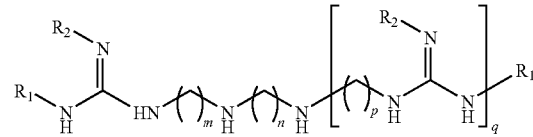

or a salt, solvate, or hydrate thereof, wherein n is an integer from 1 to 12, m and p are independently an integer from 1 to 5, q is 0 or 1, each $R_1$ is independently selected from the group consisting of $C_1$-$C_8$ substituted or unsubstituted alkyl, $C_4$-$C_{15}$ substituted or unsubstituted cycloalkyl, $C_3$-$C_{15}$ substituted or unsubstituted branched alkyl, $C_6$-$C_{20}$ substituted or unsubstituted aryl, $C_6$-$C_{20}$ substituted or unsubstituted heteroaryl, $C_7$-$C_{24}$ substituted or unsubstituted aralkyl, and $C_7$-$C_{24}$ substituted or unsubstituted heteroaralkyl, and each $R_2$ is independently selected from hydrogen or a $C_1$-$C_8$ substituted or unsubstituted alkyl.

In one embodiment, the compound is of the formula (I) wherein at least one or both $R_1$ is a $C_6$-$C_{20}$ substituted or unsubstituted aryl, such as a single ring substituted or unsubstituted aryl, including without limitation, substituted or unsubstituted phenyl. In one embodiment, the compound is of the formula (I) and each $R_1$ is phenyl. In one embodiment, q is 1, m and p are 3, and n is 4. In another embodiment, q is 1, m and p are 3, and n is 7.

In one embodiment, the compound is of the formula (I) wherein at least one or both $R_1$ is a $C_8$-$C_{12}$ or a $C_1$-$C_8$ substituted or unsubstituted alkyl, such as a linear alkyl. One or both $R_1$ may be a $C_1$-$C_8$ substituted or unsubstituted linear alkyl, such as methyl or ethyl. In one embodiment, each $R_1$ is methyl. Each or both $R_1$ may comprise or be a $C_4$-$C_{15}$ cycloalkyl group, such as a cycloalkyl group containing a linear alkyl group, where the cycloalkyl group is connected to the molecule either via its alkyl or cycloalkyl moiety. For instance, each or both $R_1$ may be cyclopropylmethyl or cyclohexylmethyl. In one embodiment, one $R_1$ is cyclopropylmethyl or cyclohexylmethyl and the other $R_1$ is a linear alkyl group, such as a linear $C_1$-$C_8$ unsubstituted alkyl group, including without limitation an ethyl group. In one embodiment, $R_1$ is a $C_3$-$C_{15}$ branched alkyl group such as isopropyl. When $R_1$ is a $C_1$-$C_8$ substituted alkyl, the substituted alkyl may be substituted with any substituent, including a primary, secondary, tertiary or quaternary amine. Accordingly, in one embodiment, $R_1$ is a $C_1$-$C_8$ alkyl group substituted with an amine such that $R_1$ may be e.g., alkyl-$NH_2$ or an alkyl-amine-alkyl moiety such as —$(CH_2)_yNH(CH_2)zCH_3$ where y and z are independently an integer from 1 to 8. In one embodiment, $R_1$ is —$(CH_2)_3NH_2$.

$C_1$-$C_8$ substituted or unsubstituted alkyl. In one embodiment, each $R_2$ is an unsubstituted alkyl such as methyl. In another embodiment, each $R_2$ is hydrogen.

Any of the compounds of formula (I) listed above may be compounds where q is 1 and m and p are the same. Accordingly, the polyaminoguanidines of formula (I) may be symmetric with reference to the polyaminoguanidine core (e.g., excluding $R_1$). Alternatively, the compounds of formula (I) may be asymmetric, e.g., when q is 0. In one embodiment, m and p are 1. In one embodiment, q is 0. In one embodiment, n is an integer from 1 to 5.

It is understood and clearly conveyed by this disclosure that each $R_1$, $R_2$, m, n, p and q disclosed in reference to formula (I) intends and includes all combinations thereof the same as if each and every combination of $R_1$, $R_2$, m, n, p and q were specifically and individually listed.

Representative compounds of the formula (I) include, e.g.:

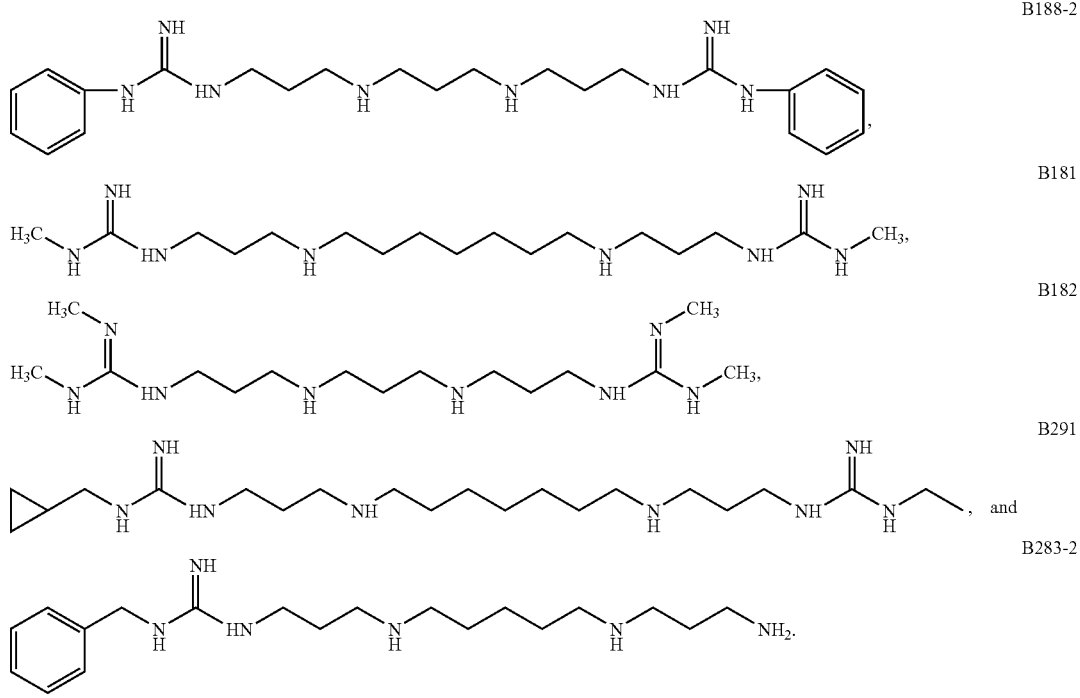

In one embodiment, the compound is of the formula (I) where at least one $R_1$ is a $C_7$-$C_{24}$ substituted or unsubstituted aralkyl, which in one embodiment is an aralkyl connected to the molecule via its alkyl moiety (e.g., benzyl). In one embodiment, each $R_1$ is an aralkyl moiety wherein the alkyl portion of the moiety is substituted with two aryl groups and the moiety is connected to the molecule via its alkyl group. For instance, in one embodiment at least one or both $R_1$ is a $C_7$-$C_{24}$ aralkyl wherein the alkyl portion is substituted with two phenyl groups, such as when $R_1$ is 2,2-diphenylethyl or 2,2-dibenzylethyl. In one embodiment, each $R_1$ of formula (I) is 2,2-diphenylethyl and n is 1, 2 or 5. In one embodiment, each $R_1$ of formula (I) is 2,2-diphenylethyl, n is 1, 2 or 5 and m and p are each 1.

In one embodiment, at least one $R_1$ is hydrogen. When at least one $R_1$ is hydrogen, the other $R_1$ may be any moiety listed above for $R_1$, including an aryl group such as benzyl.

Any of the compounds of formula (I) listed above include compounds where at least one or both of $R_2$ is hydrogen or a In one embodiment, the compound is a polyaminobiguanide or N-alkylated polyaminobiguanide. An N-alkylated polyaminobiguanide intends a polyaminobiguanide wherein at least one imine nitrogen of at least one biguanide is alkylated. In one embodiment, the compound is a polyaminobiguanide of the formula (II):

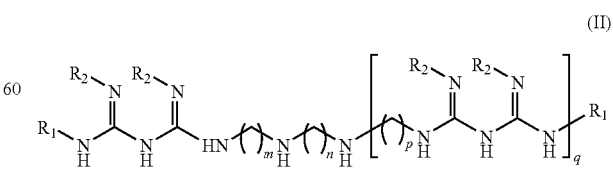

or a salt, solvate, or hydrate thereof, wherein n is an integer from 1 to 12, m and p are independently an integer from 1 to 5, q is 0 or 1, each $R_1$ is independently selected from the group consisting of $C_1$-$C_8$ substituted or unsubstituted alkyl, $C_6$-$C_{20}$ substituted or unsubstituted aryl, $C_6$-$C_{20}$ substitute or unsubstituted heteroaryl, $C_7$-$C_{24}$ substituted or unsubstituted aralkyl, and $C_7$-$C_{24}$ substituted or unsubstituted heteroaralkyl and each $R_2$ is independently hydrogen or a $C_1$-$C_8$ substituted or unsubstituted alkyl.

In one embodiment, at least one or each $R_1$ is a $C_1$-$C_8$ substituted or unsubstituted alkyl, such as those listed above in reference to formula (I). For instance, when $R_1$ is a $C_1$-$C_8$ substituted alkyl, the substituted alkyl may be substituted with any substituent, including a primary, secondary, tertiary or quaternary amine. Accordingly, in one embodiment, $R_1$ is a $C_1$-$C_8$ alkyl group substituted with an amine such that $R_1$ may be e.g., alkyl-$NH_2$ or an alkyl-amine-alkyl moiety such as $-(CH_2)_y NH(CH_2)z CH_3$ where y and z are independently an integer from 1 to 8. In one embodiment, $R_1$ is $-(CH_2)_3 NH_2$. $R_1$ may also be a $C_4$-$C_{15}$ substituted or unsubstituted cycloalkyl or a $C_3$-$C_{15}$ substituted or unsubstituted branched alkyl, such as described for formula (I) above. In one embodiment, at least one or each $R_1$ is a $C_6$-$C_{20}$ substituted or unsubstituted aryl, such as those listed above in reference to formula (I). In one embodiment, q is 1, m and p are 3, and n is 4. In another embodiment, q is 1, m and p are 3, and n is 7.

In one embodiment, the compound is of the formula (II) where at least one or both $R_1$ is a $C_7$-$C_{24}$ substituted or unsubstituted aralkyl, which in one embodiment is an aralkyl connected to the molecule via its alkyl moiety. In one embodiment, each $R_1$ is an aralkyl moiety wherein the alkyl portion of the moiety is substituted with one or two aryl groups and the moiety is connected to the molecule via its alkyl moiety. For instance, in one embodiment at least one or both $R_1$ is an aralkyl wherein the alkyl portion is substituted with two phenyl or benzyl groups, such as when $R_1$ is 2,2-diphenylethyl or 2,2-dibenzylethyl. In one embodiment, each $R_1$ of formula (II) is 2,2-diphenylethyl and n is 1, 2 or 5. In one embodiment, each $R_1$ of formula (II) is 2,2-diphenylethyl and n is 1, 2 or 5 and m and p are each 1.

Any of the compounds of formula (II) listed above include compounds where at least one or both of $R_2$ is hydrogen or a $C_1$-$C_8$ substituted or unsubstituted alkyl. In one embodiment, each $R_2$ is an unsubstituted alkyl, such as methyl. In another embodiment, each $R_2$ is a hydrogen.

Any of the compounds of formula (II) listed above include compounds where q is 1 and m and p are the same. Accordingly, the polyaminobiguanides of formula (II) may be symmetric with reference to the polyaminobiguanide core (e.g., excluding $R_1$). Alternatively, the compounds of formula (II) may be asymmetric, e.g., when q is 0. In one embodiment, m and p are 1. In one embodiment, q is 0. In one embodiment, n is an integer from 1 to 5. In one embodiment, q, m and p are each 1 and n is 1, 2 or 5.

It is understood and clearly conveyed by this disclosure that each $R_1$, $R_2$, m, n, p and q disclosed in reference to formula (II) intends and includes all combinations thereof the same as if each and every combination of $R_1$, $R_2$, m, n, p and q were specifically and individually listed.

Representative compounds of the formula (II) include, e.g.:

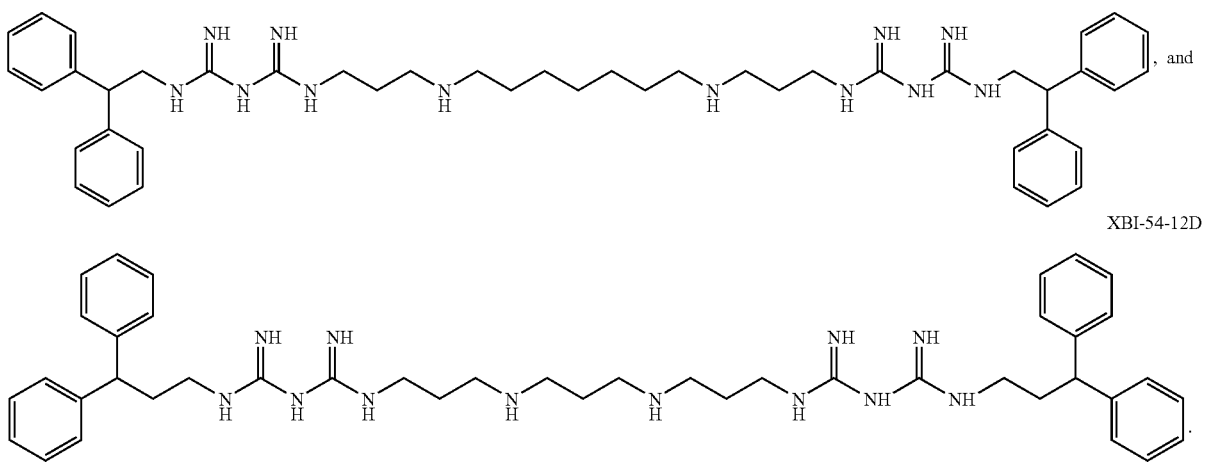

In one embodiment, the compound is a polyamine. In one embodiment, the polyamine is of the formula (III):

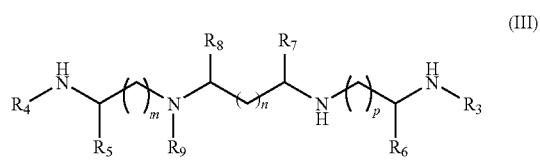

or a salt, solvate, or hydrate thereof, wherein n is an integer from 1 to 12; m and p are independently an integer from 1 to 5; $R_3$ and $R_4$ are independently selected from the group consisting of hydrogen, $C_1$-$C_8$ substituted or unsubstituted alkyl, $C_5$-$C_{20}$ substituted or unsubstituted aryl and $C_7$-$C_{24}$ substituted or unsubstituted aralkyl; $R_5$, $R_9$, $R_6$, $R_7$ and $R_8$ are independently selected from the group consisting of hydrogen and $C_1$-$C_8$ substituted or unsubstituted alkyl; and wherein either m and p are not the same integer or at least one of $R_5$, $R_9$, $R_6$, $R_7$ and $R_8$ is a $C_1$-$C_8$ substituted or unsubstituted alkyl.

In one embodiment, $R_9$ is a $C_1$-$C_8$ substituted or unsubstituted alkyl. When $R_9$ is a $C_1$-$C_8$ substituted alkyl, the substituted alkyl may be substituted with any substituent, including a primary, secondary, tertiary or quaternary amine. Accordingly, in one embodiment, $R_9$ is a $C_1$-$C_8$ alkyl group substituted with an amine such that $R_9$ may be e.g., alkyl-$NH_2$ or an alkyl-amine-alkyl moiety such as $-(CH_2)_y NH(CH_2)z CH_3$ where y and z are independently an integer from 1 to 8. In one embodiment, $R_9$ is —$(CH_2)_3NHCH_2CH_3$.

In one embodiment, one or both of $R_3$ and $R_4$ is hydrogen. If only one of $R_3$ and $R_4$ is hydrogen, the $R_3$ or $R_4$ that is not hydrogen may be any moiety described herein, such as a $C_1$-$C_8$ substituted or unsubstituted alkyl group, including a cyclic alkyl group such as cyclopropylmethyl or cycloheptylmethyl.

In one embodiment, one or both of $R_3$ and $R_4$ is a $C_1$-$C_8$ substituted or unsubstituted alkyl, including without limitation a substituted or unsubstituted n-alkyl (such as n-pentyl), substituted or unsubstituted branched ($C_3$-$C_8$) alkyl (such as 2-methylbutyl) or substituted or unsubstituted ($C_3$-$C_8$) cycloalkyl (such as cyclohexylmethyl). Larger chain alkyl (linear, branched and cyclic) are also considered, such as a $C_9$-$C_{15}$ substituted or unsubstituted alkyl. Where one or both of $R_3$ and $R_4$ is a $C_1$-$C_8$ substituted or unsubstituted n-alkyl, the moiety may be any n-alkyl, such as methyl or ethyl. In one embodiment, both $R_3$ and $R_4$ are a $C_1$-$C_8$ substituted or unsubstituted alkyl, wherein one of $R_3$ and $R_4$ is an n-alkyl moiety and the other is a cyclic moiety, which is understood to contain at least three carbon atoms. Alternatively, both $R_3$ and $R_4$ may be a $C_1$-$C_8$ substituted or unsubstituted n-alkyl. When one or both of $R_3$ and $R_4$ is a substituted alkyl, whether linear, branched or cyclic, the alkyl may be substituted with one or more substituents such as those listed under "Substituted alkyl" and includes alkyl substituted with any halogen, such as a monohaloalkyl, dihaloalkyl, trihaloalkyl or multihaloalkyl, including a perhalooalkyl, for example, perfluoroalkyl and percholoralkyl, such as trifluoromethyl or pentachloroethyl.

In one embodiment, one or both of $R_3$ and $R_4$ is a $C_6$-$C_{20}$ substituted or unsubstituted aryl. In one embodiment, one or both of $R_3$ and $R_4$ is a $C_6$-$C_{20}$ substituted aryl, which aryl groups may be substituted with one or more substituents such as those listed under "Substituted aryl." In one embodiment, one or both of $R_3$ and $R_4$ is a $C_6$-$C_{20}$ substituted aryl, which aryl groups may be substituted with one or more alkyoxy (such as —$OCH_3$), alkyl (including a branched alkyl such as tert-butyl), or halo groups (such as fluoro). In one embodiment, one or both of $R_3$ and $R_4$ is a halo-substituted aryl or a halo-substituted aralkyl, such as 2,4,5-trifluorophenyl or 2,4,5-trifluorobenzyl. In one embodiment, one or both of $R_3$ and $R_4$ is a di-alkyl-monoalkoxy-substituted aryl or aralkyl, such as 4,5-di-tert-butyl-2-methoxybenzyl or 4,5-di-tert-butyl-2-methoxyphenyl.

In one embodiment, one or both of $R_3$ and $R_4$ is a $C_7$-$C_{24}$ substituted or unsubstituted aralkyl or heteroaralkyl such as an aralkyl or heteroaralkyl connected to the molecule via its alkyl moiety. In one embodiment, one or both of $R_3$ and $R_4$ is a substituted aralkyl or heteroaralkyl connected to the molecule via its alkyl moiety. A substituted aralkyl may be substituted with one or more substituents such as those listed under "Substituted aralkyl" and a substituted heteroaralkyl may be substituted with one or more substituents such as those listed under "Substituted heteroaralkyl." In one embodiment, one or both of $R_3$ and $R_4$ is a substituted heteroaralkyl having at least one nitrogen atom. In one embodiment, one or both of $R_3$ and $R_4$ is a single ring heteroaralkyl having at least one nitrogen atom. In one embodiment, one or both of $R_3$ and $R_4$ is 1-(2-N-methylpyrrolyl)-methyl.

In one embodiment, at least 1 or at least 2 or at least 3 of $R_5$, $R_9$, $R_6$, $R_7$ and $R_8$ is a $C_1$-$C_8$ substituted or unsubstituted alkyl. $R_5$, $R_9$, $R_6$, $R_7$ and $R_8$ may be a $C_1$-$C_8$ substituted or unsubstituted alkyl. In one embodiment at least 1 or at least 2 or at least 3 of $R_5$, $R_9$, $R_6$, $R_7$ is a $C_1$-$C_8$ unsubstituted n-alkyl, such as methyl or ethyl. In one embodiment, both $R_6$ and $R_5$ are methyl or ethyl. In one embodiment, at least one $R_7$ and $R_8$ is methyl or ethyl. In one embodiment, $R_7$ is methyl.

It is understood and clearly conveyed by this disclosure that each $R_3$, $R_4$, $R_5$, $R_9$, $R_6$, $R_7$, $R_8$, m, n, y, z and p disclosed in reference to formula (III) intends and includes all combinations thereof the same as if each and every combination of $R_3$, $R_4$, $R_5$, $R_9$, $R_6$, $R_7$, $R_8$, m, n, y, z and p were specifically and individually listed.

Representative compounds of the formula (III) include, e.g.:

GEXH-32-50A

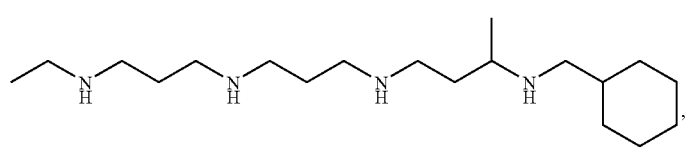

44-DHEJ-4C

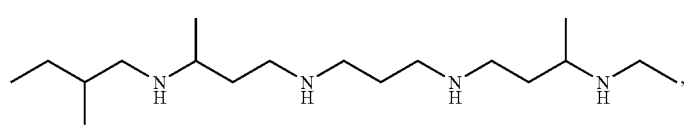

44-DHEJ-5C

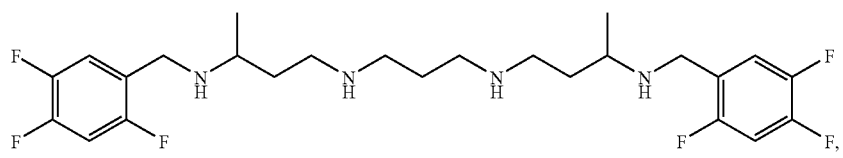

55-DHEJ-24C

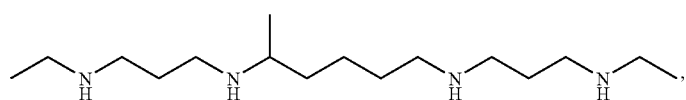

YZ33046

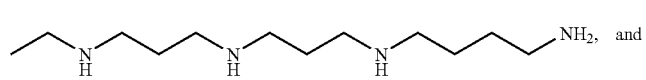

-continued

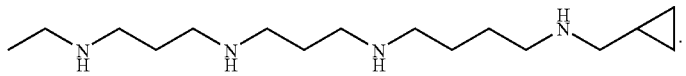

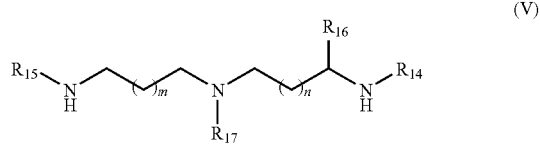

In one embodiment, the polyamine is of the formula (IV):

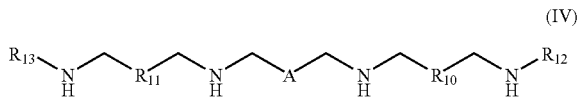

or a salt, solvate, or hydrate thereof, wherein A, $R_{10}$ and $R_{11}$ are independently $(CH_2)_n$ or ethene-1,1-diyl; n is an integer from 1 to 5; $R_{12}$ and $R_{13}$ are independently selected from the group consisting of hydrogen, $C_2$-$C_8$ substituted or unsubstituted alkenyl and $C_1$-$C_8$ substituted or unsubstituted alkyl;

propen-2-yl. In one embodiment, at least one or both of $R_{12}$ and $R_{13}$ is a $C_1$-$C_8$ substituted or unsubstituted alkyl, such as methyl or ethyl or any $C_1$-$C_8$ substituted or unsubstituted alkyl mentioned above in reference to any one of formulae (I), (II) or (III).

It is understood and clearly conveyed by this disclosure that each A, n, $R_{10}$, $R_{11}$, $R_{12}$ and $R_{13}$ disclosed in reference to formula (IV) intends and includes all combinations thereof the same as if each and every combination of A, n, $R_{10}$, $R_{11}$, $R_{12}$ and $R_{13}$ were specifically and individually listed.

Representative compounds of the formula (IV) include, e.g.:

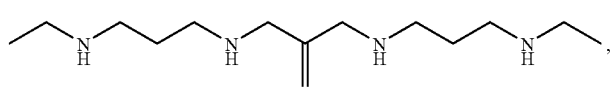
ZQW-44

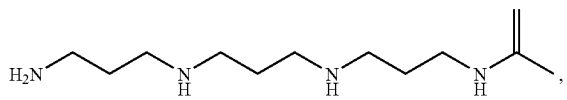
ZQW-35-7C

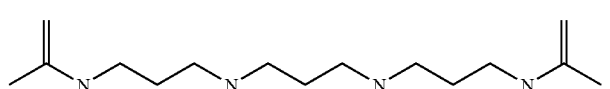
ZQW-35-8

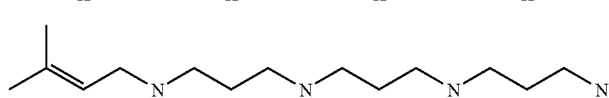
SV-53-18C2 , and

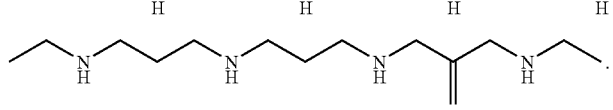
ZQW-46 and at least one of A, $R_{10}$, $R_{11}$, $R_{12}$ and $R_{13}$ comprises an alkenyl moiety. In another embodiment, when any one or more of A, $R_{10}$, and $R_{11}$ is alkenyl, the alkene portion branches off the direct chain connecting the nitrogen atoms; that is, no more than one $sp^2$-hybridized carbon occurs in the carbon nodes along the shortest path from one nitrogen flanking A, $R_{10}$, and/or $R_{11}$ to the other flanking nitrogen. For example, when A is ethene, the segment containing A is of the form —$CH_2C(\!\!=\!\!CH_2)$—$CH_2$— and the three nodes in the shortest carbon path between the nitrogens containing the A moiety has only one $sp^2$-hybridized carbon. When A is propene, the segment containing A can be of the form —$CH_2C$($=\!\!CHCH_3$)—$CH_2$— or —$CH_2C$(—$CH\!\!=\!\!CH_2$)—$CH_2$—.

In one embodiment, A is $(CH_2)_n$ and n is 1. In one embodiment, A is ethene-1,1-diyl. In one embodiment, A is $(CH_2)_n$ and one or both of $R_{12}$ and $R_{13}$ comprises an alkenyl moiety, such as propen-2-yl.

In one embodiment at least one or both of $R_{10}$ and $R_{11}$ is ethene-1,1-diyl. In one embodiment, both $R_{10}$ and $R_{11}$ are $(CH_2)_n$ such as $CH_2$ (where n=1).

In one embodiment, at least one or both of $R_{12}$ and $R_{13}$ is hydrogen. In one embodiment, at least one or both of $R_{12}$ and $R_{13}$ is a $C_2$-$C_8$ substituted or unsubstituted alkenyl, such as In one embodiment, the polyamine is of the formula (V):

$$R_{15}\!\!-\!\!\underset{H}{N}\!\!-\!\!(\phantom{x})_m\!\!-\!\!\underset{R_{17}}{\overset{R_{16}}{N}}\!\!-\!\!(\phantom{x})_n\!\!-\!\!\underset{H}{N}\!\!-\!\!R_{14} \quad (V)$$

or a salt, solvate, or hydrate thereof, wherein n is an integer from 1 to 8; m is an integer from 1 to 8; $R_{15}$ and $R_{14}$ are independently selected from the group consisting of hydrogen, $C_1$-$C_8$ substituted or unsubstituted n-alkyl or $(C_3$-$C_8)$ branched alkyl, $C_6$-$C_{20}$ substituted or unsubstituted aryl or heteroaryl and $C_7$-$C_{24}$ substituted or unsubstituted aralkyl or heteroaralkyl; $R_{16}$ and $R_{17}$ are independently hydrogen or a $C_1$-$C_8$ substituted or unsubstituted alkyl; and wherein the compound contains no more than three secondary amino groups except when $R_{17}$ is a $C_1$-$C_8$ substituted or unsubstituted alkyl and wherein the compound is free from a methylphosphonate or hydroxy moiety.

In one embodiment, at least one or both of $R_{15}$ and $R_{14}$ is hydrogen. When only one of $R_{15}$ and $R_{14}$ is hydrogen, the $R_{15}$ or $R_{14}$ that is not hydrogen may be any other moiety listed above, such as a $C_6$-$C_{20}$ substituted or unsubstituted aryl or heteroaryl (e.g.; 4-isopropylbenzyl, 2-phenylbenzyl, 3,3,-diphenylpropyl and the like or any $C_6$-$C_{20}$ substituted or any unsubstituted aryl or heteroaryl listed above in reference to any one of formulae (I)-(IV)).

In one embodiment, at least one or both of $R_{15}$ and $R_{14}$ is a $C_1$-$C_8$ substituted or unsubstituted n-alkyl or ($C_3$-$C_8$) branched alkyl, such as methyl, ethyl, 3-methyl-butyl, 2-ethyl-butyl, 5-$NH_2$-pent-1-yl, prop-1-yl-methyl(phenyl) phosphinate and the like or any $C_1$-$C_8$ substituted or unsubstituted n-alkyl or ($C_3$-$C_8$) branched alkyl listed above in reference to formulae (I)-(IV). In one embodiment, at least one or both of $R_{15}$ and $R_{14}$ is a $C_1$-$C_8$ substituted or unsubstituted n-alkyl, such as an n-alkyl substituted with a methyl (phenyl)phosphinate moiety or a $NH_2$-substituted n-alkyl. In one embodiment, both $R_{15}$ and $R_{14}$ are $C_1$-$C_8$ substituted or unsubstituted n-alkyl or ($C_3$-$C_8$) branched alkyl moieties, such as when $R_{15}$ and $R_{14}$ are both 3-methyl-butyl or when $R_{15}$ and $R_{14}$ are both 2-ethyl-butyl. $R_{15}$ and $R_{14}$ may be different $C_1$-$C_8$ substituted or unsubstituted n-alkyl moieties, such as when one of $R_{15}$ and $R_{14}$ is propyl and the other is ethyl.

In one embodiment, at least one or both of $R_{15}$ and $R_{14}$ is a $C_7$-$C_{24}$ substituted or unsubstituted aralkyl or heteroaralkyl. In one embodiment, at least one or both of $R_{15}$ and $R_{14}$ is a $C_7$-$C_{24}$ substituted or unsubstituted aralkyl or heteroaralkyl having two rings, such as 2-phenylbenzyl, 4-phenylbenzyl, 2-benzylbenzyl, 3-benzylbenzyl, 3,3,-diphenylpropryl, 3-(benzoimidazolyl)-propyl and the like. In one embodiment, at least one or both of $R_{15}$ and $R_{14}$ is a $C_7$-$C_{24}$ substituted or unsubstituted aralkyl or heteroaralkyl having one ring, such as 4-isopropylbenzyl, 4-fluorobenzyl, 4-tert-butylbenzyl, 3-imidazolyl-propyl, 2-phenylethyl and the like. In one embodiment, one of $R_{15}$ and $R_{14}$ is a $C_7$-$C_{24}$ substituted or unsubstituted aralkyl or heteroaralkyl, such as any of the specific substituted or unsubstituted aralkyl or heteroaralkyl moieties listed for any other formula, and the other $R_{15}$ and $R_{14}$ is hydrogen or a $C_1$-$C_8$ substituted or unsubstituted n-alkyl or ($C_3$-$C_8$) branched alkyl, such as ethyl, methyl, 3-methylbutyl and the like.

For any compound of formula (V), m and n may be the same or different. In one embodiment, m does not equal n, such as when m is 1 and n is 2. For instance, in one embodiment, m is 1, n is 2 and both $R_{15}$ and $R_{14}$ are 2-benzylbenzyl. However, it is understood that all possible combinations of m, n, $R_{15}$ and $R_{14}$ are intended.

In one embodiment, at least one or both of $R_{16}$ and $R_{17}$ is hydrogen. In one embodiment, at least one or both of $R_{16}$ and $R_{17}$ is a $C_1$-$C_8$ substituted or unsubstituted alkyl, such as a methyl, ethyl and a $C_1$-$C_8$ alkyl substituted with e.g., an —NH—$C_1$-$C_8$ alkyl such as when at least one or both of $R_{16}$ and $R_{17}$ is —$(CH_2)_3NHCH_2CH_3$.

It is understood and clearly conveyed by this disclosure that each $R_{14}$, $R_{15}$, $R_{16}$, $R_{17}$, m, and n disclosed in reference to formula (V) intends and includes all combinations thereof the same as if each and every combination of $R_{14}$, $R_{15}$, $R_{16}$, $R_{17}$, m, and n were specifically and individually listed.

Representative compounds of the formula (V) include, e.g.:

YZ33035

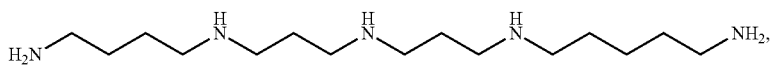

42-TDW-35C

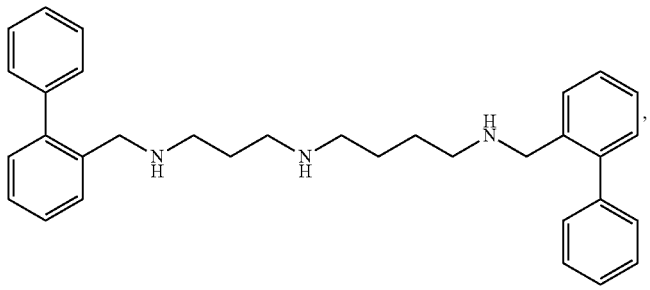

42-TDW-40C

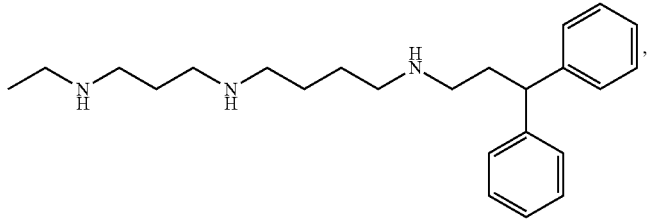

46-TDW-12

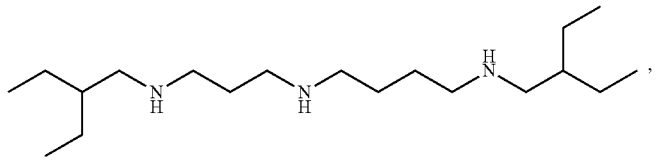

-continued

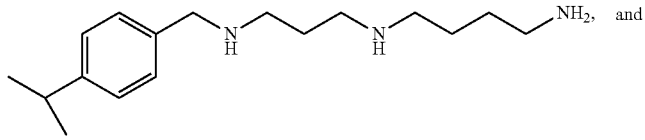
46-TDW-17C

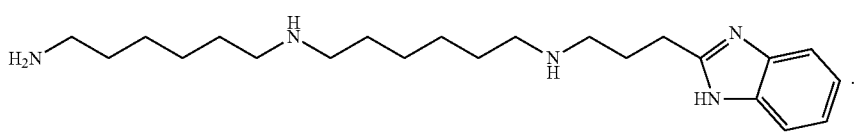
50-DHEJ-3C

In one embodiment, the polyamine is of the formula (VI):

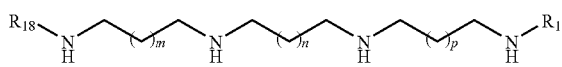
(VI)

or a salt, solvate, or hydrate thereof, wherein n is an integer from 1 to 12; m and p are independently an integer from 1 to 5; $R_{18}$ and $R_{19}$ are independently selected from the group consisting of hydrogen, $C_1$-$C_8$ unsubstituted alkyl (e.g., methyl, ethyl, Cert-butyl, isopropyl, pentyl, cyclobutyl), $C_1$-$C_8$ n-alkyl substituted with a cycloalkyl group comprising at least two rings, $C_7$-$C_{24}$ substituted or unsubstituted aralkyl or heteroaralkyl comprising at least two rings; and wherein: n is 1 when $R_{18}$ and $R_{19}$ are identical $C_1$-$C_8$ n-alkyl moieties substituted with a cycloalkyl group comprising at least two rings, or are identical aryl groups comprising at least two rings; and, at least one of $R_{18}$ and $R_{19}$ is either a $C_1$-$C_8$ n-alkyl substituted with a cycloalkyl group comprising at least two rings or a $C_7$-$C_{24}$ substituted or unsubstituted aralkyl comprising at least two rings.

In one embodiment, at least one or both of $R_{18}$ and $R_{19}$ is a $C_1$-$C_8$ n-alkyl substituted with a cycloalkyl group comprising at least two rings. The cycloalkyl group comprising at least two rings may be a spiro, fused or bridged cycloalkyl group. Representative examples of a $C_1$-$C_8$ n-alkyl substituted with a cycloalkyl group comprising two rings include moieties such as 2-(6,6-dimethylbicyclo[3.1.1]heptyl)ethyl and 2-(decahydronaphthyl)ethyl. In one embodiment, both $R_{18}$ and $R_{19}$ are 2-(6,6-dimethylbicyclo[3.1.1]heptyl)ethyl. In one embodiment, both $R_{18}$ and $R_{19}$ are 2-(decahydronaphthyl)ethyl. In one embodiment, one of $R_{18}$ and $R_{19}$ is 2-(6,6-dimethylbicyclo[3.1.1]heptyl)ethyl or 2-(decahydronaphthyl)ethyl and the other $R_{18}$ and $R_{19}$ is hydrogen or a $C_1$-$C_8$ unsubstituted alkyl such as ethyl.

In one embodiment, at least one or both of $R_{18}$ and $R_{19}$ is a $C_7$-$C_{24}$ substituted or unsubstituted aralkyl or heteroaralkyl comprising at least two rings, which rings may be but are not required to be fused. A substituted aralkyl or heteroaralkyl with reference to formula (VI) intends and includes alkanoyl moieties substituted with an aryl or heteroaryl group, i.e., —C(=O)-aryl, —C(=O)-aralkyl, —C (=O)-heteroaryl, and —C(=O)-heteroaralkyl. In one embodiment, the alkyl portion of the aralkyl or heteroaralkyl moiety is connected to the molecule via its alkyl moiety. For instance at least one or both of $R_{18}$ and $R_{19}$ may be an aralkyl moiety such as 2-phenylbenzyl, 4-phenylbenzyl, 3,3,-diphenylpropyl, 2-(2-phenylethyl)benzyl, 2-methyl-3-phenylbenzyl, 2-napthylethyl, 4-(pyrenyl)butyl, 2-(3-methylnapthyl)ethyl, 2-(1,2-dihydroacenaphth-4-yl)ethyl and the like. In another embodiment, at least one or both of $R_{18}$ and $R_{19}$ may be a heteroaralkyl moiety such as 3-(benzoimidazolyl)propanoyl, 1-(benzoimidazolyl)methanoyl, 2-(benzoimidazolyl)ethanoyl, 2-(benzoimidazolyl)ethyl and the like.

In one embodiment, each of m, n and p is the same, such as when m, n and p are each 1.

It is understood and clearly conveyed by this disclosure that each $R_{18}$, $R_{19}$, m, n and p disclosed in reference to formula (VI) intends and includes all combinations thereof the same as if each and every combination of $R_{18}$, $R_{19}$, m, n and p were specifically and individually listed.

Representative compounds of the formula (VI) include, e.g.:

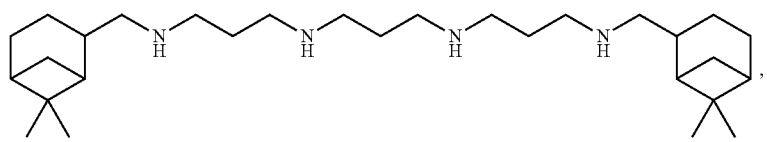
ZQW-35

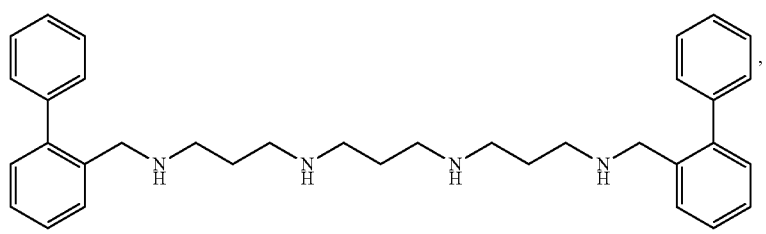
39-TDW-3

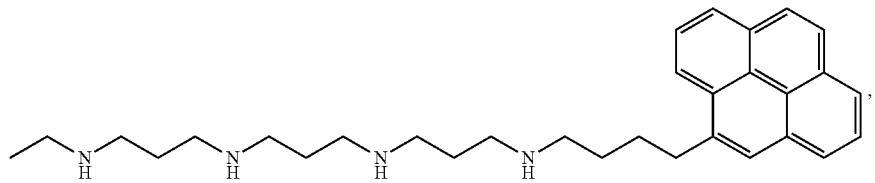

40-TDW-23

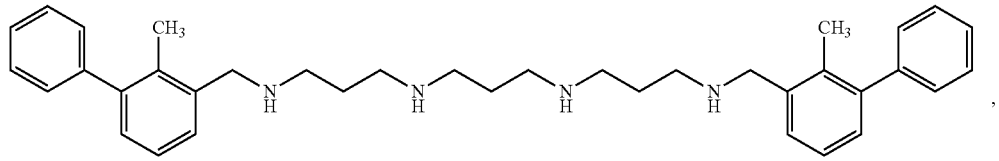

40-TDW-48

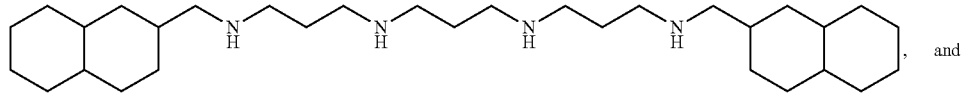

YZ-3312C, and

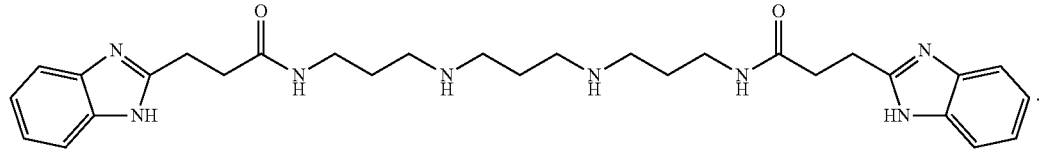

44-DHEJ-38

In one embodiment, the polyamine is of the formula (VII):

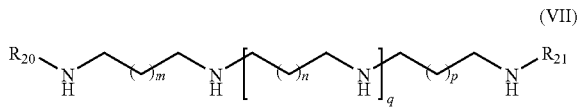

(VII)

or a salt, solvate, or hydrate thereof, wherein n is an integer from 1 to 12; m and p are independently an integer from 1 to 5; q is 0 or 1; $R_{20}$ and $R_{21}$ are independently selected from the group consisting of hydrogen, $C_1$-$C_8$ substituted or unsubstituted alkyl, —C(=O)—$C_1$-$C_8$ substituted or unsubstituted alkyl, —C(=O)—$C_1$-$C_8$ substituted or unsubstituted alkenyl, —C(=)—$C_1$-$C_8$ substituted or unsubstituted alkynyl, and $C_7$-$C_{24}$ substituted or unsubstituted aralkyl; and wherein the compound comprises at least one moiety selected from the group consisting of t-butyl, isopropyl, 2-ethylbutyl, 1-methylpropyl, 1-methylbutyl, 3-butenyl, isopent-2-enyl, 2-methylpropan-3-olyl, ethylthiyl, phenylthiyl, propynoyl, 1-methyl-1H-pyrrole-2-yl, trifluoromethyl, cyclopropanecarbaldehyde, halo-substituted phenyl, nitro-substituted phenyl, alkyl-substituted phenyl, 2,4,6-trimethylbenzyl, halo-S-substituted phenyl (such as para-($F_3$S)-phenyl, azido and 2-methylbutyl.

In one embodiment, q is 1. In one embodiment, q is 1 and n is 1.

In one embodiment at least one of $R_{20}$ and $R_{21}$ is hydrogen. In one embodiment at least one of $R_{20}$ and $R_{21}$ is $C_1$-$C_8$ substituted or unsubstituted alkyl, such as any of the substituted or unsubstituted alkyl moieties mentioned above for formulas (I)-(VI). In one embodiment at least one of $R_{20}$ and $R_{21}$ is a $C_7$-$C_{24}$ substituted or unsubstituted aralkyl, such as any of the $C_7$-$C_{24}$ substituted or unsubstituted aralkyl mentioned above for formulas (I)-(VI).

It is understood and clearly conveyed by this disclosure that each $R_{20}$, $R_{21}$, m, n, q and p disclosed in reference to formula (VII) intends and includes all combinations thereof the same as if each and every combination of $R_{20}$, $R_{21}$, m, n, q and p were specifically and individually listed.

Representative compounds of the formula (VII) include, e.g.:

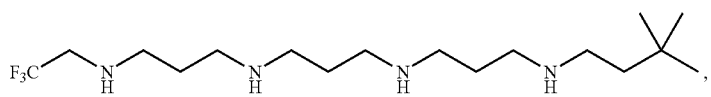

40-TDW-19

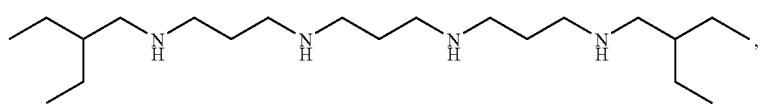

40-TDW-28

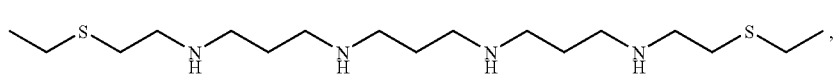

49-TDW-15

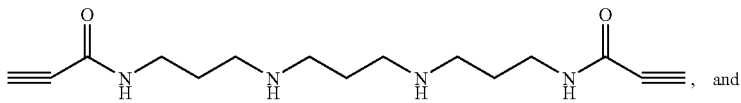

44-DHEJ-41

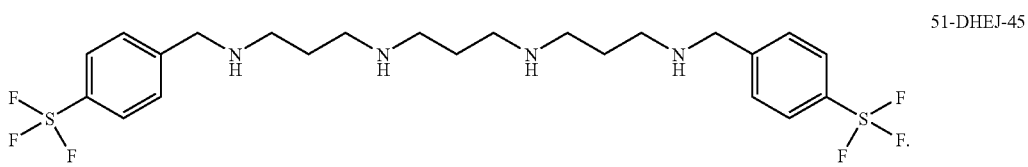

51-DHEJ-45

In one embodiment, the polyamine is of the formula (VIII):

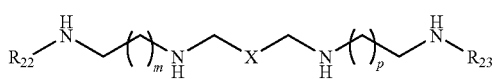

(VIII)

is cyclohex-1,3-diyl and m and p are both 1. In other embodiments, m and p are not the same, e.g., when m is 3 and p is 4.

It is understood and clearly conveyed by this disclosure that each $R_{22}$, $R_{23}$, m, n and p disclosed in reference to formula (VIII) intends and includes all combinations thereof the same as if each and every combination of $R_{22}$, $R_{23}$, m, n and p were specifically and individually listed.

Representative compounds of the formula (VIII) include, e.g.:

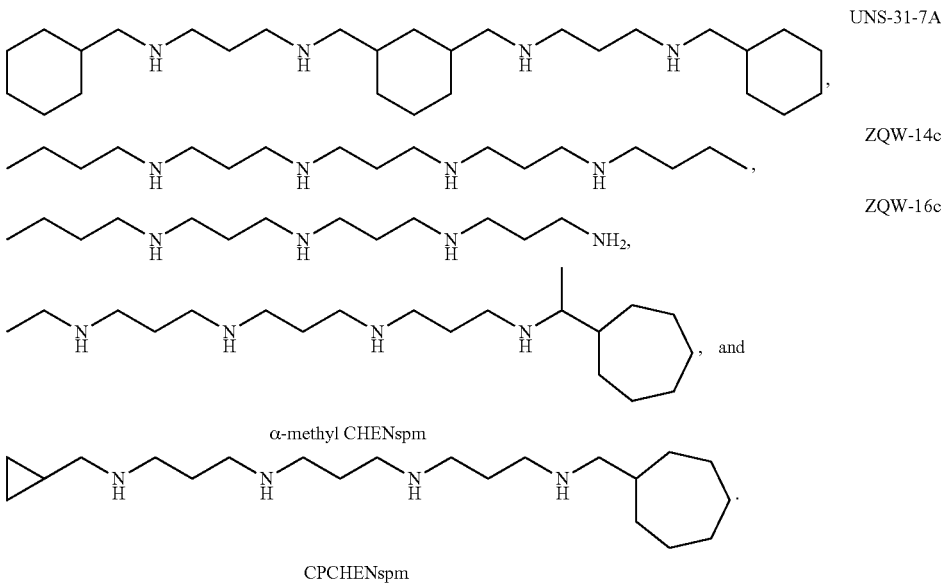

UNS-31-7A

ZQW-14c

ZQW-16c and

α-methyl CHENspm

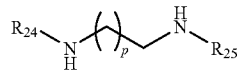

CPCHENspm or a salt, solvate, or hydrate thereof, wherein m and p are independently an integer from 1 to 5; X is —$(CH_2)n$- or cyclohex-1,3-diyl; n is an integer from 1 to 5; $R_{22}$ and $R_{23}$ are independently selected from the group consisting of hydrogen, n-butyl, ethyl, cyclohexylmethyl, cyclopentylmethyl, cyclopropylmethyl, cycloheptylmethyl, cyclohexyleth-2-yl, and benzyl; and when n is 5, at least one of $R_{22}$ and $R_{23}$ is hydrogen; when $R_{22}$ is ethyl, $R_{23}$ is hydrogen, n-butyl, cyclopentylmethyl, cyclohexyleth-2-yl or benzyl; and when $R_{23}$ is ethyl, $R_n$ is hydrogen, n-butyl, cyclopentylmethyl, cyclohexyleth-2-yl or benzyl; when X is cyclohex-1,3-diyl, $R_{22}$ and $R_{23}$ are not both benzyl or cyclopropylmethyl.

In one embodiment, X is —$(CH_2)n$ (e.g., $CH_2$ where n is 1). In one embodiment, X is $CH_2$ and m and p are both 1. In one embodiment, X is cyclohex-1,3-diyl. In one embodiment, X In one embodiment, the polyamine is of the formula (IX):

(IX)

or a salt, solvate, or hydrate thereof, wherein p is an integer from 1 to 5; $R_{24}$ is an amino-substituted cycloalkyl (e.g., a cycloalkyl group substituted with a primary, secondary, tertiary or quaternary amine) or a $C_2$-$C_8$ substituted or unsubstituted alkanoyl (which substituted alkanoyl may be substituted with one or more substituents such as those listed for "Substituted alkyl" including without limitation an alkanoyl substituted with a methyl and an alkylazide group); and $R_{25}$ is a $C_1$-$C_8$ substituted or unsubstituted alkyl or a $C_7$-$C_{24}$ substituted or unsubstituted aralkyl, such as those listed above for any of formulae (I)-(VIII).

In one embodiment, $R_{24}$ is an amino-substituted $C_3$-$C_{24}$ cycloalkyl, such as 5-$NH_2$-cycloheptyl, 3-$NH_2$-cyclopentyl and the like. In one embodiment, $R_{25}$ is a $C_1$-$C_8$ substituted or unsubstituted alkyl, which includes an n-alkyl group substituted with a cycloalkyl, such as in cyclopropylmethyl. In one embodiment, $R_{25}$ is cyclopropylmethyl or ethyl and $R_{24}$ is 5-$NH_2$-cycloheptyl or 3-$NH_2$-cyclopentyl. In one embodiment, $R_{24}$ is a $C_2$-$C_8$ substituted or unsubstituted alkanoyl and $R_{24}$ is a $C_7$-$C_{24}$ substituted or unsubstituted aralkyl, such as 4-phenylbenzyl.

It is understood and clearly conveyed by this disclosure that each $R_{24}$, $R_{25}$ and p disclosed in reference to formula (IX) intends and includes all combinations thereof the same as if each and every combination of $R_{24}$, $R_{25}$ and p were specifically and individually listed.

Representative compounds of the formula (IX) include, e.g.:

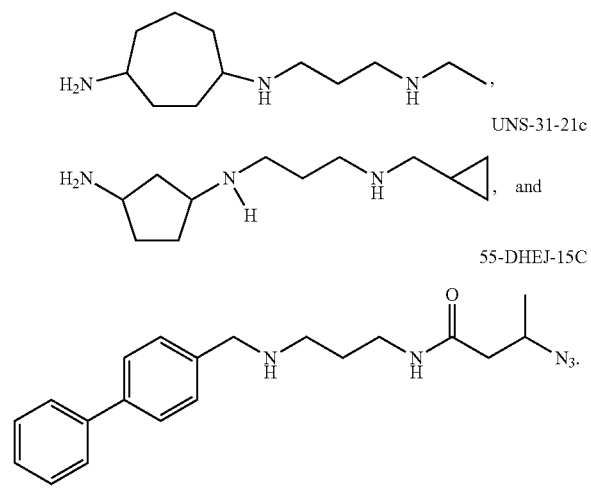

UNS-31-18
UNS-31-19c
UNS-31-21c, and
55-DHEJ-15C

For all formulae listed herein, such as formulae (I)-(IX), even if not explicitly stated, any substituent mentioned in one formula is intended to describe the same substituent in any other formula to the extent that the description conforms to the structural characterization of the formula described. For example, $R_1$ in formula I is intended to describe any other $R_1$ found in any other formula to the extent that the description conforms to the structural characterization of the formula described. Similarly, any description of, e.g., $C_1$-$C_8$ substituted or unsubstituted alkyl is intended to describe any other $C_1$-$C_8$ substituted or unsubstituted alkyl found in any other formula to the extent that the description conforms to the structural characterization of the formula described.

It is also recognized that any compounds listed as a particular salt thereof is not intended to limit the compound to such salt or form thereof. Similarly, where compounds are listed as a salt, the structure may or may not explicitly indicate positive or negative charges or the location thereof, and all possibilities thereof are intended. For instance, a compound listed as a 4HBr salt does not limit the compound to only the HBr salt and the compound may or may not show the + or − charges of the HBr salt, but rather all possibilities are intended.

Any of the polyamine compounds, such as compounds of the formula (I)-(IX) may be in a protected form, such as when any one or more amine (e.g., —NH—) is protected by a protecting group (Pg), such as in (—NPg-). Pg may be any protecting group, such as mesityl (e.g., NMes), Boc (e.g., —NBoc) or any other protecting group such as those described in, e.g. T. W. Green, P. G. M. Wuts, Protective Groups in Organic Synthesis, Wiley-Interscience, New York, 1999, which is incorporated herein by reference in its entirety.

Compounds within the scope of this invention and/or as described by any one or more of formulae (I)-(IX) include (but are not limited to) the compounds listed in Table A below.

In another embodiment, the invention embraces a method of treating cancer, by administering a therapeutically effective amount of one or more of the compounds of formula (M).

In another embodiment, the invention embraces a method of treating cancer, by administering a therapeutically effective amount of one or more of the compounds of formula (I).

In another embodiment, the invention embraces a method of treating cancer, by administering a therapeutically effective amount of one or more of the compounds of formula (II).

In another embodiment, the invention embraces a method of treating cancer, by administering a therapeutically effective amount of one or more of the compounds of formula (III).

In another embodiment, the invention embraces a method of treating cancer, by administering a therapeutically effective amount of one or more of the compounds of formula (IV).

In another embodiment, the invention embraces a method of treating cancer, by administering a therapeutically effective amount of one or more of the compounds of formula (V).

In another embodiment, the invention embraces a method of treating cancer, by administering a therapeutically effective amount of one or more of the compounds of formula (VI).

In another embodiment, the invention embraces a method of treating cancer, by administering a therapeutically effective amount of one or more of the compounds of formula (VII).

In another embodiment, the invention embraces a method of treating cancer, by administering a therapeutically effective amount of one or more of the compounds of formula (VIII).

In another embodiment, the invention embraces a method of treating cancer, by administering a therapeutically effective amount of one or more of the compounds of formula (IX).

In another embodiment, the invention embraces a method of treating cancer, by administering a therapeutically effective amount of one or more of the compounds listed in Table A or Table B.

In another embodiment, the invention embraces a method of inhibiting a histone demethylase enzyme, such as LSD1, by contacting the enzyme with an amount of one or more compounds, where the compound has at least one guanidine moiety or at least one biguanide moiety, in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (M) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (I) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (II) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (III) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (IV) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (V) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (VI) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (VII) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (VIII) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds of formula (IX) in an amount sufficient to inhibit the enzyme. The enzyme can be inhibited by at least about 25%, at least about 50%, at least about 75%, at least about 90%, at least about 95%, or at least about 99%.

In another embodiment, the invention embraces a method of inhibiting a histone demethylase enzyme, such as LSD1, by contacting the enzyme with an amount of one or more of the compounds listed in Table A or Table B in an amount sufficient to inhibit the enzyme. The enzyme can be inhibited by at least about 25%, at least about 50%, at least about 75%, at least about 90%, at least about 95%, or at least about 99%.

BRIEF DESCRIPTION OF THE DRAWINGS

FIG. 11 depicts a 96 hr MTS dose response experiments for compound 39-TDW-3 in H157, A549, and H82 cells.

FIG. 14 depicts a 96 hr MTS dose response experiments for compounds 39-TDw-47c and 39-TDW-43 in H157 cells.

FIG. 33 depicts the effects of XBI-54-13B and B182 on secreted frizzled-related proteins 1, 2, 4, and 5, and on GAPDH.

DETAILED DESCRIPTION OF THE INVENTION

Figure 1:
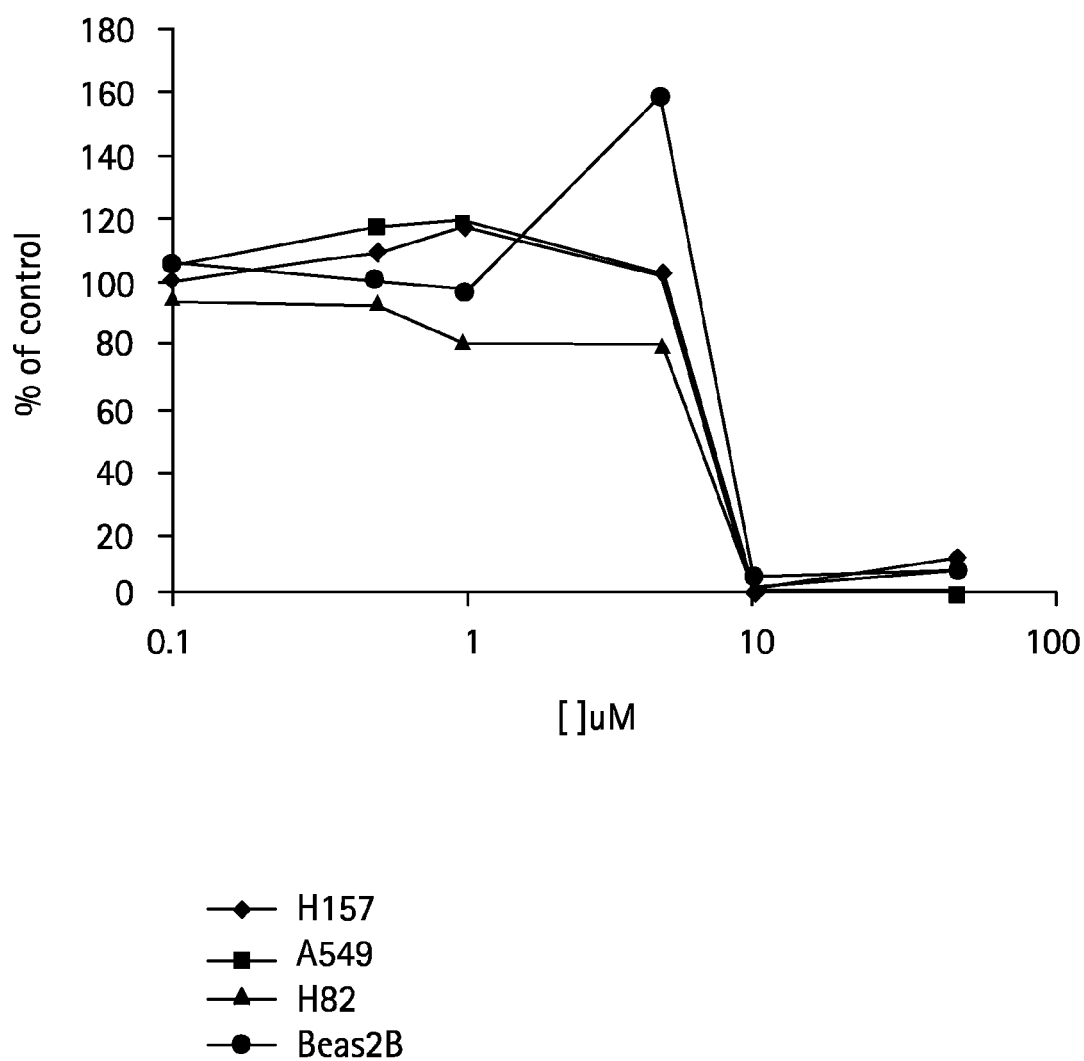
FIG. 1 depicts a 96 hr MTS dose response experiments for compound 46-TDW-23c in H157, A549, H82 and Beas2B cells.

The disclosure includes all salts of the compounds described herein. The invention also includes all non-salt compounds of any salt of a compound named herein, as well as other salts of any salt of a compound named herein. In one embodiment, the salts of the compounds comprise pharmaceutically acceptable salts. Pharmaceutically acceptable salts are those salts which retain the biological activity of the free compounds and which can be administered as drugs or pharmaceuticals to humans and/or animals. The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound may be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include; but are not limited to, procaine, dibenzylamine, N-ethylpiperidine, N,N'-dibenzylethylenediamine, and triethylamine salts. Salts of acidic compounds with amino acids, such as lysine salts, can also be prepared.

The disclosure includes all solvates of the compounds described herein, such as hydrates (in any ratios, e.g. monohydrates, dihydrates, hemihydrates, sesquihydrates), methanolates, ethanolates, etc.

Any compound described herein may occur in a combined salt and solvate form, for example the hyclate (monohydrochloride hemiethanolate hemihydrate) form.

The disclosure includes all stereoisomers of the compounds described herein, including diastereomers and enantiomers in optically pure or substantially optically pure form, as well as mixtures of stereoisomers in any ratio, including, but not limited to, racemic mixtures. Unless stereochemistry is explicitly indicated in a chemical structure or chemical name, the chemical structure or chemical name is intended to embrace all possible stereoisomers of the compound depicted.

The disclosure includes all crystal and non-crystalline forms of the compounds described herein, including all polymorphs, polycrystalline, and amorphous forms and any mixtures thereof.

The term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refers to alkyl groups that are neither cyclic nor branched, commonly designated as "n-alkyl" groups. $C_1$-$C_8$ n-alkyl consists of the following groups: —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, and —$CH_2CH_2CH_2CH_2CH_2CH_2CH_2CH_2$—. Other examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cycloalkyl groups can consist of one ring, including, but not limited to, groups such as cycloheptyl, or multiple bridged or fused rings, including, but not limited to, groups such as adamantyl or norbornyl groups. Cycloalkyl groups can also contain alkyl groups in addition to the cyclic portion, e.g., 2,6,6-trimethylbicyclo[3.1.1]heptane, 2-methyldecalin (2-methyldecahydronaphthalene), cyclopropylmethyl, cyclohexylmethyl, cycloheptylmethyl, and the like.

"Substituted alkyl" refers to alkyl groups substituted with one or more substituents including, but not limited to, groups such as halogen (including fluoro, chloro, bromo, and/or iodo-substituted alkyl such as a monohaloalkyl, dihaloalkyl, trihaloalkyl or multihaloalkyl, including a perhalooalkyl, for example, perfluoroalkyl, percholoralkyl, trifluoromethyl or pentachloroethyl), alkoxy, acyloxy, amino (including $NH_2$, NHalkyl and N(alkyl)$_2$), hydroxyl, mercapto, carboxy, benzyloxy, phenyl, benzyl, cyano, nitro, acyl, acylamino, amidino, alkyl amidino, thioamidino, aminoacyl, aryl, substituted aryl, aryloxy, azido, thioalkyl, —OS(O)$_2$-alkyl, thioalkoxy, carboxaldehyde, carboalkoxy and carboxamide, or a functionality that can be suitably blocked, if necessary for purposes of the invention, with a protecting group. Examples of substituted alkyl groups include, but are not limited to, $CF_3$, $CF_2CF_3$, and other perfluoro and perhalo groups; —$CH_2$—OH; —$CH_2CH_2CH(NH_2)CH_3$, etc. Alkyl groups can be substituted with other alkyl groups, e.g., $C_3$-$C_{24}$ cycloalkyl groups.

The term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C=C—). Examples of alkenyl groups include, but are not limited to, —$CH_2$—CH=CH—$CH_3$; and —$CH_2$—$CH_2$-cyclohexenyl, where the ethyl group can be attached to the cyclohexenyl moiety at any available carbon valence. The term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched-chain, or cyclic alkyl, alkenyl, or alkynyl groups, and any combination thereof. "Substituted alkenyl," "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or any group listed above for "Substituted alkyl," or a functionality that can be suitably blocked, if necessary for purposes of the invention, with a protecting group.

"Aryl" or "Ar" refers to an aromatic carbocyclic group having a single ring (including, but not limited to, groups such as phenyl), two or more rings connected to each other (including, but not limited to, groups such as biphenyl and p-diphenylbenzene) or two or more condensed rings (including, but not limited to, groups such as naphthyl, anthryl, or pyrenyl), and includes both unsubstituted and substituted aryl groups. Aryls, unless otherwise specified, contain from 6 to 20 carbon atoms in the ring portion. A preferred range for aryls contains 6 to 12 carbon atoms in the ring portion. "Substituted aryls" refers to aryls substituted with one or more substituents, including, but not limited to, groups such as substituted or unsubstituted alkyl, substituted or unsubstituted alkenyl, substituted or unsubstituted alkynyl, substituted or unsubstituted hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or any group listed above for "Substituted alkyl," or a functionality that can be suitably blocked, if necessary for purposes of the invention, with a protecting group. "Aralkyl" designates an alkyl-substituted aryl group, where any aryl can be attached to the alkyl; the alkyl portion can comprise one, two, or three straight chains of 1 to 6 carbon atoms each or one, two, or three branched chains of 3 to 6 carbon atoms each or any combination thereof. Aralkyl groups can consist of two aryl groups connected by an alkyl group, such as diphenylmethane or 2-methyl-1-(phenethyl)benzene. When an aralkyl group is indicated as a substituent, the aralkyl group can be connected to the remainder of the molecule at any available valence on either its alkyl moiety or aryl moiety; e.g., the tolyl aralkyl group can be connected to the remainder of the molecule by replacing any of the five hydrogens on the aromatic ring moiety with the remainder of the molecule, or by replacing one of the alpha-hydrogens on the methyl moiety with the remainder of the molecule. Preferably, the aralkyl group is connected to the remainder of the molecule via the alkyl moiety.

A preferred aryl group is phenyl, which can be substituted or unsubstituted. Substituents for substituted phenyl groups include lower alkyl (—$C_1$-$C_4$ alkyl), or a halogen (chlorine (Cl), bromine (Br), iodine (I), or fluorine (F); hydroxy (—OH), or lower alkoxy (—$C_1$-$C_4$ alkoxy), such as methoxy, ethoxy, propyloxy (propoxy) (either n-propoxy or i-propoxy), and butoxy (either n-butoxy, i-butoxy, sec-butoxy, or tert-butoxy); a preferred alkoxy substituent is methoxy. Substituted phenyl groups preferably have one or two substituents; more preferably, one substituent.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule at any valence where a hydrogen can be removed, for example, at a heteroatom or at a carbon atom (if a valence is available at such an atom by removing a hydrogen). Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—$CH(CH_3)$—S—$CH_3$, —$CH_2$—$CH_2$—NH—$CH_2$—$CH_2$—, 1-ethyl-6-propylpiperidino, and morpholino. Examples of heteroalkenyl groups include, but are not limited to, groups such as —CH=CH—NH—$CH(CH_3)$—$CH_2$—.

"Heteroaryl" or "HetAr" refers to an aromatic carbocyclic group having a single ring (including, but not limited to, examples such as pyridyl, imidazolyl, thiophene, or furyl) or two or more condensed rings (including, but not limited to, examples such as indolizinyl, indole, benzimidazole, benzotriazole, or benzothienyl) and having at least one hetero atom, including, but not limited to, heteroatoms such as N, O, P, or S, within the ring. Unless otherwise specified, heteroalkyl, heteroalkenyl, heteroalkynyl, and heteroaryl groups have between one and five heteroatoms and between one and twelve carbon atoms. "Substituted heteroalkyl," "substituted heteroalkenyl," "substituted heteroalkynyl," and "substituted heteroaryl" groups refer to heteroalkyl, heteroalkenyl, heteroalkynyl, and heteroaryl groups substituted with one or more substituents, including, but not limited to, groups such as substituted or unsubstituted alkyl, substituted or unsubstituted alkenyl, substituted or unsubstituted alkynyl, substituted or unsubstituted benzyl, substituted or unsubstituted hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or any group listed above for "Substituted alkyl," or a functionality that can be suitably blocked, if necessary for purposes of the invention, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—$SO_2$-phenyl, —NH—(C=O) O-alkyl, —NH—(C=O)O-alkyl-aryl, and —NH—(C=O)-alkyl. If chemically possible, the heteroatom(s) and/or the carbon atoms of the group can be substituted. A "heteroaralkyl" group is a heteroaryl group substituted with at least one alkyl group. The heteroatom(s) can also be in oxidized form, if chemically possible.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, propyloxy (propoxy) (either n-propoxy or i-propoxy), and butoxy (either n-butoxy, i-butoxy, sec-butoxy, or tert-butoxy).

The terms "halo" and "halogen" as used herein refer to the Group VIIa elements (Group 17 elements in the 2005 IUPAC Periodic Table, IUPAC Nomenclature of Inorganic Chemistry) and include Cl, Br, F and I substituents.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al, (1999) Protective Groups in Organic Synthesis, (Wiley-Interscience., New York). Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5 bromo 7-nitroindolinyl, and the like. Hydroxyl protecting groups include, but are not limited to, Fmoc, TBS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4 nitrophenethyloxymethyloxycarbonyl).

Specific Compounds

Examples of compounds useful in the invention are depicted in Table A. While the compounds are depicted as salts, such as the hydrobromide or trifluoroacetate salt, it is to be understood that the disclosure in the table embraces all salts, hydrates, and solvates of the compounds depicted therein, as well as the non-salt, non-hydrate/non-solvate form of the compound, as is well understood by the skilled artisan.

TABLE A

Compound

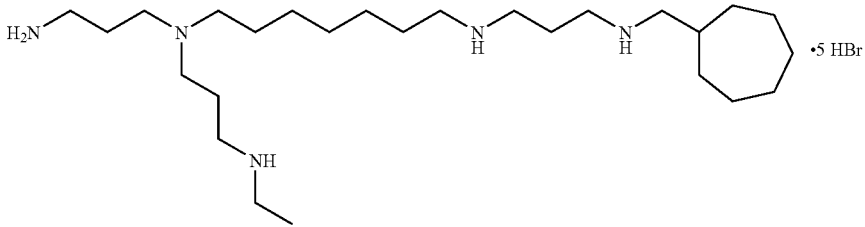

ZQW-27-11c

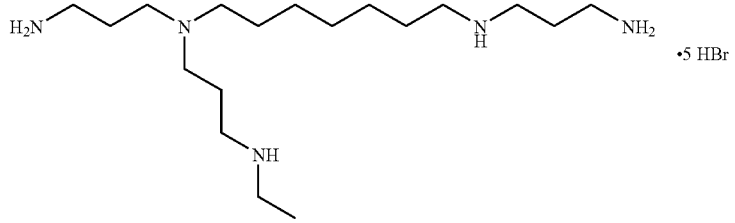

ZQW-27-9

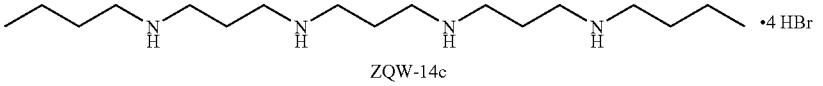

ZQW-14c

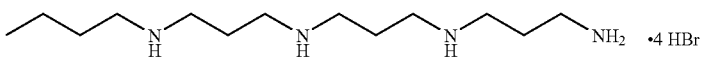

ZQW-16c

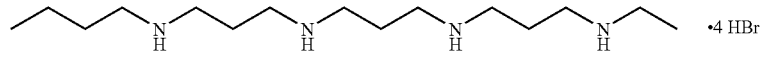

ZQW-19

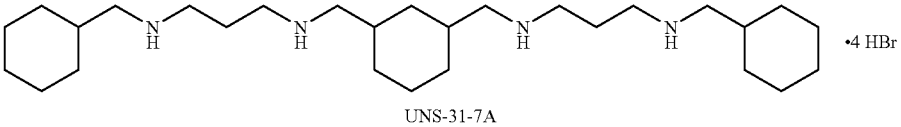

UNS-31-7A

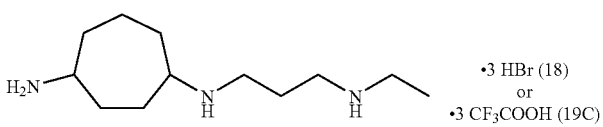

UNS-31-18
UNS-31-19c

TABLE A-continued
Compound
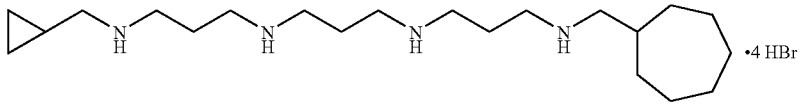
CPCHENspm
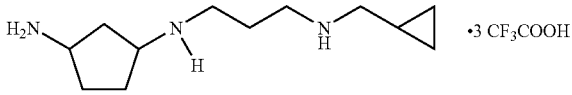
UNS-31-21c
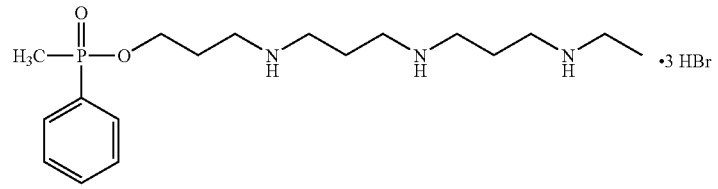
BEPPSpd
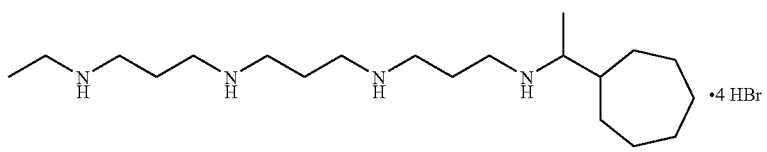
α-methyl CHENspm
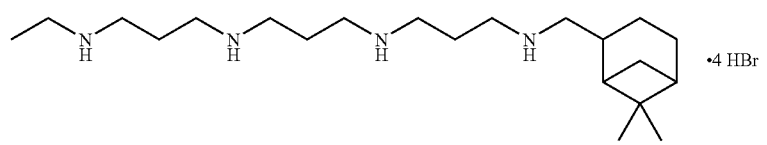
ZQW-36
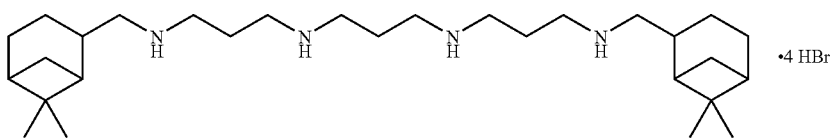
ZQW-35
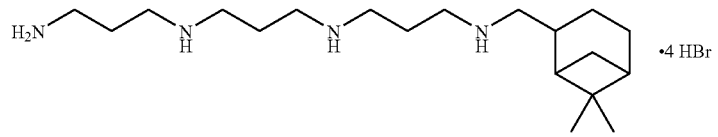
ZQW-35C
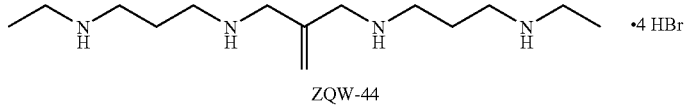
ZQW-44
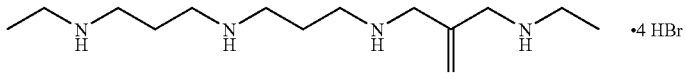
ZQW-46

TABLE A-continued
| Compound |
|---|
| 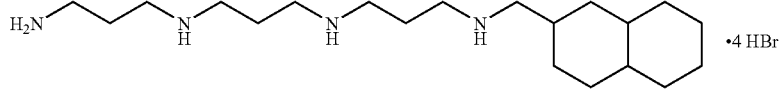 YZ-3312 |
| 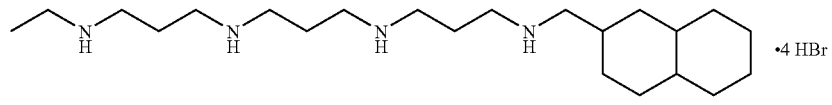 YZ-3311C |
| 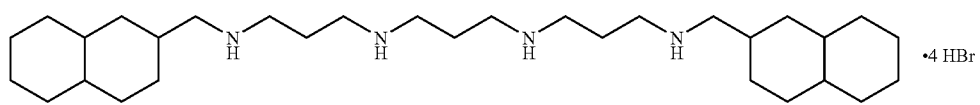 YZ-3312C |
| 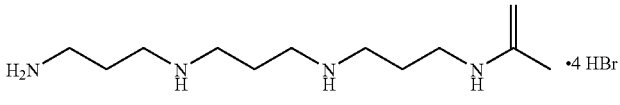 ZQW-35-7C |
| 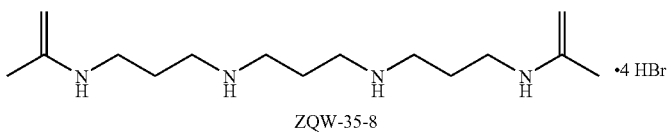 ZQW-35-8 |
| 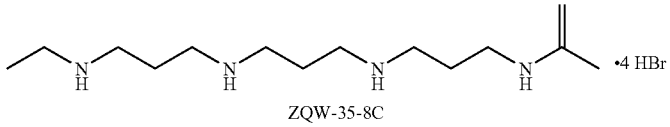 ZQW-35-8C |
| 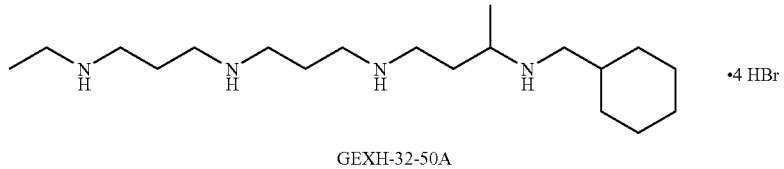 GEXH-32-50A |
| 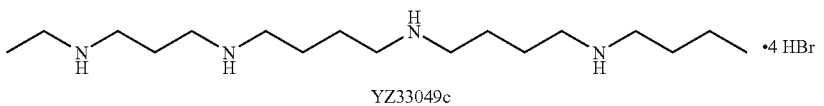 YZ33049c |
| 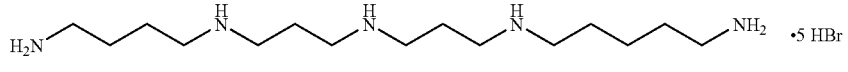 YZ33035 |
| 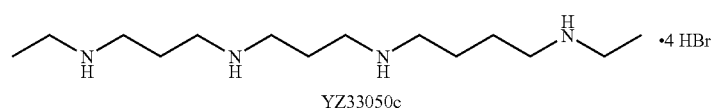 YZ33050c |
| 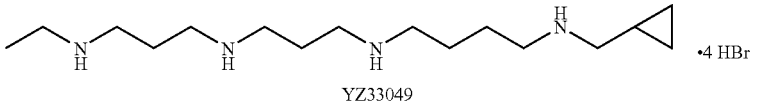 YZ33049 |

TABLE A-continued
| Compound |
|---|
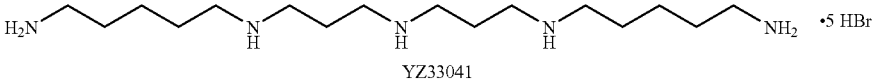
YZ33041 · 5 HBr
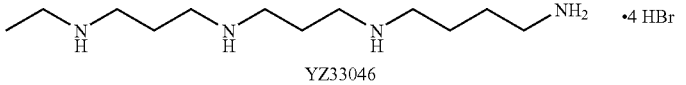
YZ33046 · 4 HBr
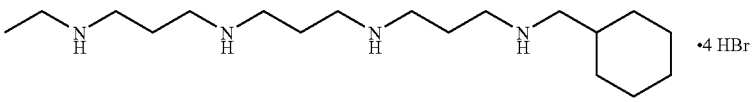
CHEXSpm · 4 HBr
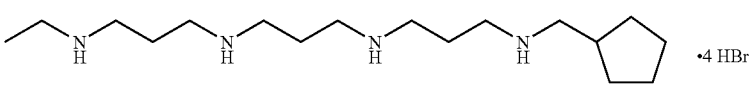
CPENTSpm · 4 HBr
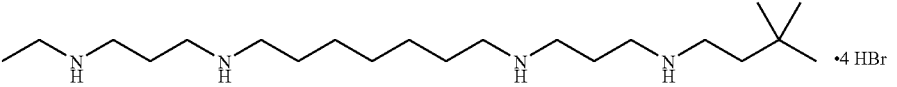
39-TDW-11 · 4 HBr
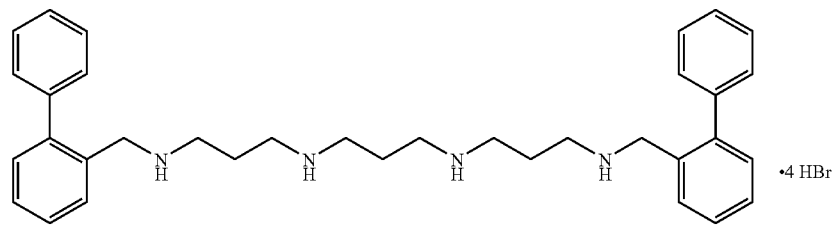
39-TDW-3 · 4 HBr
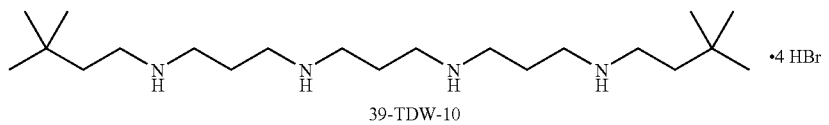
39-TDW-10 · 4 HBr
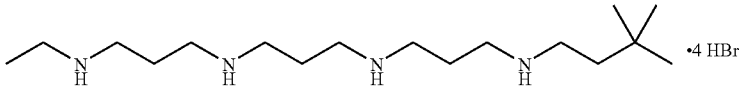
39-TDW-12C · 4 HBr
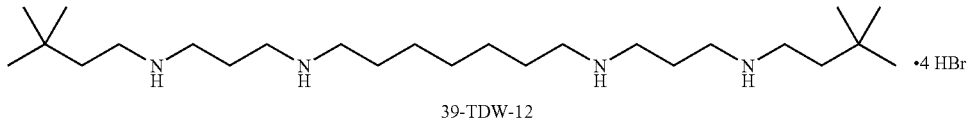
39-TDW-12 · 4 HBr
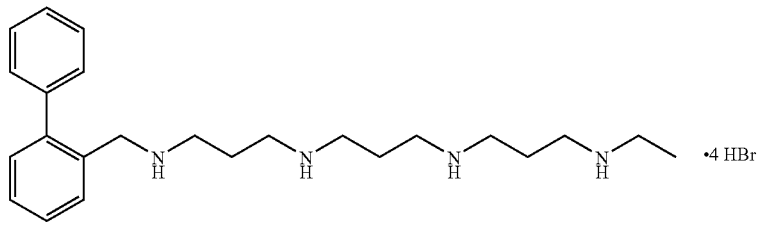
39-TDW-20c · 4 HBr TABLE A-continued

| Compound |
|---|

40-TDW-1 · 4 HBr

39-TDW-47C · 4 HBr

39-TDW-43 · 4 HBr

40-TDW-19 · 4 HBr

40-TDW-26c · 4 HBr

40-TDW-23 · 4 HBr

40-TDW-31C · 4 HBr

40-TDW-29C · 4 HBr

TABLE A-continued
| Compound |
|---|
| 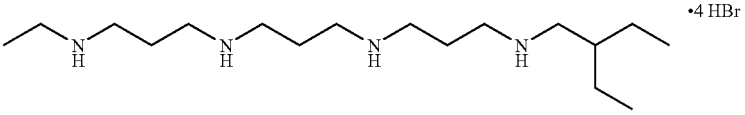 •4 HBr<br>40-TDW-30 |
| 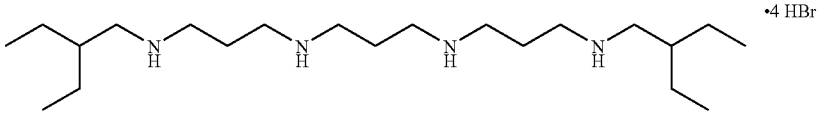 •4 HBr<br>40-TDW-28 |
| 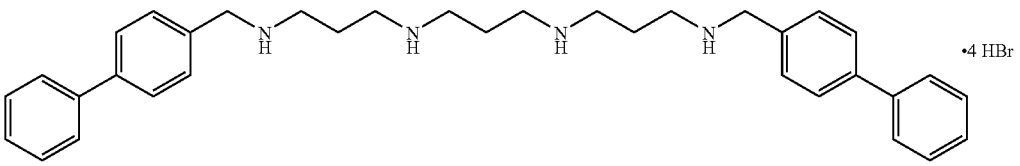 •4 HBr<br>40-TDW-35 |
| 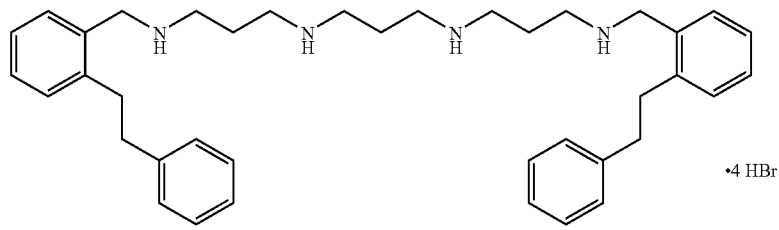 •4 HBr<br>40-TDW-37 |
| 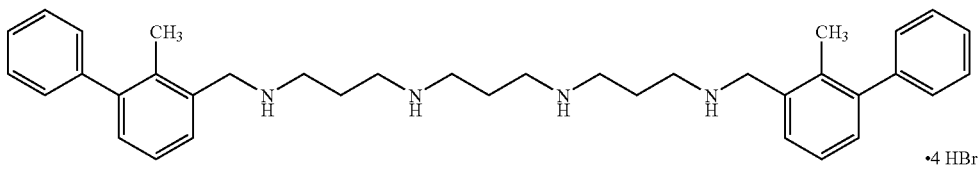 •4 HBr<br>40-TDW-48 |
| 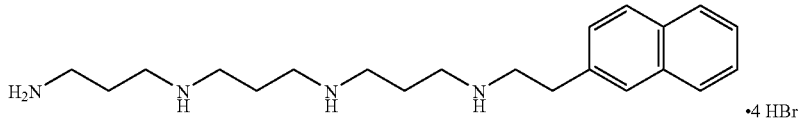 •4 HBr<br>42-TDW-4 |
| 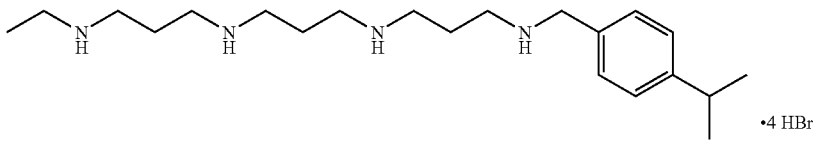 •4 HBr<br>42-TDW-4C |
| 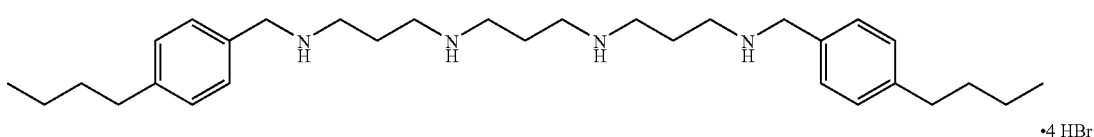 •4 HBr<br>42-TDW-9 |

TABLE A-continued
Compound
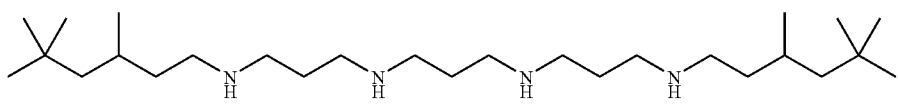
42-TDW-12 ·4 HBr
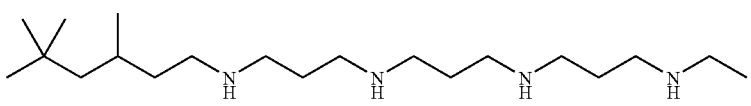
42-TDW-14 ·4 HBr
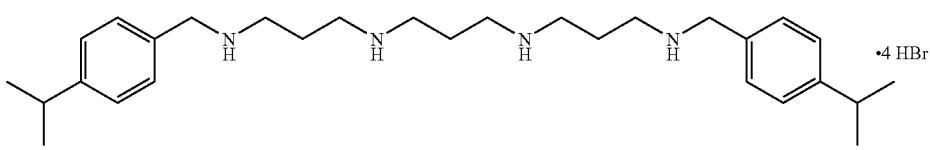
42-TDW-20c ·4 HBr
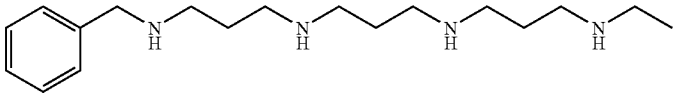
42-TDW-21c ·4 HBr
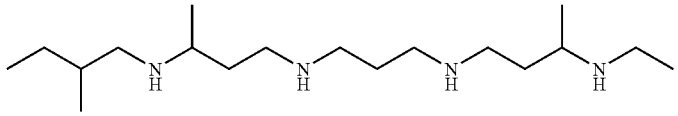
44-DHEJ-4C ·4 HBr
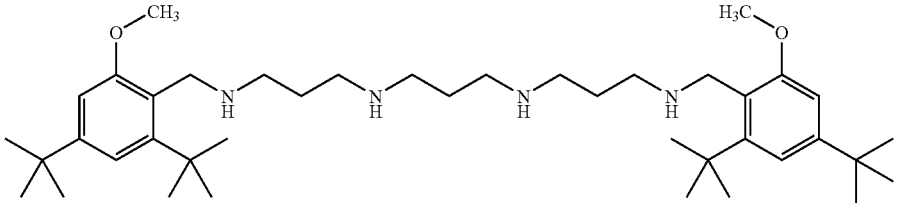
44-DHEJ-8C ·4 HF
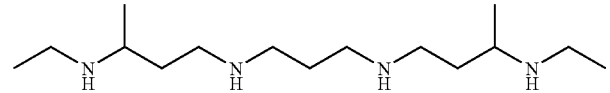
44-DHEJ-7C ·4 HBr
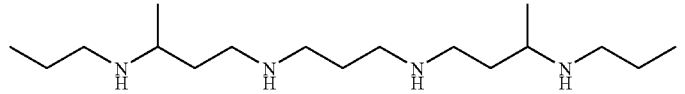
44-DHEJ-9 ·4 HBr
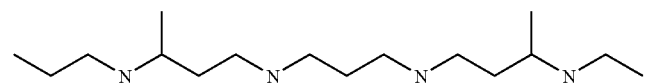
44-DHEJ-12C ·4 HBr TABLE A-continued
Compound
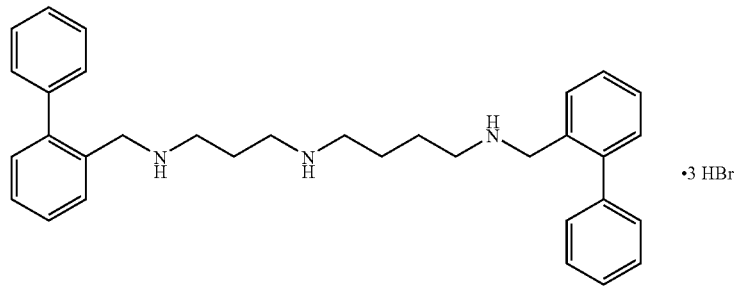
42-TDW-35C
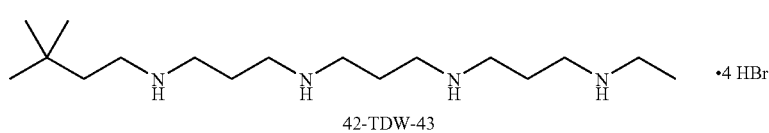
42-TDW-43
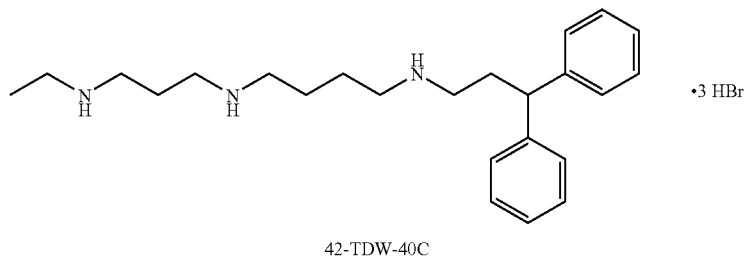
42-TDW-40C
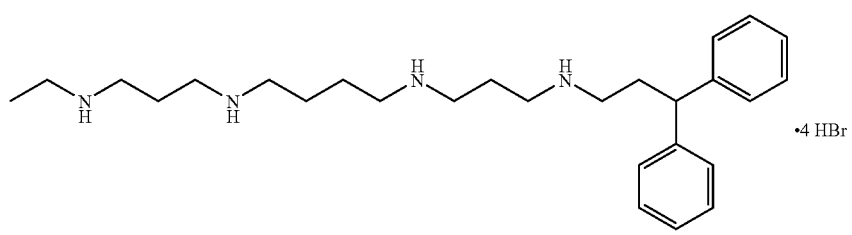
42-TDW-40
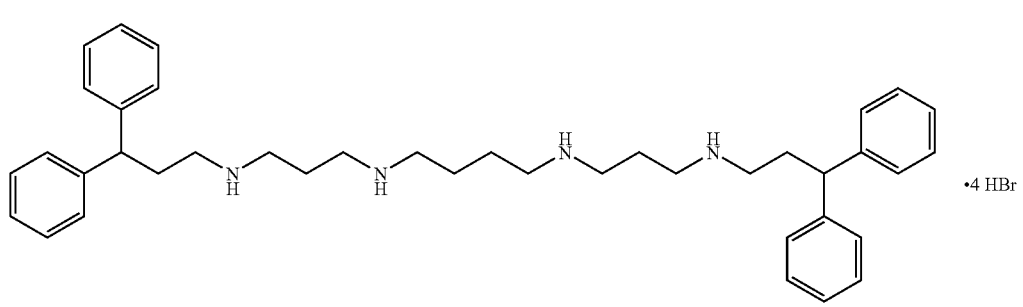
42-TDW-38
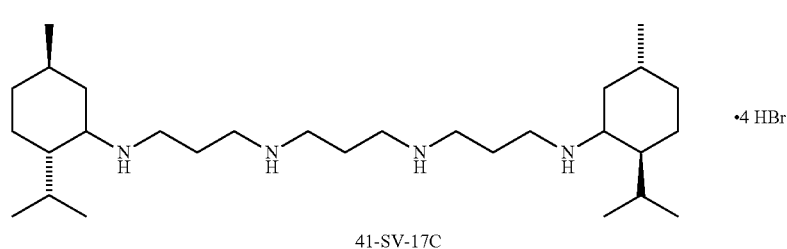
41-SV-17C TABLE A-continued
Compound
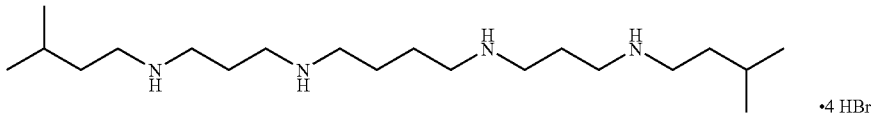
42-TDW-45 •4 HBr
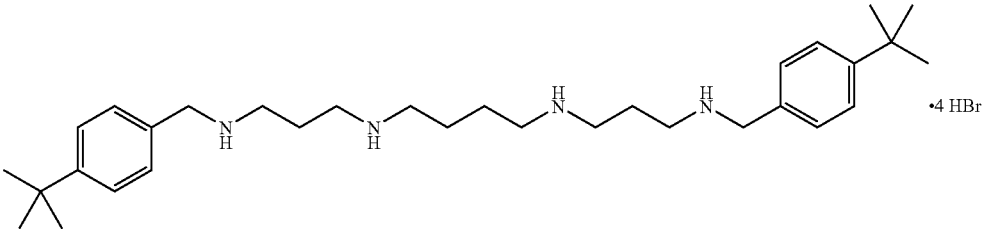
46-TDW-1C •4 HBr
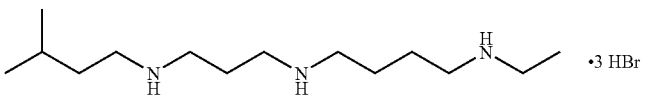
42-TDW-50 •3 HBr
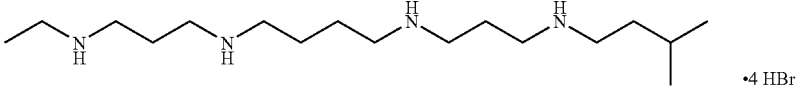
42-TDW-45C •4 HBr
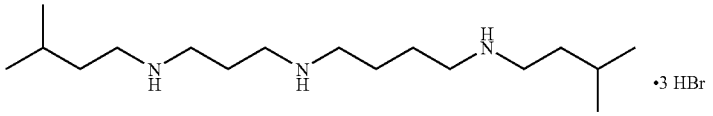
42-TDW-49 •3 HBr
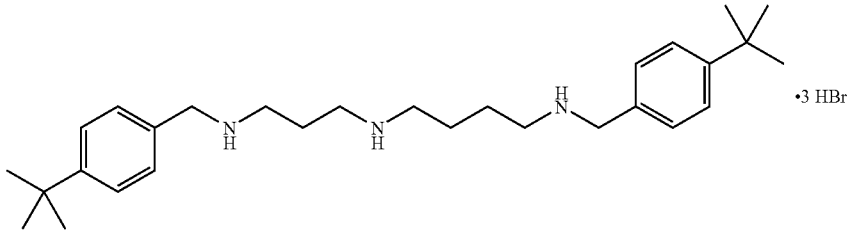
46-TDW-2 •3 HBr
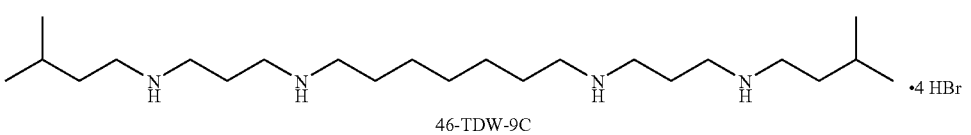
46-TDW-9C •4 HBr TABLE A-continued
Compound
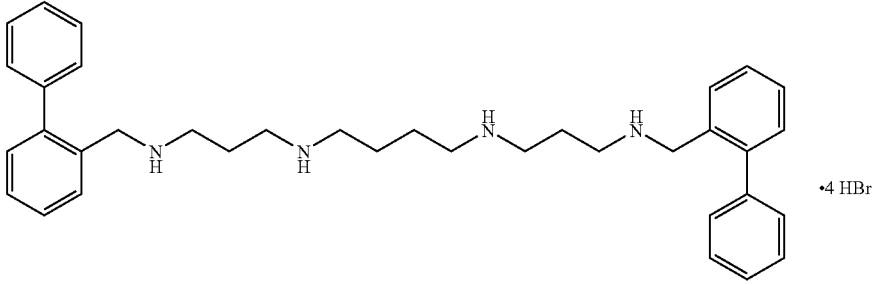
46-TDW-9 •4 HBr
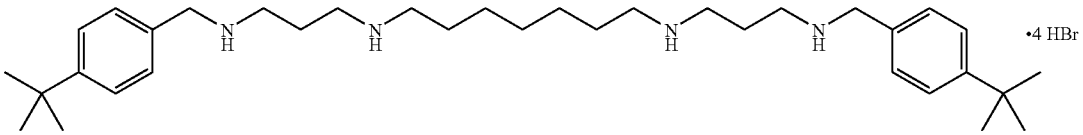
46-TDW-10 •4 HBr
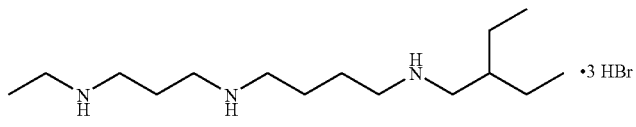
46-TDW-12C •3 HBr
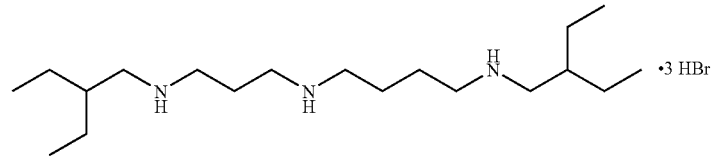
46-TDW-12 •3 HBr
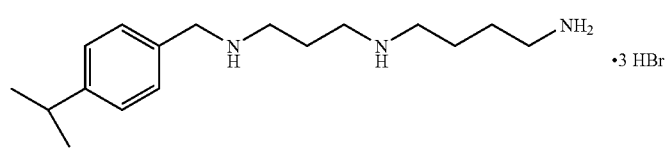
46-TDW-17C •3 HBr
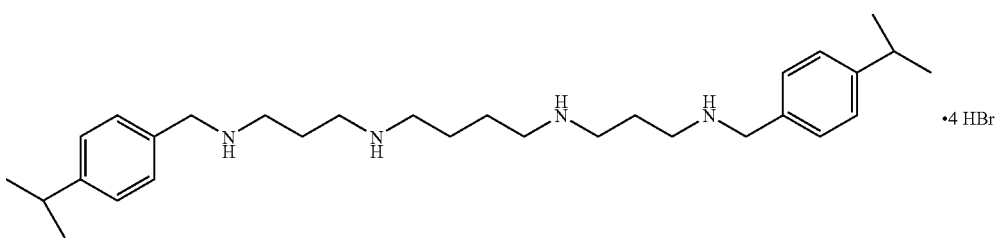
46-TDW-19C •4 HBr TABLE A-continued
Compound
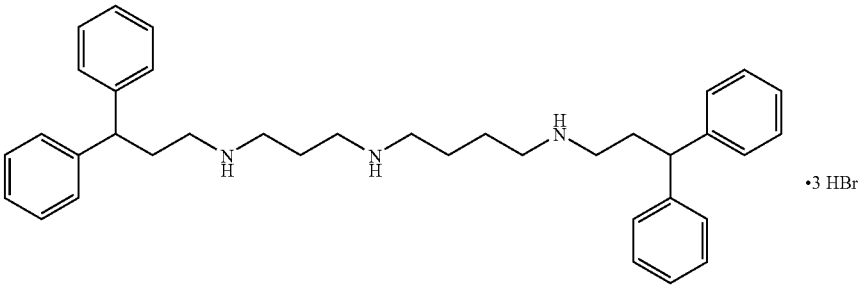
46-TDW-23C
·3 HBr
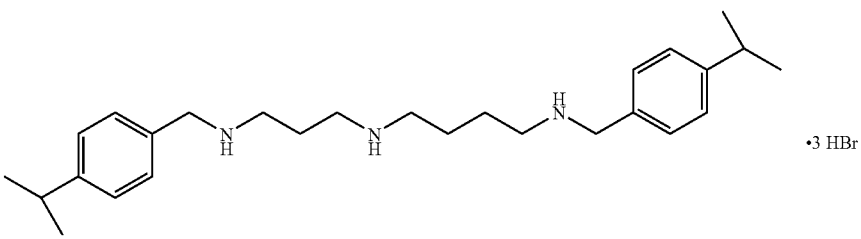
46-TDW-22
·3 HBr
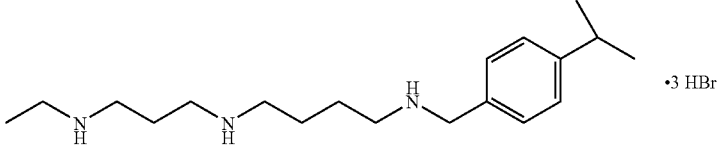
46-TDW-24
·3 HBr
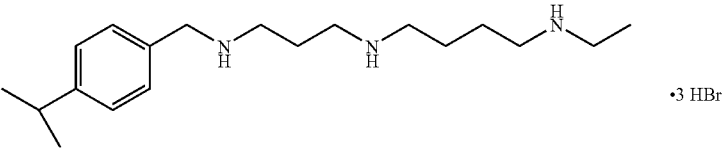
46-TDW-29
·3 HBr
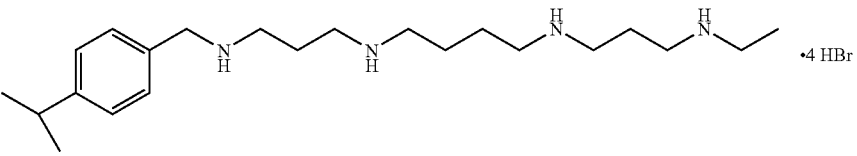
46-TDW-35
·4 HBr
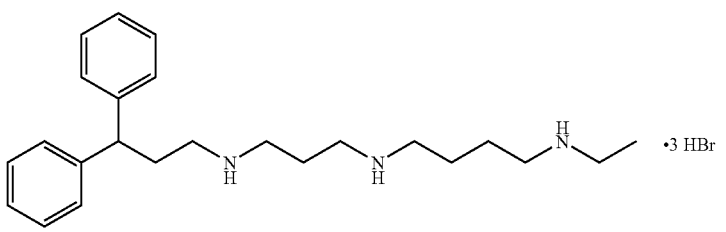
46-TDW-25C
·3 HBr

TABLE A-continued
Compound
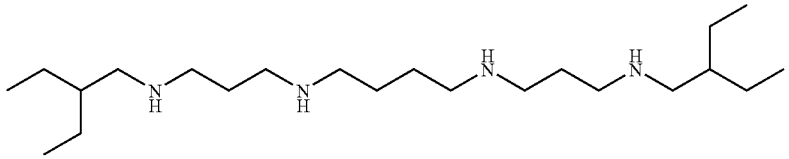
46-TDW-31C · 4 HBr
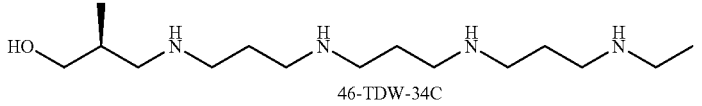
46-TDW-34C · 4 HBr
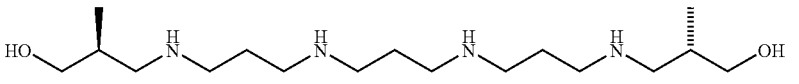
46-TDW-30 · 4 HBr
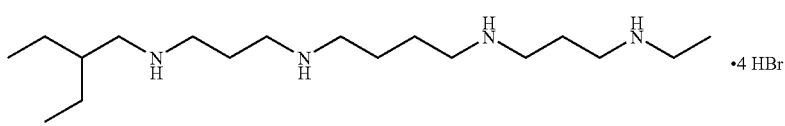
46-TDW-35C · 4 HBr
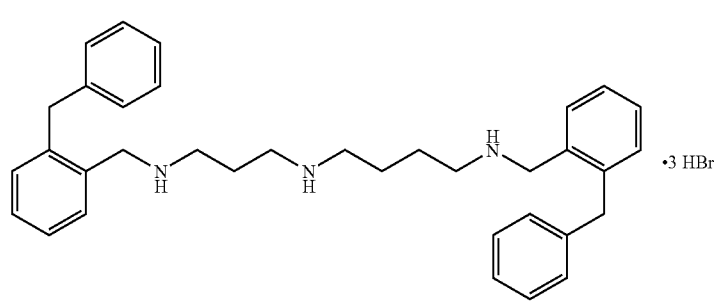
46-TDW-39 · 3 HBr
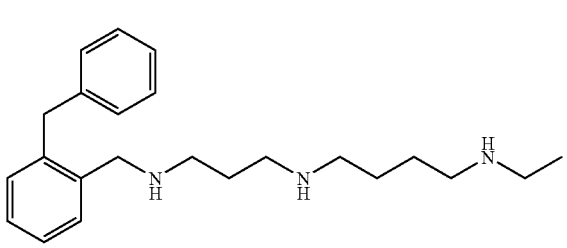
46-TDW-42 · 3 HBr
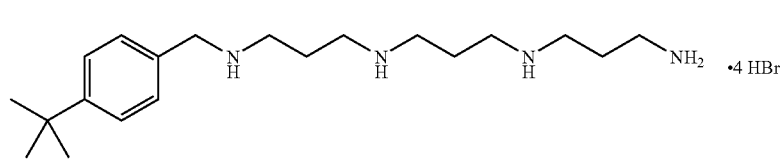
46-TDW-44 · 4 HBr TABLE A-continued
Compound
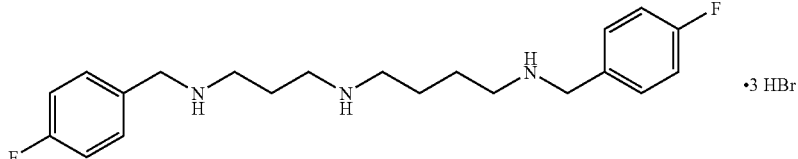
49-TDW-44C
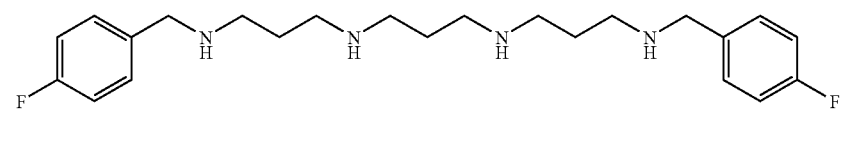
49-TDW-45
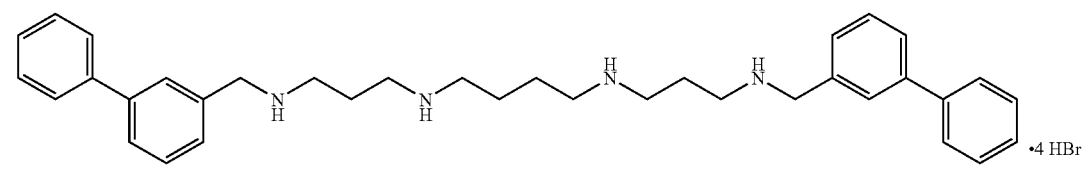
49-TDW-1C
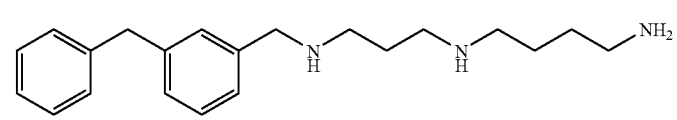
46-TDW-47
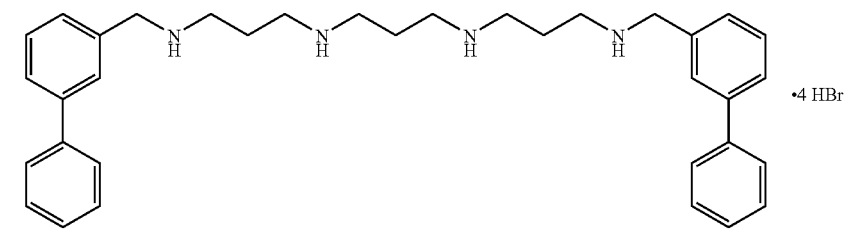
46-TDW-49C
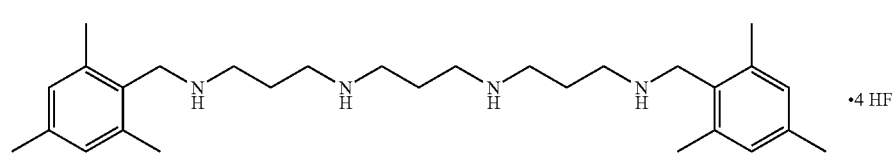
44-DHEJ-37
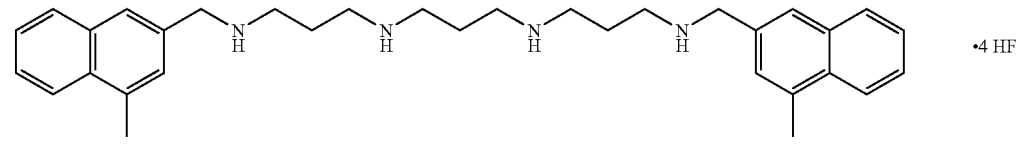
44-DHEJ-37C
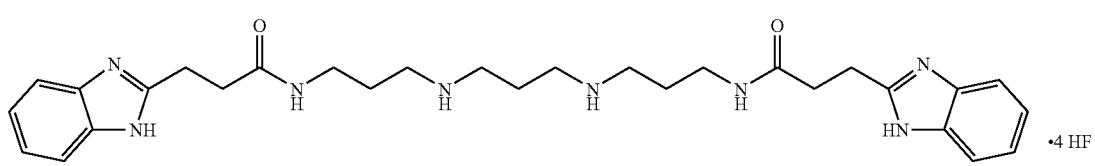
44-DHEJ-38

TABLE A-continued
Compound
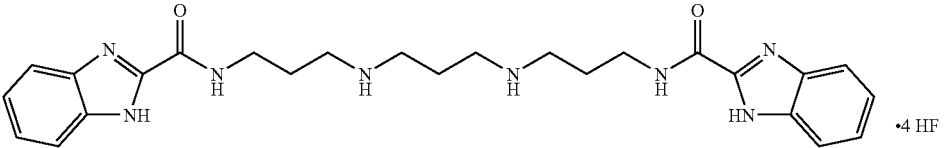
44-DHEJ-40C · 4 HF
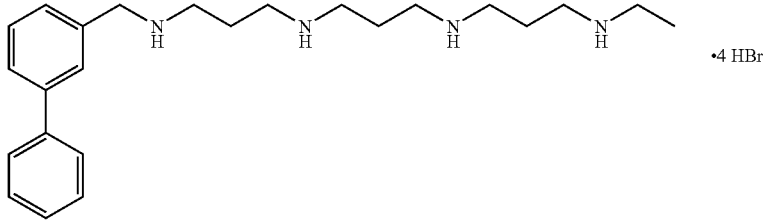
49-TDW-3C · 4 HBr
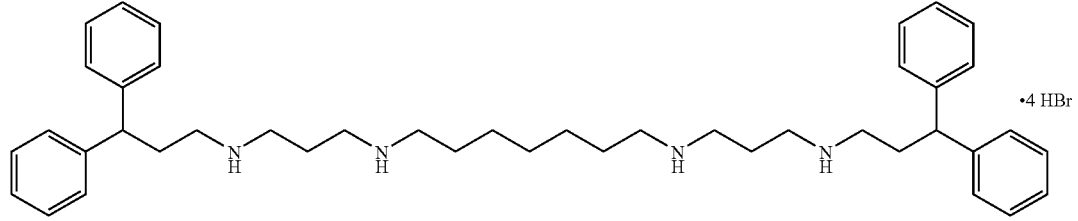
49-TDW-5C · 4 HBr
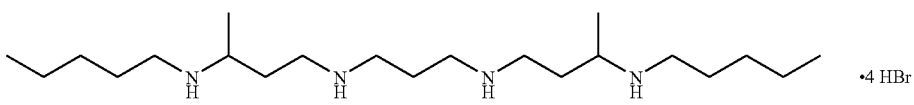
44-DHEJ-36 · 4 HBr
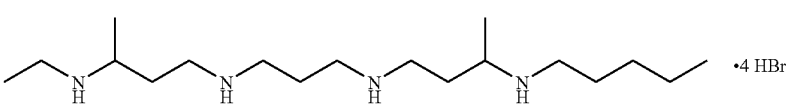
44-DHEJ-36C · 4 HBr
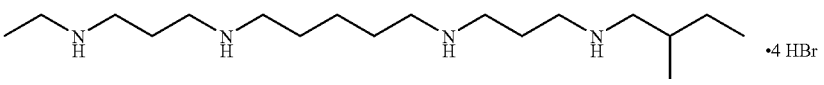
51-DHEJ-A · 4 HBr
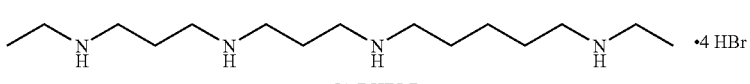
51-DHEJ-B · 4 HBr
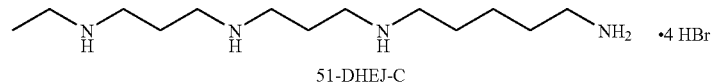
51-DHEJ-C · 4 HBr
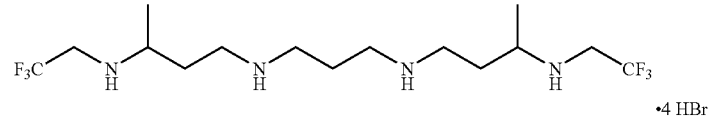
44-DHEJ-35C · 4 HBr TABLE A-continued

| Compound |
|---|

Structure: CH₃CH₂-NH-(CH₂)₃-NH-(CH₂)₄-NH-(CH₂)₃-NH-CH₂CH₃ · 4 HBr
44-DHEJ-48C

Structure: CH₃CH₂-NH-(CH₂)₃-NH-(CH₂)₄-NH-(CH₂)₃-NH₂ · 4 HBr
44-DHEJ-49

Structure: 2,4,5-trifluorobenzyl-NH-CH(CH₃)CH₂CH₂-NH-(CH₂)₃-NH-CH₂CH₂CH(CH₃)-NH-benzyl-2,4,5-trifluoro · 4 HF
44-DHEJ-5C Structure: 2,4,5-trifluorobenzyl-NH-(CH₂)₃-NH-(CH₂)₃-NH-(CH₂)₃-NH-benzyl-2,4,5-trifluoro · 4 HF
44-DHEJ-10C Structure: Ph-NH-C(=NH)-NH-(CH₂)₃-NH-(CH₂)₃-NH-(CH₂)₃-NH-C(=NH)-NH-Ph · 4 HBr
B188-2

Structure: Ph-NH-C(=NH)-NH-(CH₂)₃-NH-(CH₂)₇-NH-(CH₂)₃-NH-C(=NH)-NH-Ph · 4 HBr
B205-1

Structure: CH₃-NH-C(=NH)-NH-(CH₂)₃-NH-(CH₂)₇-NH-(CH₂)₃-NH-C(=NH)-NH-CH₃ · 4 HBr
B181

Structure: CH₃-NH-C(=NH)-NH-(CH₂)₃-NH-(CH₂)₃-NH-(CH₂)₃-NH-C(=NH)-NH-CH₃ · 4 HBr
B179-1

Structure: (CH₃)(CH₃N=)C-NH-(CH₂)₃-NH-(CH₂)₃-NH-(CH₂)₃-NH-C(=NCH₃)(NHCH₃) · 4 HBr
B182

Structure: CH₃CH₂-S-CH₂CH₂-NH-(CH₂)₃-NH-(CH₂)₃-NH-(CH₂)₃-NH-CH₂CH₂-S-CH₂CH₃ · 4 HBr
49-TDW-15

TABLE A-continued

| Compound |
|---|

(structure) · 4 HBr
49-TDW-17C (structure) · 4 HBr
49-TDW-29C (structure) · 2 HF
44-DHEJ-41

(structure) · 4 HF
44-DHEJ-41C (structure) · 4 HF
51-DHEJ-15C (structure) · 2 HF
51-DHEJ-16

(structure) · 4 HBr
51-DHEJ-2

(structure) · 4 HBr
51-DHEJ-2C (structure) · 4 HF
50-DHEJ-3C (structure) · 4 HBr
49-TDW-31

TABLE A-continued

Compound

51-DHEJ-19 · 4 HBr

51-DHEJ-18 · 4 HBr

51-DHEJ-20 · 2 CF₃COOH

53-SV-3C
R-IPENSpm · 4 HBr

YZ3604C
S-IPENSpm · 4 HBr

53-SV-2C · 4 HBr

49-TDW-34 · 4 HBr

B275 · 4 HBr

B291 · 4 HBr

B283-1 · 4 HBr

TABLE A-continued
Compound
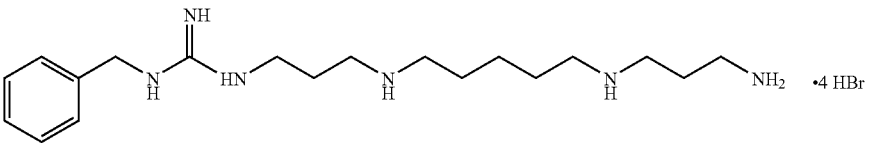
B283-2
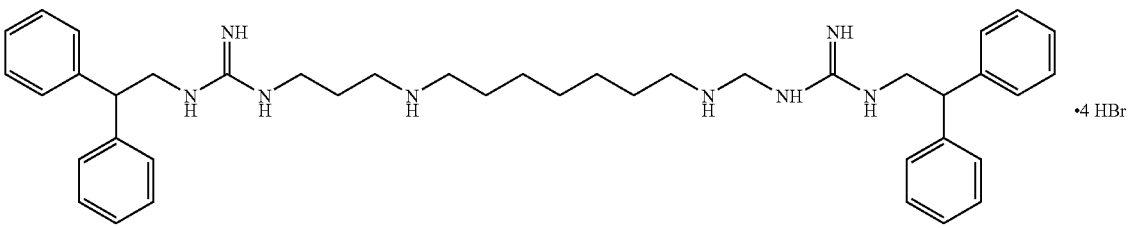
B300
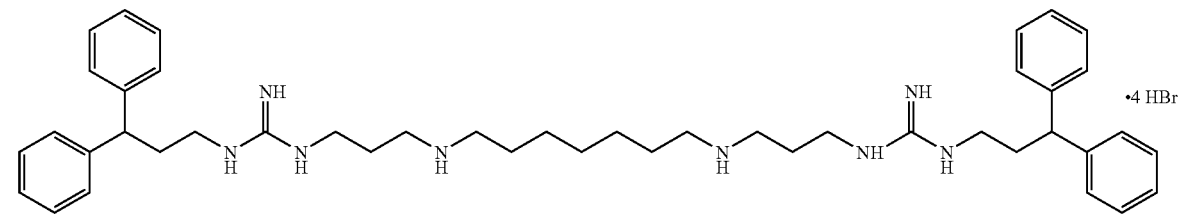
B301
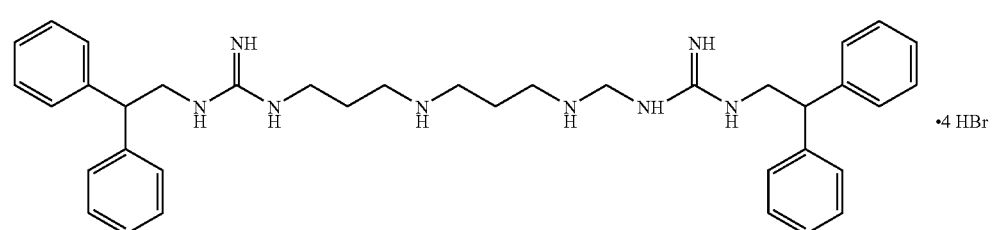
B298
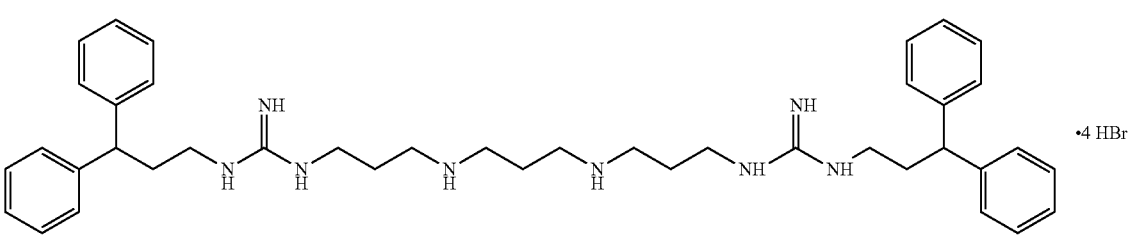
B299
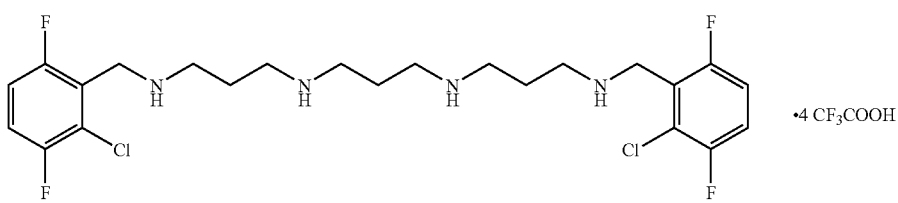
51-DHEJ-38C TABLE A-continued
Compound
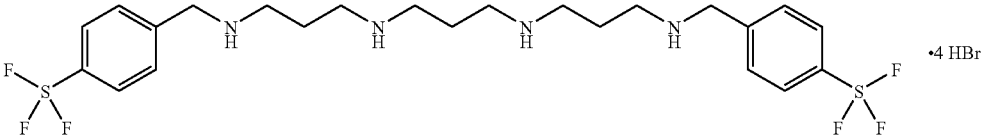
51-DHEJ-45
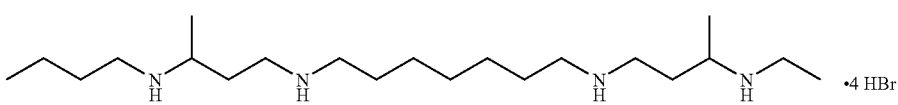
51-DHEJ-49C
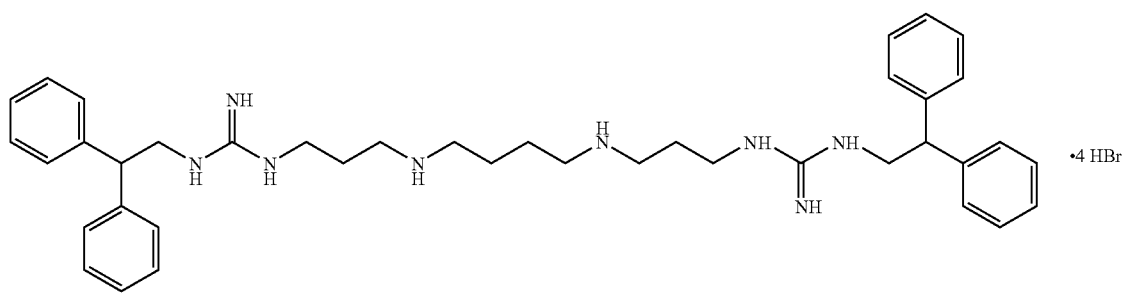
XBI-54-9B
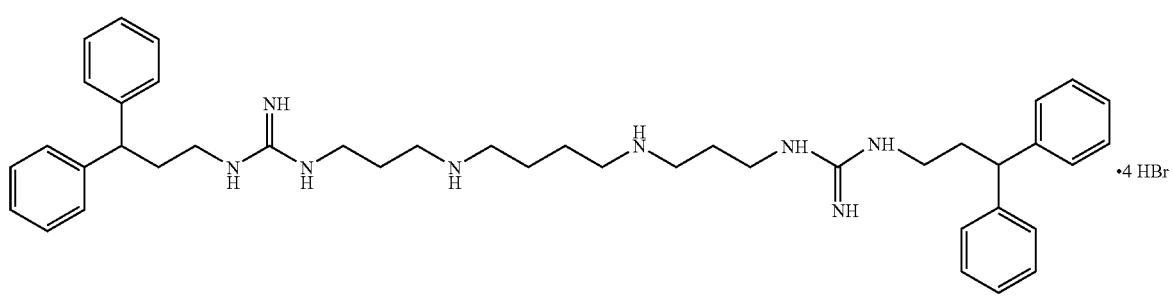
XBI-54-8B
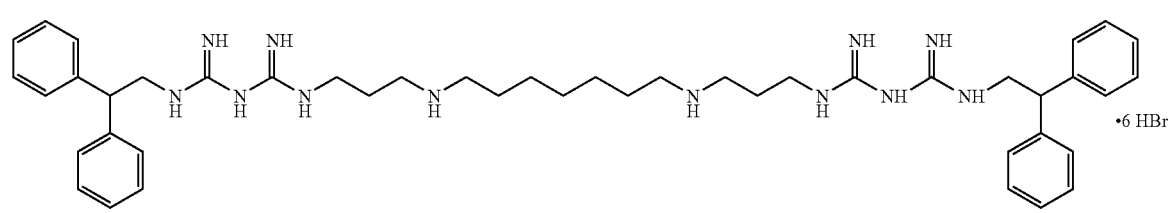
XBI-54-11C
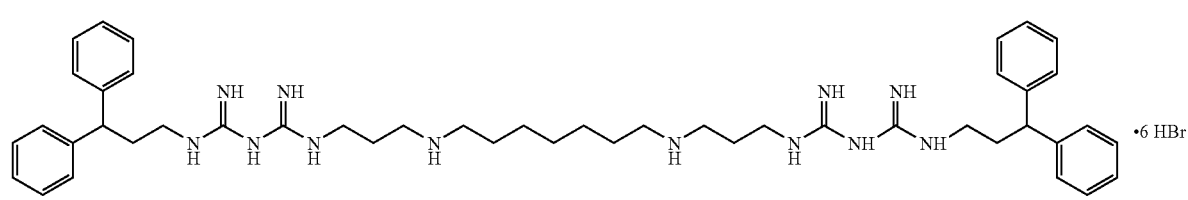
XBI-54-13B TABLE A-continued Compound XBI-54-12C · 6 HBr XBI-54-12D · 6 HBr XBI-54-14B · 6 HBr XBI-54-13D · 6 HBr

55-DHEJ-7C · 4 CF$_3$COOH

51-DHEJ-8 · 4 CF$_3$COOH

TABLE A-continued
Compound
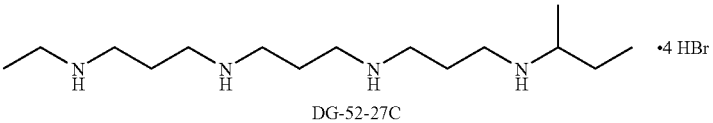
DG-52-27C  •4 HBr
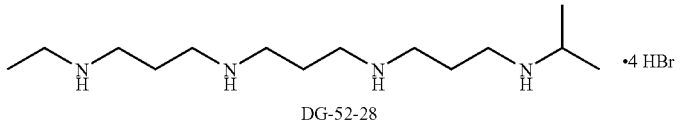
DG-52-28  •4 HBr
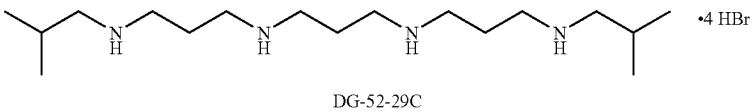
DG-52-29C  •4 HBr
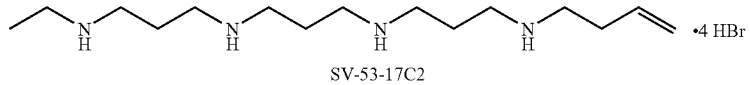
SV-53-17C2  •4 HBr
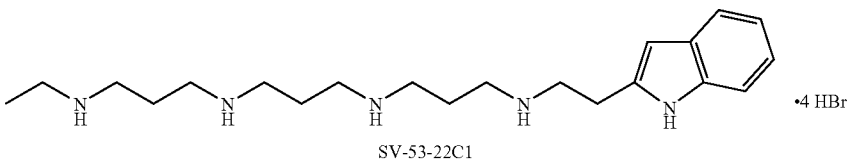
SV-53-22C1  •4 HBr
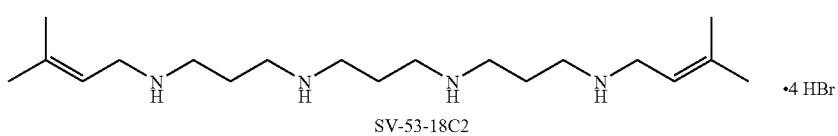
SV-53-18C2  •4 HBr
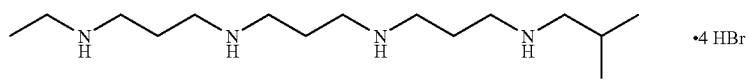
DG-52-30C  •4 HBr
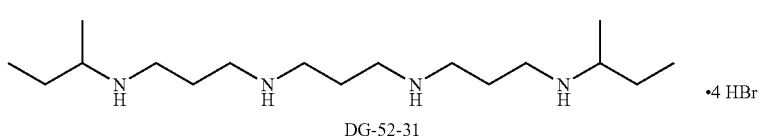
DG-52-31  •4 HBr
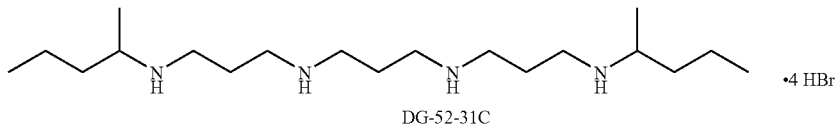
DG-52-31C  •4 HBr
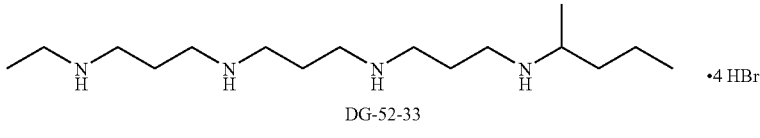
DG-52-33  •4 HBr
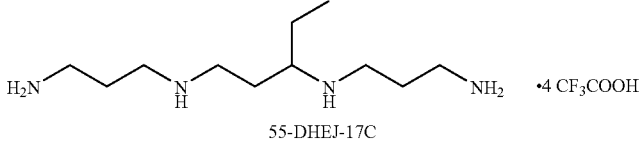
55-DHEJ-17C  •4 CF$_3$COOH TABLE A-continued
Compound
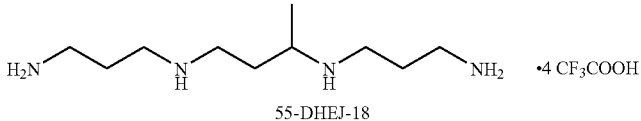
55-DHEJ-18 · 4 CF$_3$COOH
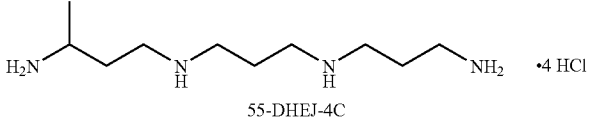
55-DHEJ-4C · 4 HCl
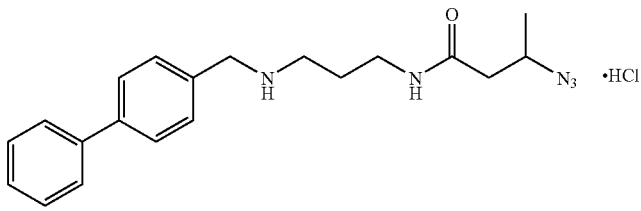
55-DHEJ-15C · HCl
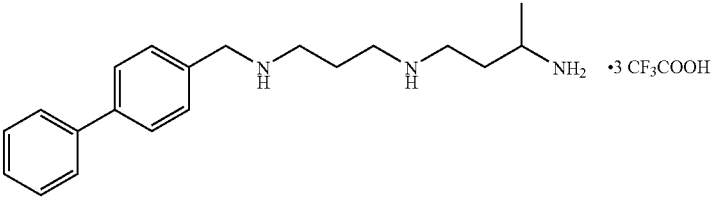
55-DHEJ-26 · 3 CF$_3$COOH
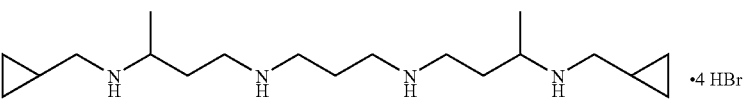
55-DHEJ-35C · 4 HBr
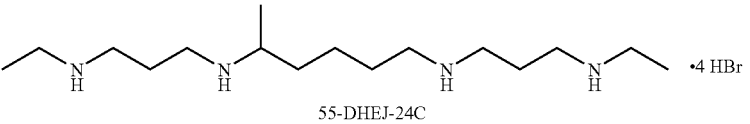
55-DHEJ-24C · 4 HBr
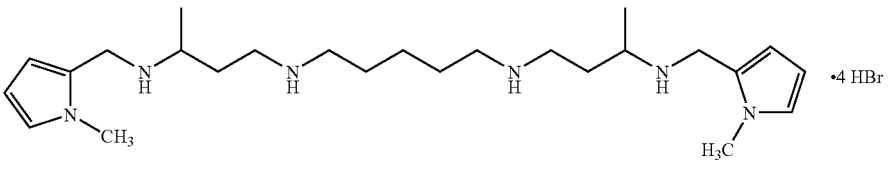
55-DHEJ-34C · 4 HBr
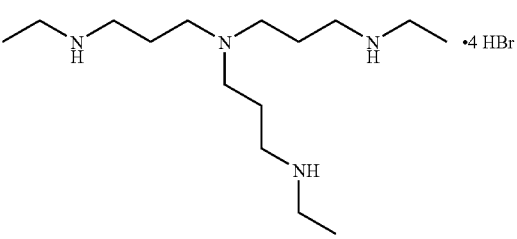
55-DHEJ-31C · 4 HBr TABLE A-continued Compound

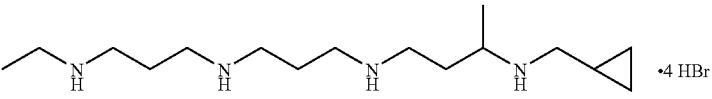

55-DHEJ-37C · 4 HBr

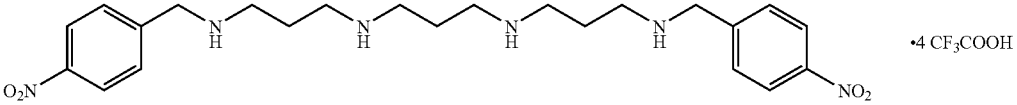

55-DHEJ-40 · 4 CF$_3$COOH

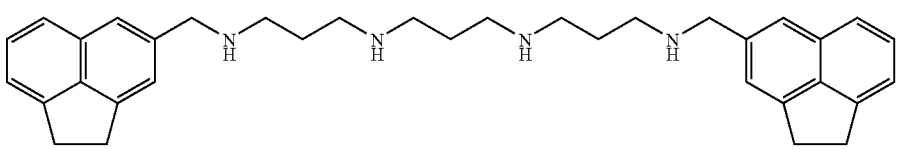

55-DHEJ-40C · 4 CF$_3$COOH

Synthetic Methods—Synthesis of Alkylpolyamines

Several synthetic methods are available for synthesis of polyamine analog compounds, including both symmetrically-substituted and asymmetrically-substituted polyamine analogs. Some of these methods are described in the following publications: Saab et al., J. Med. Chem. 36:2998 (1993); Bellevue et al., Bioorg. Med. Chem. Lett. 6:2765 (1996); Sirisoma et al., Tetrahedron Lett. 39:1489 (1998); Zou et al., Bioorg. Med. Chem. Lett. 11:1613 (2001), and Casero et al., J. Med. Chem. 44:1 (2001).

asymmetrically substituted alkylpolyamine. Treatment of 8 with 2.2 equivalents of alkyl halide in the presence of NaH and DMF affords the bis-substituted intermediate 10, which upon deprotection yields the corresponding symmetrically substituted alkylpolyamine. Thus three distinct alkylpolyamines can be readily synthesized from a single intermediate, and the central carbon chain can be made in any desired length (n=0-8). Synthesis of the intermediate 8 is readily accomplished in large quantities using previously reported synthetic strategies (Bellevue et al., Bioorg. Med.

Scheme 1. "Mest" indicates mesitylene sulfonyl (2,4,6-trimethylbenzene-1-sulfonyl) moiety.

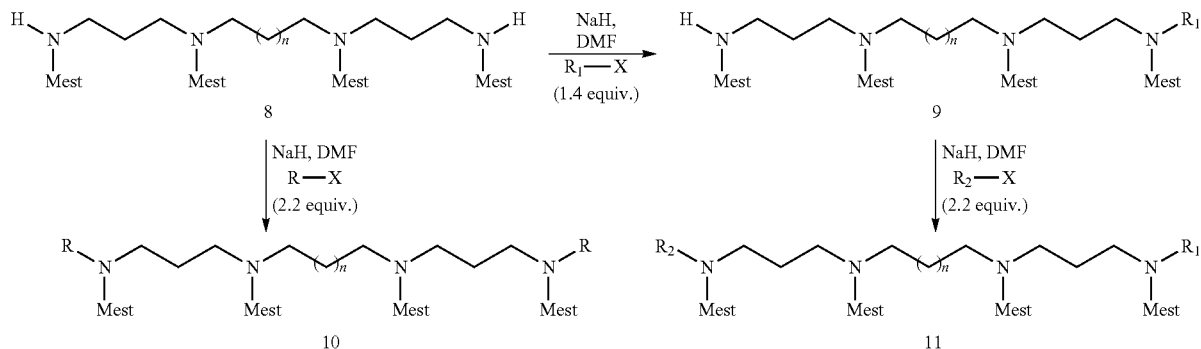

Scheme 1 illustrates a useful pathway to various polyamine analogs. The tetramesitylated intermediate 8 can be readily alkylated at both terminal nitrogens, since the hydrogens on these nitrogens are rendered acidic by the adjacent mesityl protecting group. Alkylation in the presence of 1.2 to 1.4 equivalents of alkyl halide or tosylate affords primarily the monosubstituted product 9, and disubstituted materials and unreacted starting material can then be separated and recycled (Bellevue et al., Bioorg. Med. Chem. Lett. 6:2765 (1996); Zou et al., Bioorg. Med. Chem. Lett. 11:1613 (2001)). The resulting monoalkylated derivative 9 can then be deprotected (30% HBr in AcOH), or realkylated with a different alkyl halide to provide the asymmetrically substituted intermediate 11. Deprotection of 11 then provides the desired Chem. Lett. 6:2765 (1996); Zou et al., Bioorg. Med. Chem. Lett. 11:1613 (2001)). A similar strategy can be used to access spermidine-like analogs of the form:

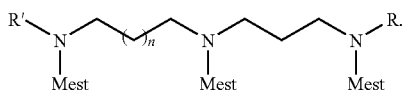

Other methods can be used for synthesis of the requisite polyamine backbone structures, which involve carbon nitrogen bond formation and selective nitrogen protection; some of these procedures are shown in Scheme 2.

Scheme 2

Method A

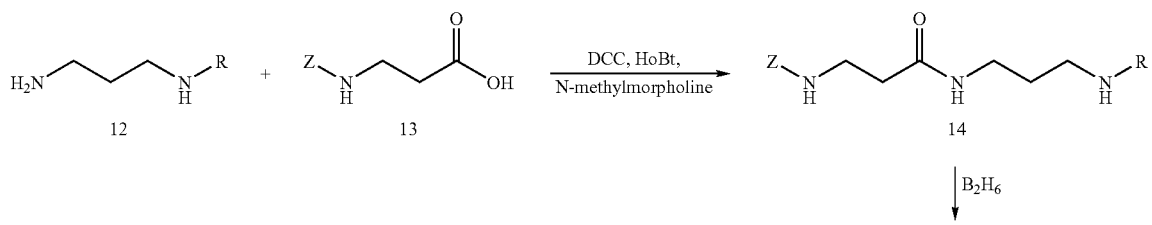

Method B

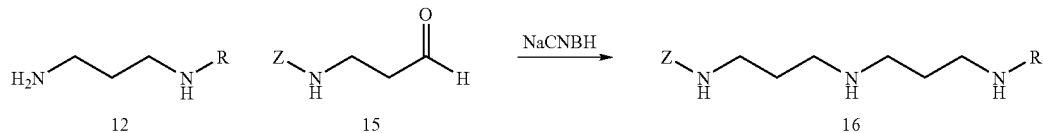

Method C

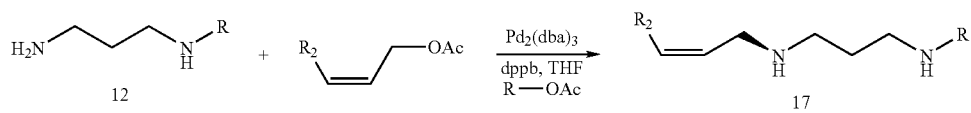

R = protected alkylamino chain
R₂= allylic alkyl group
Z = nitrogen protecting group Aminopropyl (or other aminoalkyl) moieties can be added to selectively protected primary amines such as 12 by standard peptide coupling techniques (Method A, Woster et al., J. Med. Chem. 32:1300 (1989)). Thus treatment of 12 with the protected beta-aminopropionate 13 (DCC, HoBt, N-methylmorpholine) affords the corresponding amide 14, which is then reduced in the presence of diborane (Woster et al., 1989) to afford the desired secondary amine 16. Compound 16 may be synthesized directly by reductive amination (Method B), in which the appropriate aldehyde 15 is added to 12 in the presence of sodium cyanoborohydride. Alkyl substituents that contain an allylic acetate functionality can also be appended to 12 using a palladium catalyzed coupling reaction that proceeds with retention of configuration (Method C, Sirisoma et al., Tetrahedron Lett. 39:1489 (1998)). This method can also be used to introduce phthalimide or benzylamine to an allylic acetate site as a synthetic equivalent for nitrogen. These nitrogens can then be deprotected and functionalized.

Synthetic Methods—Synthesis of Polyaminoguanidines

Scheme 3

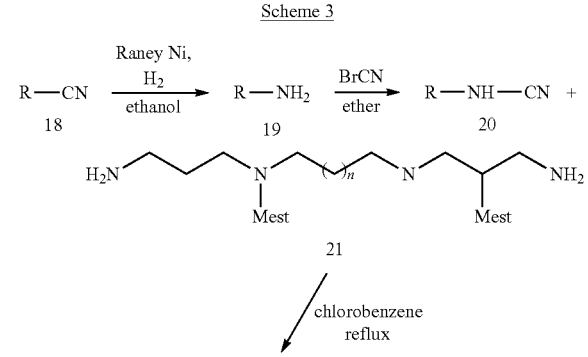

-continued

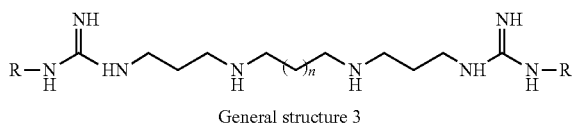

General structure 3

Synthesis of polyaminoguanidines can be carried out as outlined in Scheme 3. The requisite amine 19 (produced when necessary from the corresponding alkyl or aralkylcyanide) is reacted with cyanogen bromide (Goldin et al., U.S. Pat. No. 6,288,123 (2001)) to afford the corresponding aminocyanogen 20. When the desired amine is not commercially available, it can be prepared from the appropriate cyano compound by catalytic reduction (Bellevue et al., 1996, Zou et al., 2001). Intermediate 21 (Bellevue et al., 1996; Zou et al., 2001) is then coupled to 20 (chlorobenzene, reflux), followed by deprotection (30% Hbr in AcOH) to produce alkylpolyaminoguanidines of general structure 3. Using these methods, substituted polyaminoguanidine analogs (e.g., R═H, methyl, ethyl, cyclopropylmethylene, cycloheptylmethylene, phenyl, benzyl) can be synthesized. An analogous route (not shown) utilizing the N-Boc protection group was also employed.

Synthetic Methods—Synthesis of Polyaminobiguanides

The synthesis of polyaminobiguanides is described in Bi et al., Bioorg. Med. Chem. Lett. 16:3229 (2006), and is also outlined in Scheme 4.

Scheme 4

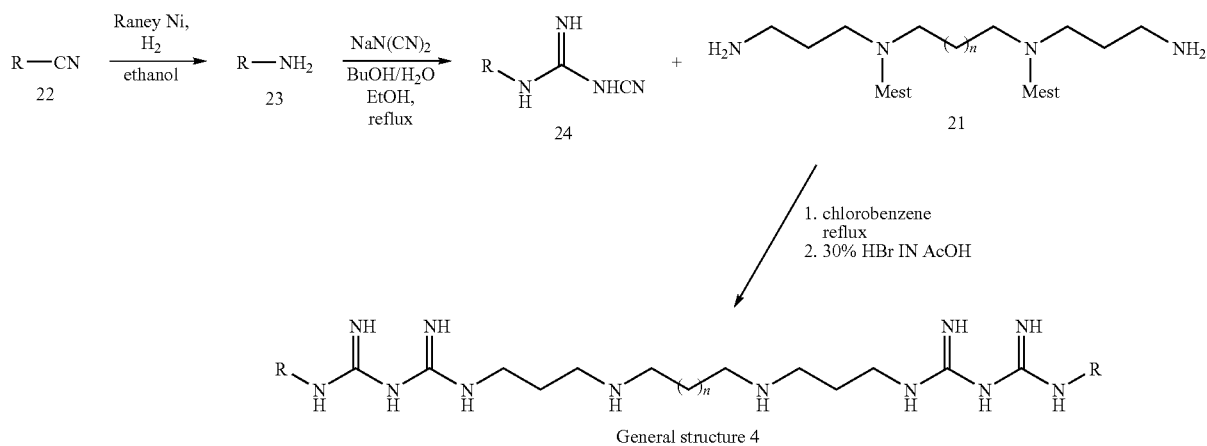

A similar strategy is employed for the synthesis of alkylpolyaminobiguanides of general structure 4, as outlined in Scheme 4. Amines 23 (produced when necessary from the corresponding alkyl or aralkylcyanide) are converted to the corresponding cyanoguanidines 24 (NaN(CN)$_2$, BuOH/H$_2$O) (Gerhard, R.; Heinz, B.; Herbert, F. *J. Praktische Chem.* (*Leipzig*), 1964, 26, 414-418), which were combined with 21 as previously described to afford the mesityl protected target molecules. Deprotection as described above then provided the substituted biguanides 4. An analogous route (not shown) utilizing the N-Boc protection group was also employed, as above.

Synthetic Methods—Solid Phase Synthesis

Scheme 4

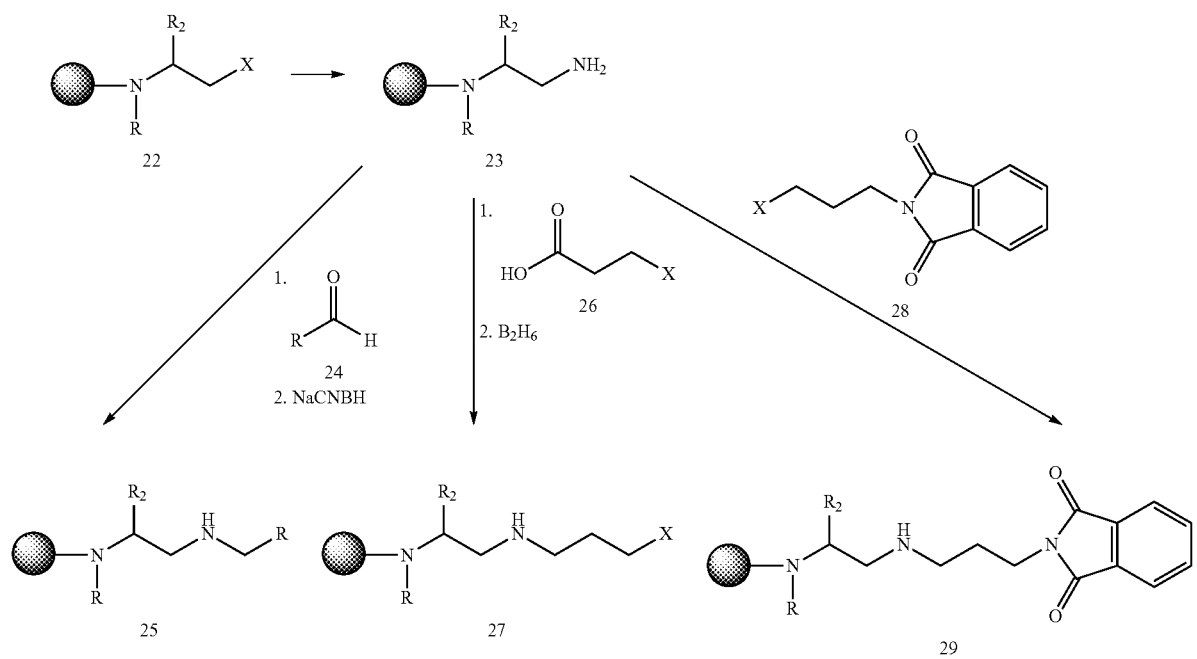

Solid phase synthetic techniques can be used for the rapid and efficient synthesis of both alkylpolyamines and their alpha-methyl homologs, as shown in Scheme 4. Compound 22 can be produced using a commercially available trityl chloride resin, as described in Wang et al., J. Am. Chem. Soc., 95(4):1328 (1973), where the attached amine is primary or secondary prior to attachment, an alpha-methyl is present or absent, and the X group is either a protected amine or a synthetic equivalent such as an azide or a phthalamide. This intermediate is then deprotected or converted to the corresponding primary amine 23. Three strategies can be used for chain elongation: 1. reductive amination with aldehydes 24 in the presence of sodium cyanoborohydride to produce 25; 2. addition of an appropriate carboxylate 26 under peptide coupling conditions (Woster et al., J. Med. Chem. 32:1300 (1989)), followed by diborane reduction of the resulting amide, yielding 27; 3. direct alkylation with a protected halide (Woster et al., J. Med. Chem. 32:1300 (1989)) such as 28, to afford intermediates 29. Repetition of these steps then allows the synthesis of a variety of alkylpolyamines and alpha-methyl-alkylpolyamines with substituents as desired.

Biological Applications—Lysine-Specific Demethylase-1 (LSD1) Inhibitors

Histones are proteins found in eukaryotic cells which act as support scaffolds for DNA (sometimes compared to a protein spool supporting the DNA thread). Histones, together with other proteins and DNA, form the chromatin of the cell nucleus. Because of their close association with DNA, histones play a role in gene regulation. The tails of histone proteins are a frequent site for covalent modifications which affect gene expression.

The enzyme lysine-specific demethylase-1 (LSD1; also known as BHC110 and KIAA0601) is an enzyme that affects the covalent modification of histone tails, by demethylating lysine 4 of the histone H3. Shi et al. (Cell, 119:941 (2004)) showed that RNAi inhibition of LSD1 led to an increase in H3 lysine 4 methylation, followed by de-repression of the target genes. Thus LSD1 apparently represses transcription by demethylating histone H3. Conversely, inhibition of LSD1 allows transcription by preventing demethylation.

Because of the observed homology between the active site of LSD1 and monoamine oxidase (MAO), Lee et al. (Chemistry & Biology 13:563 (2006)) tested various MAO inhibitors for their ability to inhibit LSD1. They identified tranylcypromine ((1R,2S)-2-phenylcyclopropan-1-amine) as an inhibitor with an $IC_{50}$ less than 2 micromolar. Treating P19 embryonal carcinoma cells with tranylcypromine led to transcriptional de-repression of the Egr1 and Oct4 genes.

International Patent Application WO 2006/071608 is directed to a method for monitoring eukaryotic histone demethylase activity, methods for up-regulating and down-regulating methylated histone-activated genes, and a method for treating or preventing a disease (e.g., a hyperproliferative disease such as cancer) by modulating the level of protein or the activity of a histone demethylase.

In view of the importance of gene regulation, and the ability to affect gene regulation by inhibiting or modulating LSD1, inhibitors of the enzyme may have significant therapeutic potential. Table B shows compounds tested for LSD1 inhibitory activity While the compounds are depicted as free bases, it is to be understood that the disclosure in the table embraces all salts, hydrates, and solvates of the compounds depicted therein, as well as the non-salt, non-hydrate/non-solvate form of the compound, as is well understood by the skilled artisan. Several of the polyamine, polyamine/guanidine, and polyamine/biguanide compounds disclosed herein have activity as LSD1 inhibitors. FIG. 24, FIG. 25, FIG. 26, FIG. 27, FIG. 28, FIG. 29, FIG. 30, FIG. 31, FIG. 32, and FIG. 33 show the effects of some of the compounds disclosed herein on LSD1 activity. The compounds disclosed herein, including the compounds of formulas (I) through (IX), the compounds of Table A, and the compounds of Table B, are useful as inhibitors of LSD1. More specifically, polyamine/guanidine and polyamine/biguanide compounds are useful as inhibitors of LSD1, such as the compounds of formulas (I) and (II). The enzyme can be inhibited by at least about 25%, at a concentration of the compound of about 10 micromolar or less, about 1 micromolar or less, about 100 nanomolar or less, about 10 nanomolar or less, or about 1 nanomolar or less; by at least about 50%, at a concentration of the compound of about 10 micromolar or less, about 1 micromolar or less, about 100 nanomolar or less, about 10 nanomolar or less, or about 1 nanomolar or less; at least about 75%, at a concentration of the compound of about 10 micromolar or less, about 1 micromolar or less, about 100 nanomolar or less, about 10 nanomolar or less, or about 1 nanomolar or less; at least about 90%, at a concentration of the compound of about 10 micromolar or less, about 1 micromolar or less, about 100 nanomolar or less, about 10 nanomolar or less, or about 1 nanomolar or less; at least about 95%, at a concentration of the compound of about 10 micromolar or less, about 1 micromolar or less, about 100 nanomolar or less, about 10 nanomolar or less, or about 1 nanomolar or less; or at least about 99% at a concentration of the compound of about 10 micromolar or less, about 1 micromolar or less, about 100 nanomolar or less, about 10 nanomolar or less, or about 1 nanomolar or less.

TABLE B

Compounds tested for LSD1 inhibitory activity

XBI-54-8B

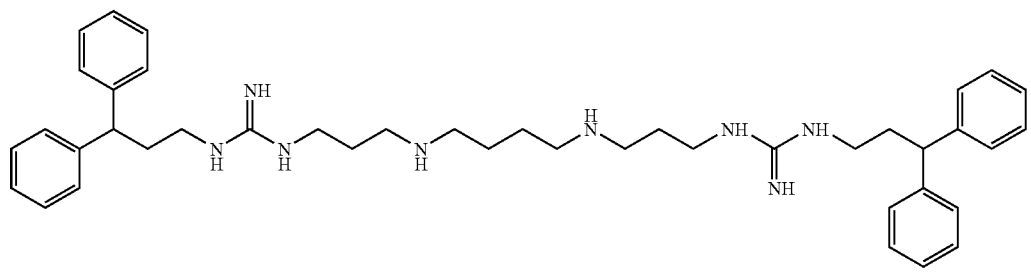

TABLE B-continued
Compounds tested for LSD1 inhibitory activity
XBI-54-9B
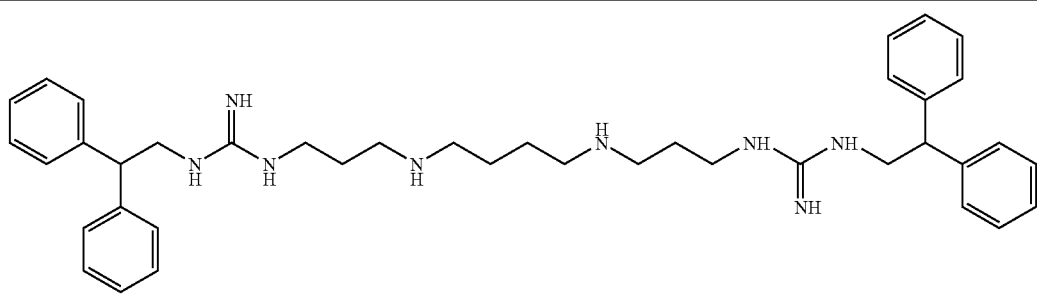
XBI-54-11C
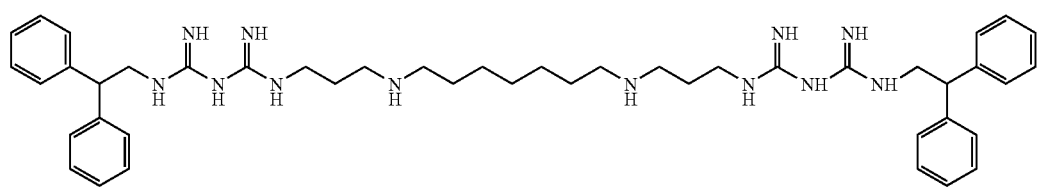
XBI-54-12C
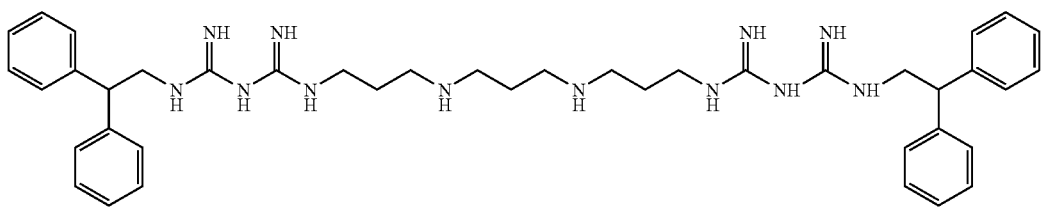
XBI-54-12D
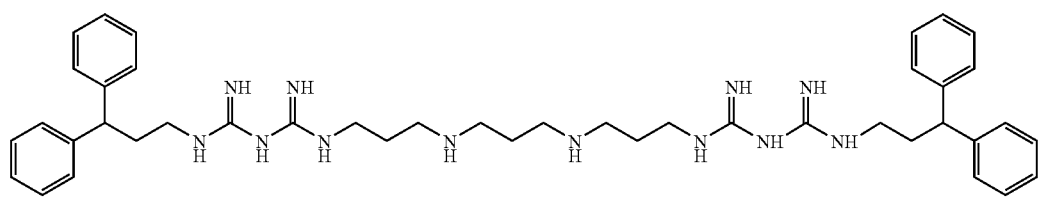
XBI-54-13B
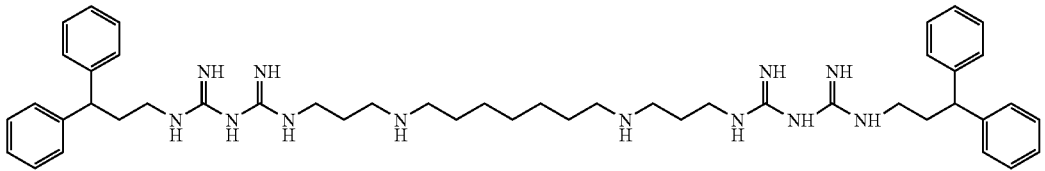
XBI-54-13D
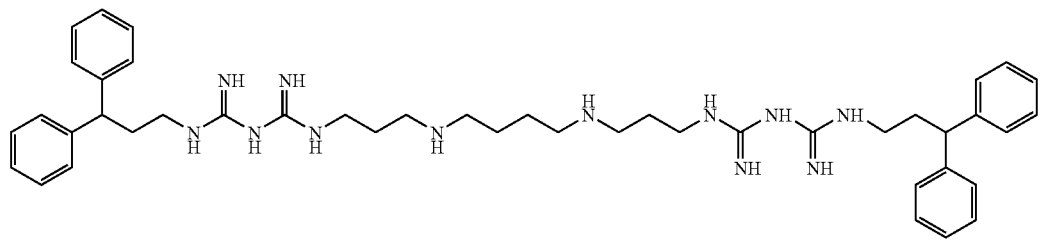
XBI-54-14B
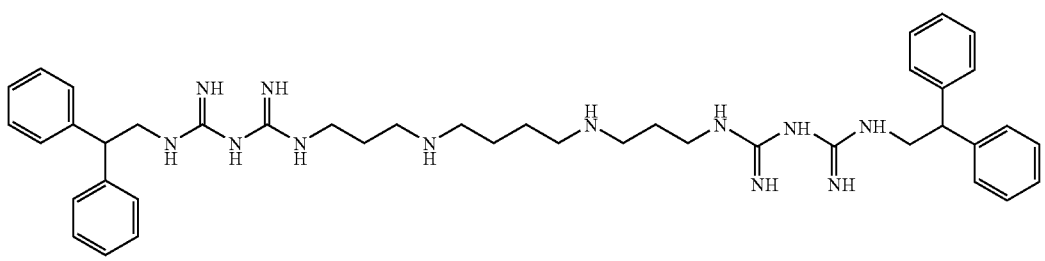

TABLE B-continued

Compounds tested for LSD1 inhibitory activity

B179-1, B181, B182, B188-2, B205-1 [chemical structures]

Biological Applications—Treatment of Cancer

Several polyamine compounds and polyamine analogs have displayed potent anticancer activity. It is believed that polyamines and polyamine analogs enter cells via the polyamine transport system and down-regulate the polyamine biosynthetic enzymes ornithine decarboxylase (ODC) and S-adenosylmethionine decarboxylase (AdoMet-DC). The antitumor activity of the bis(ethyl) polyamine analogs is thought to be due to their ability to superinduce spermidine/spermine-$N^1$-acetyltransferase (SSAT), the rate-limiting step in the polyamine back-conversion pathway. Subsequent polyamine oxidase (PAO)-mediated oxidation of the resulting acetylated polyamines then produces hydrogen peroxide which ultimately initiates the cell death program. Studies have revealed analogs that inhibit tumor cell growth through induction of SSAT, by initiating apoptosis in the presence and absence of SSAT induction, and by interference with tubulin depolymerization. Recent data suggests that human polyamine oxidase exists in two distinct forms, and that oxidation of polyamine analogues by mammalian spermidine oxidase (SMO(PAOh1) may play a role in the antitumor effects of some analogs. This hypothesis is supported by the facts that the alkylpolyamine analogues N1-ethyl-N11-[(cycloheptyl)methy]-4,8-diazaundecane (CHENSpm) is detoxified by polyamine oxidase, and that the antimicrosporidial analogue BW-1 (N,N'-bis[3-[([1,1'-biphenyl]-2-ylmethyl)amino]propyl]-1,7-heptanediamine) is substrate for the polyamine oxidase of Encephalitoozoon cuniculi. It is now evident that alkylpolyamines can effect tumor cell growth by a variety of known and unknown pathways.

"Treating" or "to treat" a disease using the methods of the invention is defined as administering one or more polyamines or polyamine analogs, with or without additional therapeutic agents, in order to palliate, ameliorate, stabilize, reverse, slow, delay, prevent, reduce, or eliminate either the disease or the symptoms of the disease, or to retard or stop the progression of the disease or of symptoms of the disease. "Therapeutic use" of the polyamines and polyamine analogs is defined as using one or more polyamines or polyamine analogs to treat a disease (including to prevent a disease), as defined above. A "therapeutically effective amount" is an amount sufficient to treat (including to prevent) a disease, as defined above. Prevention or suppression can be partial or total.

The compounds disclosed herein have anticancer activity, which has been demonstrated in a variety of human tumor cell types representing the major forms of lung, breast, prostate, and colon cancers. Thus the compounds disclosed herein can be used to treat cancer, including lung cancer, breast cancer, prostate cancer, and colon cancer, or to prevent cancer, including prevention of lung cancer, breast cancer, prostate cancer, and colon cancer.

Experimental Results and Protocols

MTS dose response experiments in H157, H82, and A549 cells following a 96 hr exposure with select compounds were performed. MTS is a standard colorimetric assay used for measuring metabolic activity in cells. MTS experiments were performed by CellTiter 96® AQ$_{ueuos}$ One Solution Cell Proliferation Assay from Promega Corporation. Briefly, the cells were seeded at 3000 cells/well on a 96 well tissue culture plate containing 100 ul of medium/well and allowed to attach overnight. The medium was then aspirated and replaced with 100 ul of fresh medium containing the appropriate concentration of the compound being tested and incubated for 96 hrs at 37° C. and 5% $CO_2$. Compounds are routinely tested at concentrations ranging from 0.1 micromolar to 50 micromolar. Wells not containing the test compound were present and used as a control. Following treatment, 20 ul of MTS reagent was added to each well and incubated at 37° C. for 1.5 hrs. The absorbance of each well was then measured at 490 nm and used to determine the metabolic activity of the cells in the presence of the test compound, relative to the control. IC$_{50}$ values for the test compounds were extracted based on the results.

Figure 2:
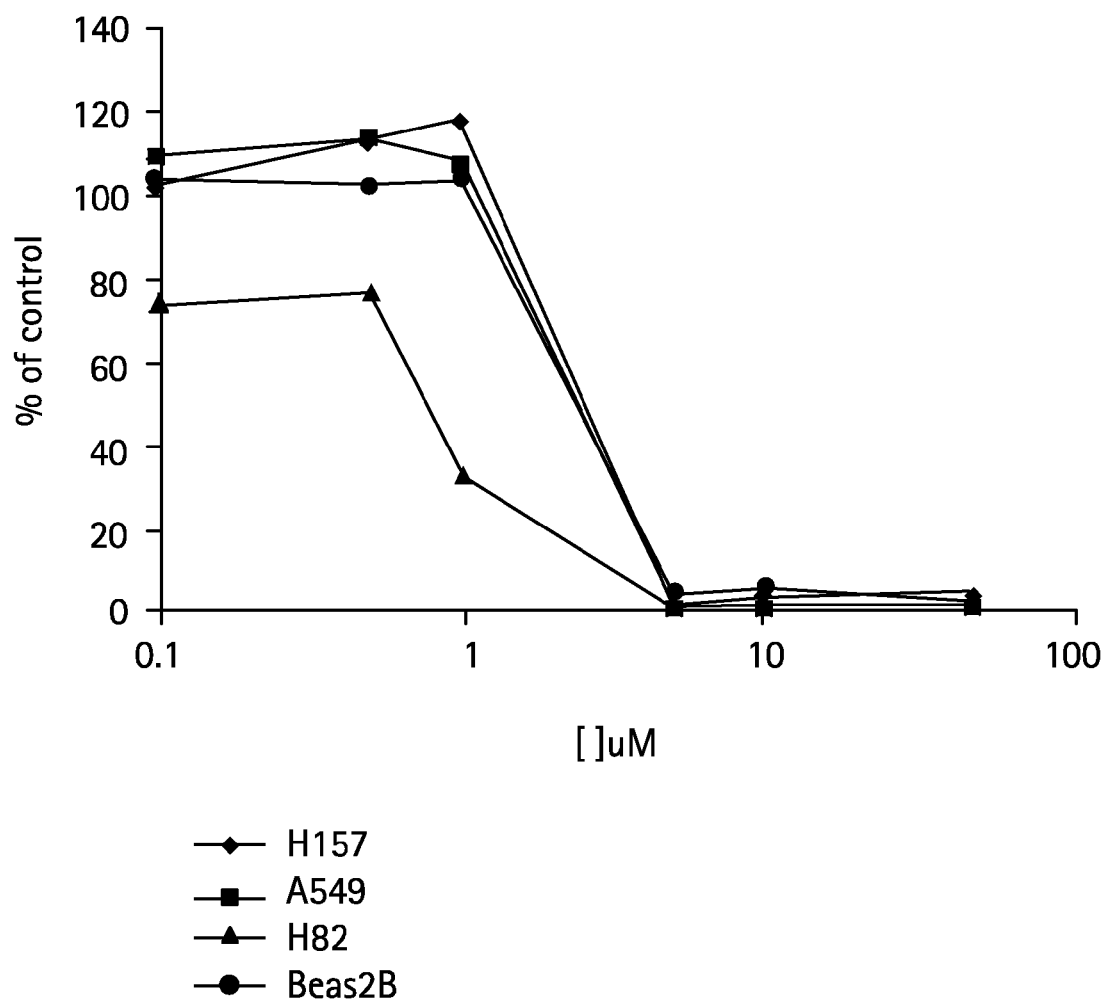
FIG. 2 depicts a 96 hr MTS dose response experiments for compound 49-TDW-9 in H157, A549, H82 and Beas2B cells.
Figure 3:
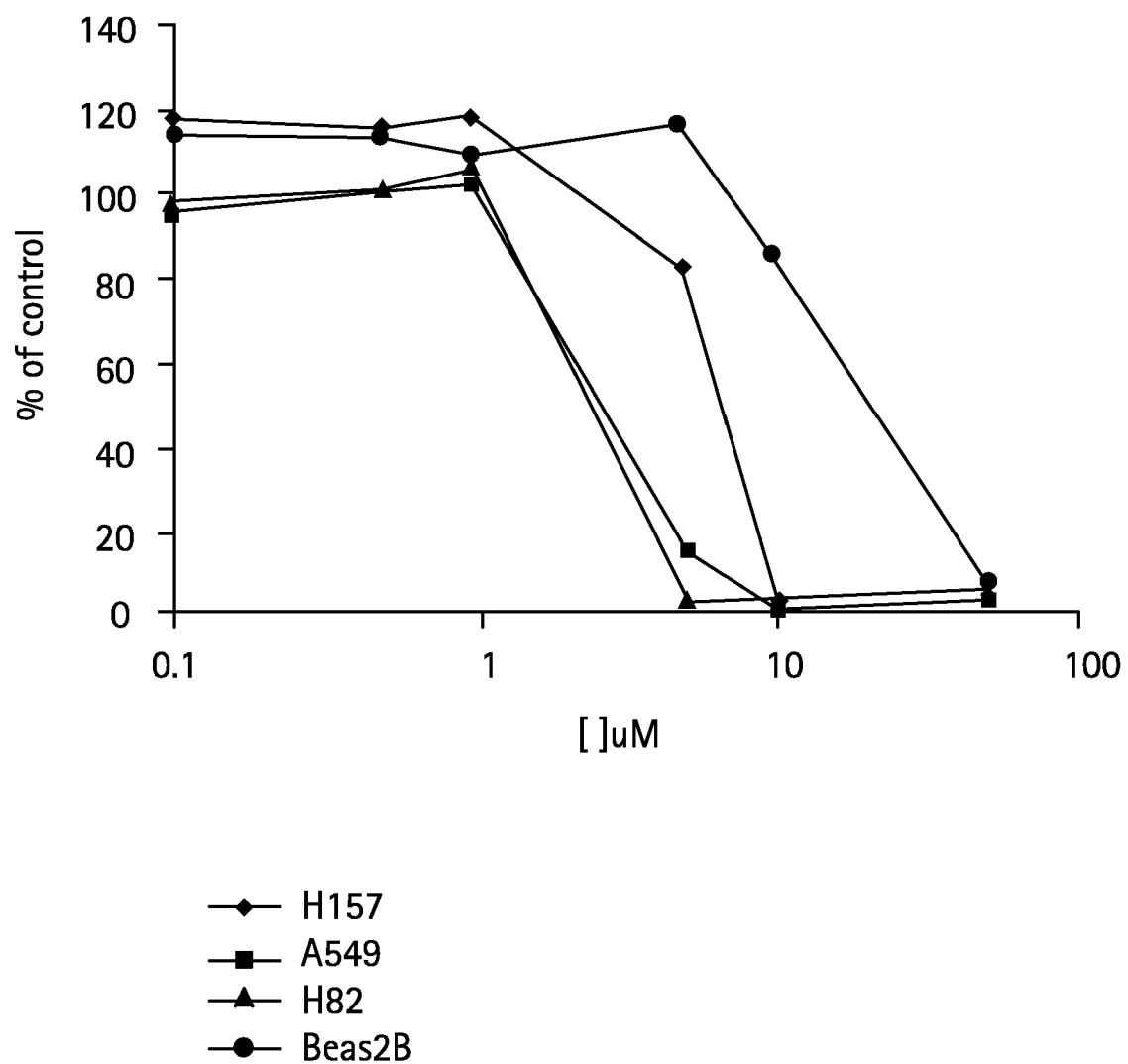
FIG. 3 depicts a 96 hr MTS dose response experiments for compound 42-TDW-21c in H157, A549, H82 and Beas2B cells.
Figure 4:
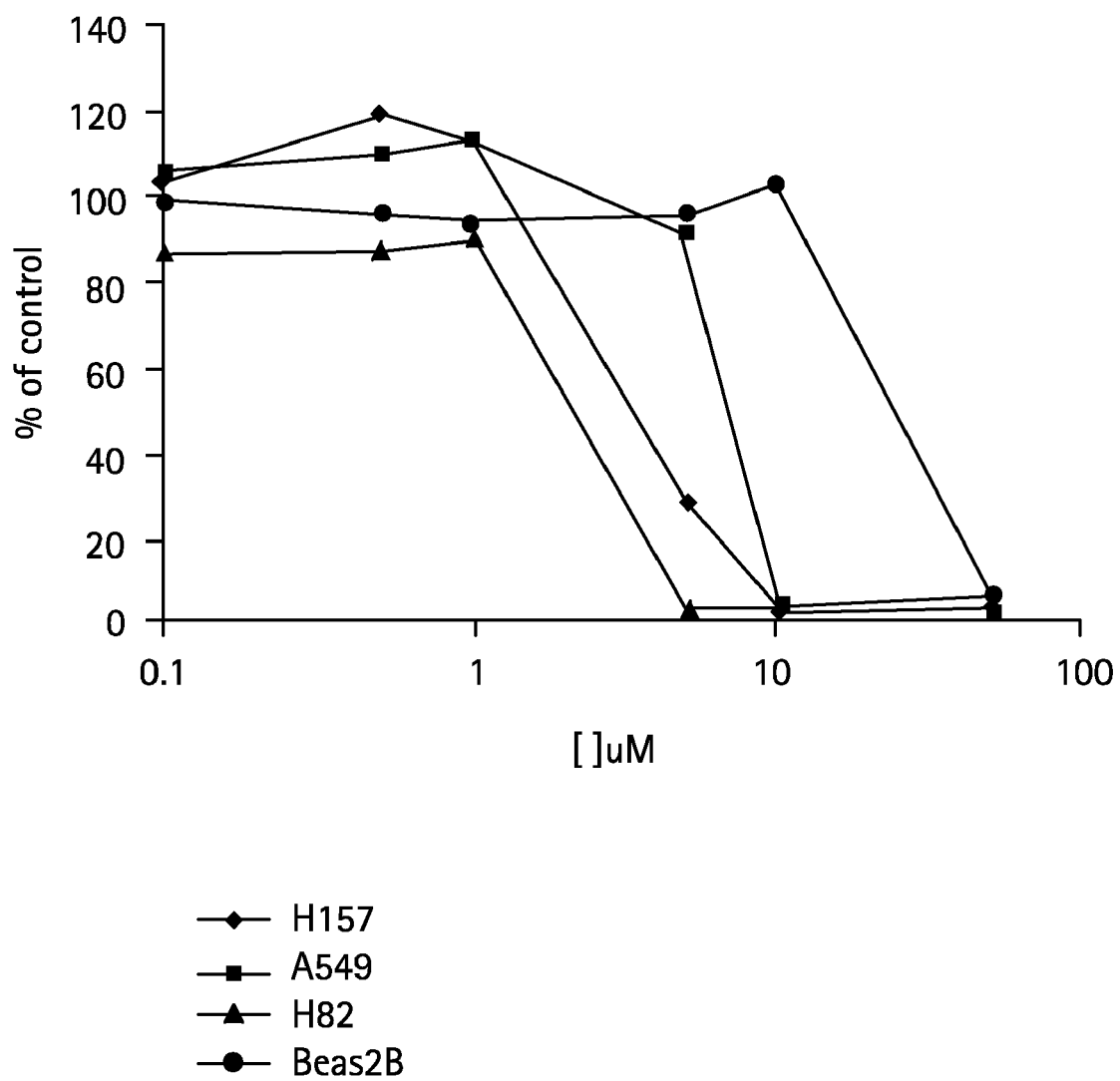
FIG. 4 depicts a 96 hr MTS dose response experiments for compound 46-TDW-19c in H157, A549, H82 and Beas2B cells.
Figure 5:
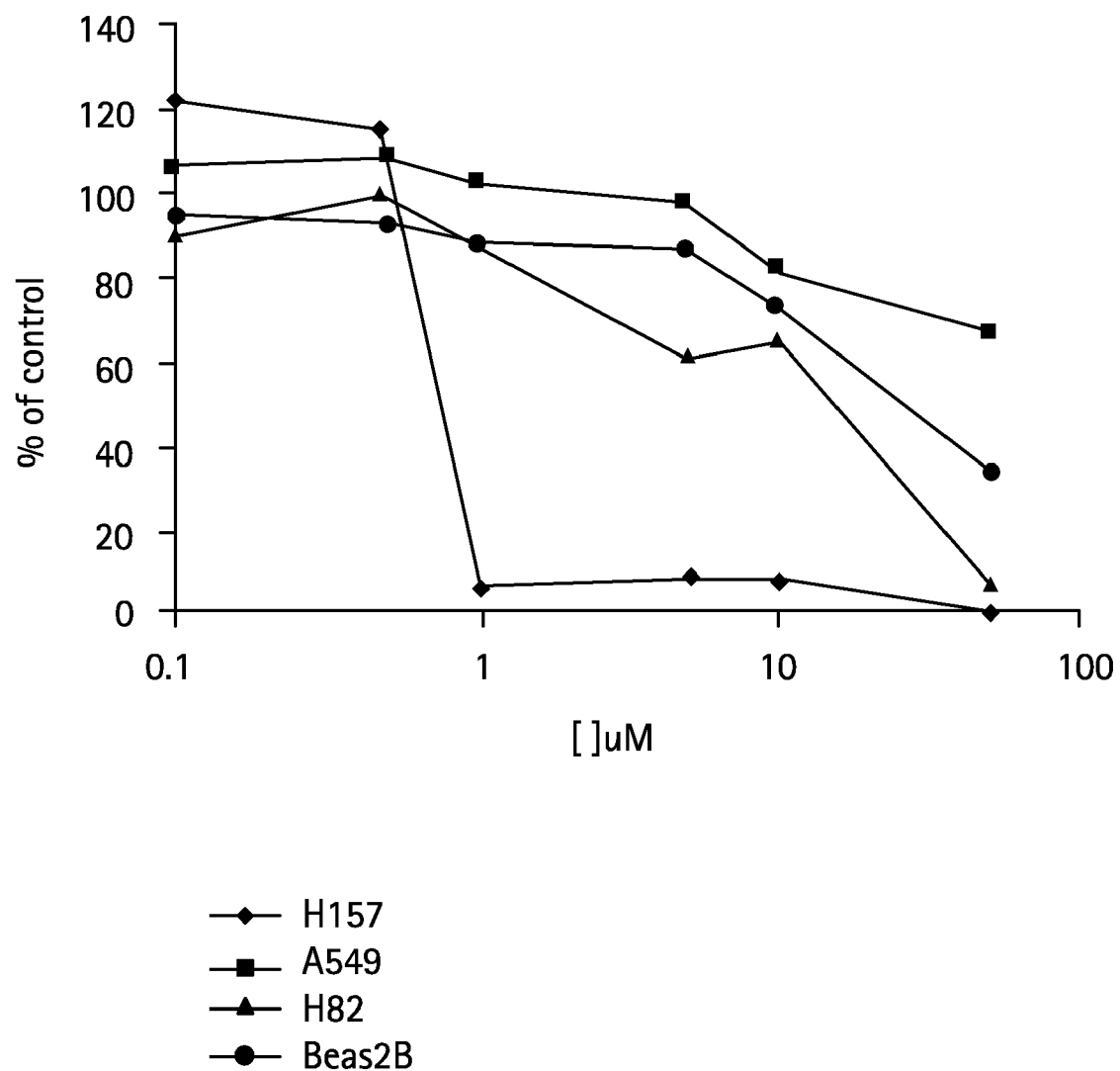
FIG. 5 depicts a 96 hr MTS dose response experiments for compound 49-TDW-17c in H157, A549, H82 and Beas2B cells.
Figure 6:
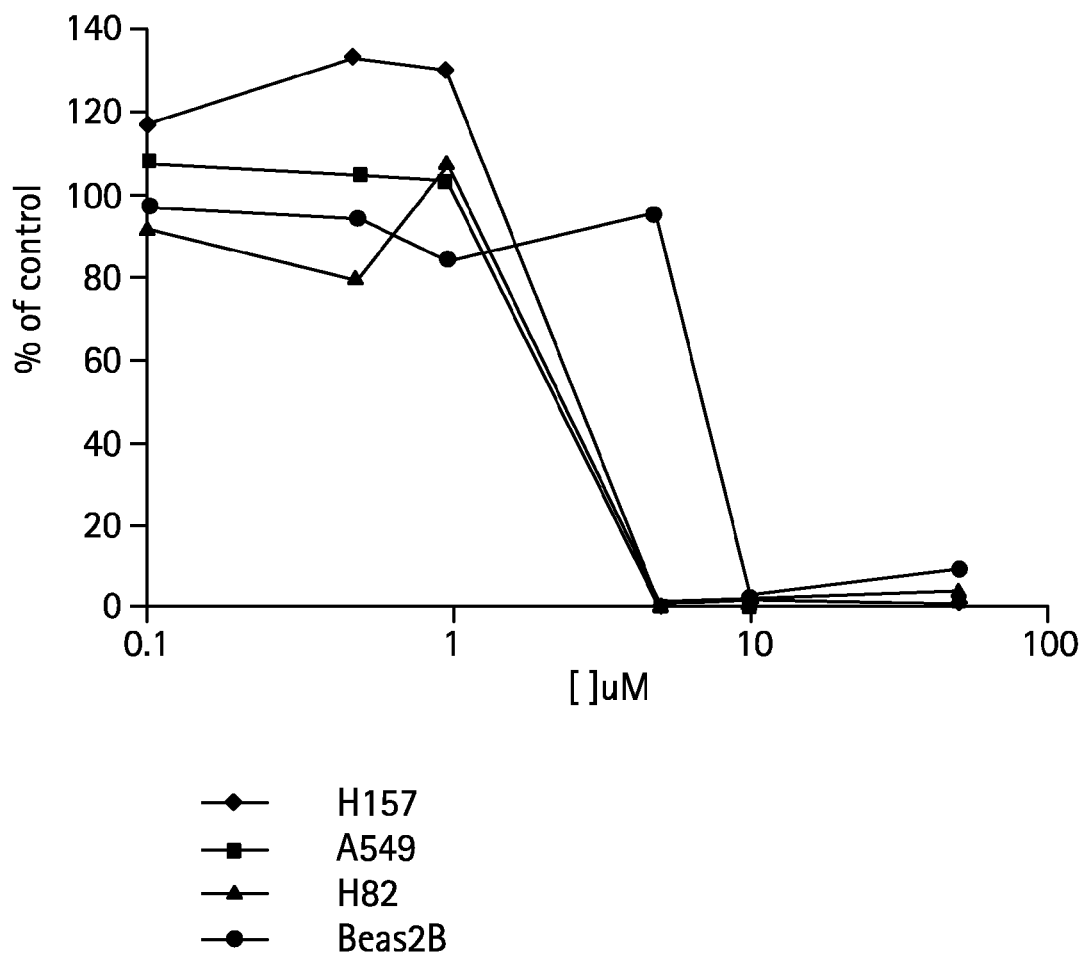
FIG. 6 depicts a 96 hr MTS dose response experiments for compound 40-TDW-37 in H157, A549, H82 and Beas2B cells.
Figure 7:
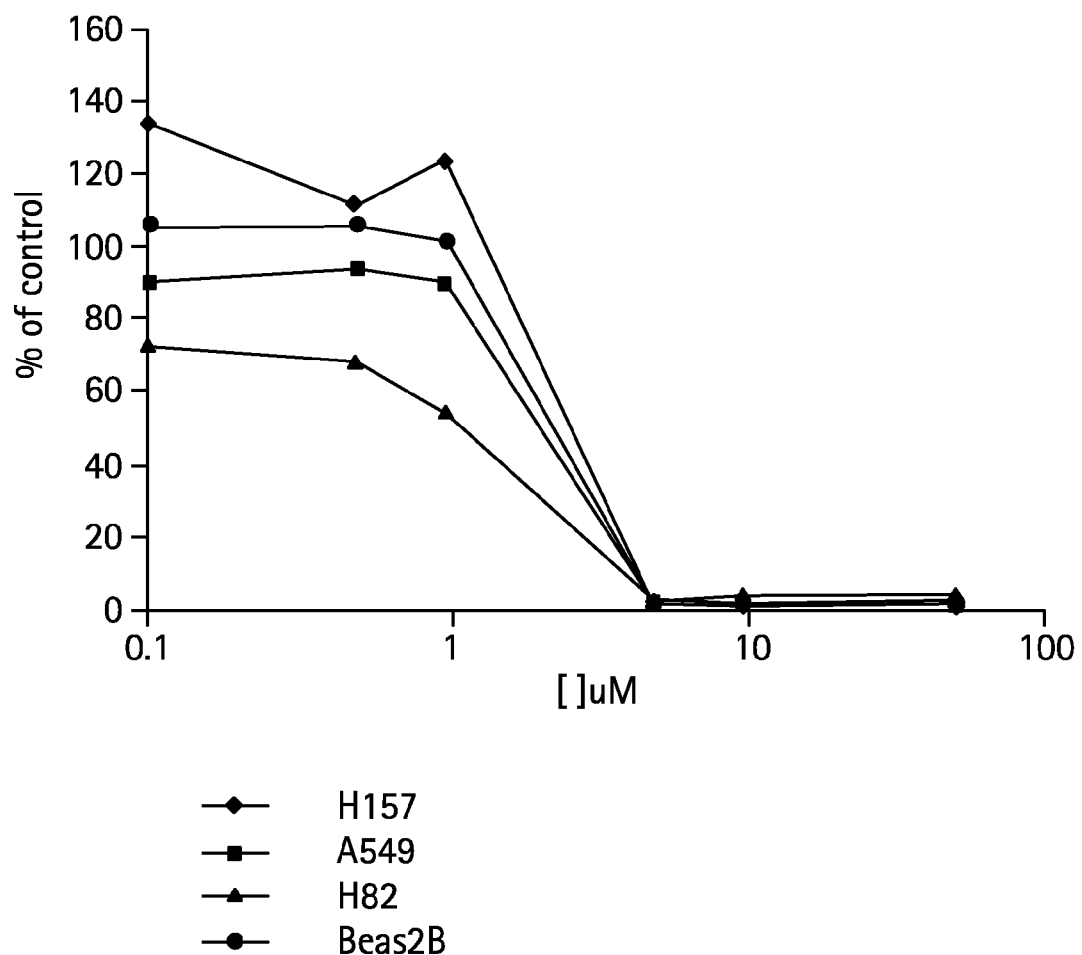
FIG. 7 depicts a 96 hr MTS dose response experiments for compound 42-TDW-4 in H157, A549, H82 and Beas2B cells.
Figure 8:
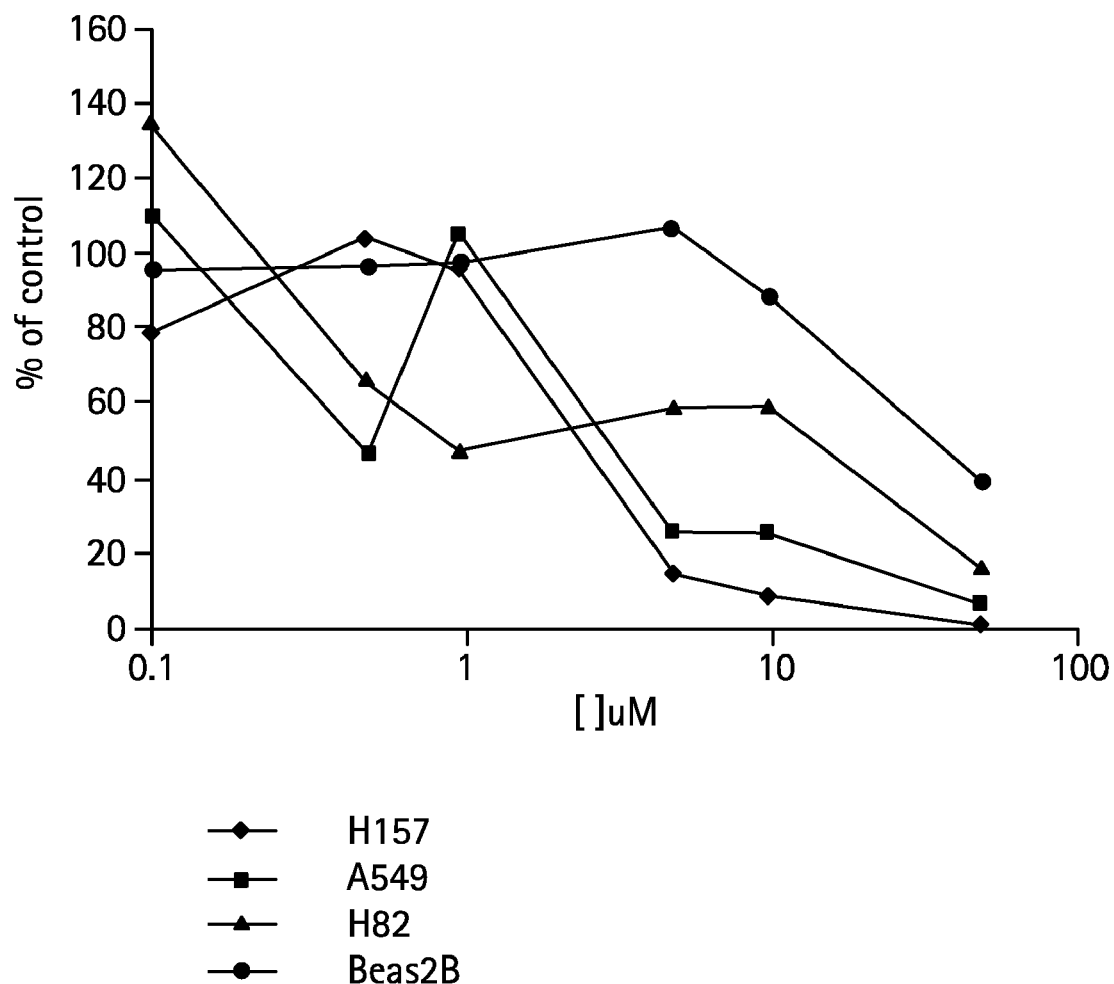
FIG. 8 depicts a 96 hr MTS dose response experiments for compound 49-TDW-29c in H157, A549, H82 and Beas2B cells.
Figure 9:
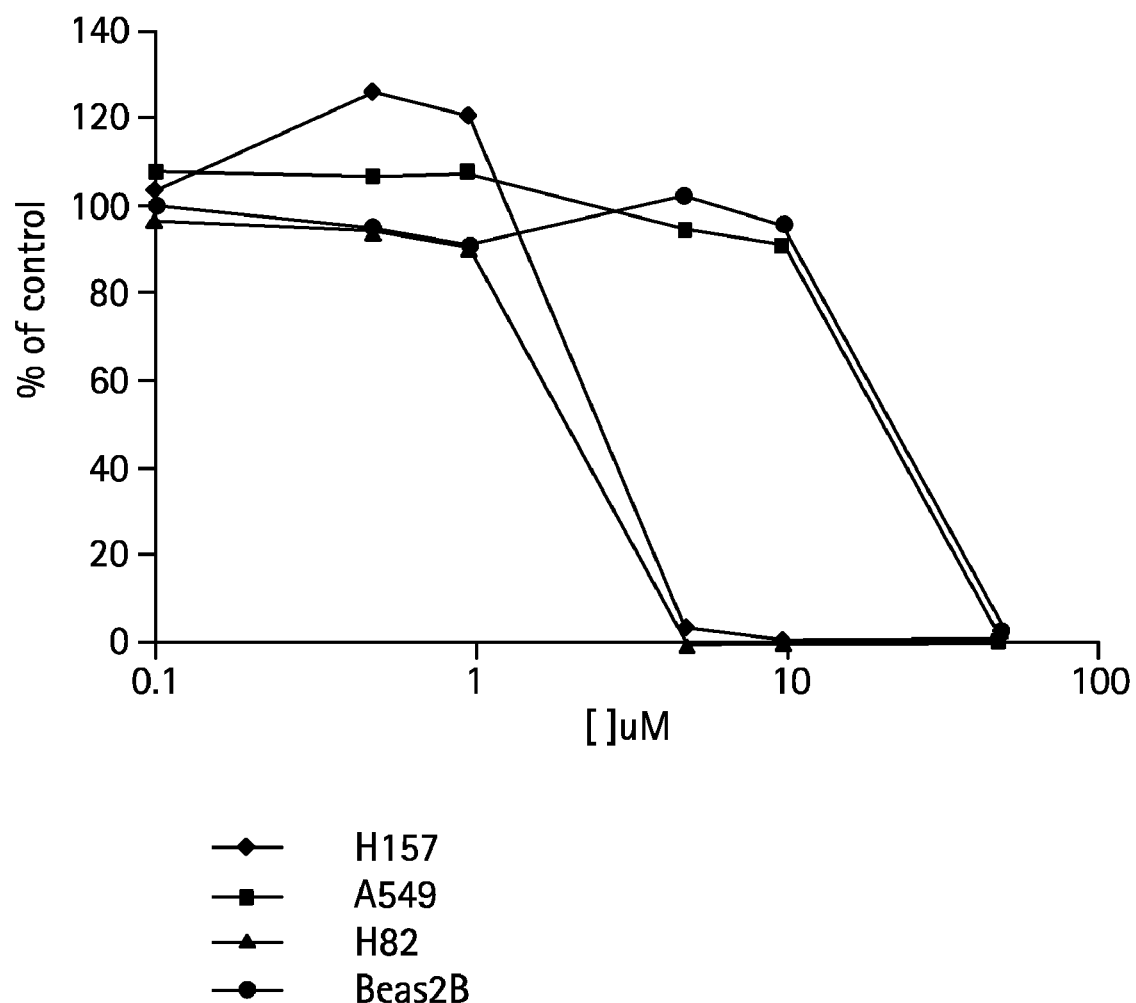
FIG. 9 depicts a 96 hr MTS dose response experiments for compound 49-TDW-32c in H157, A549, H82 and Beas2B cells.
Figure 10:
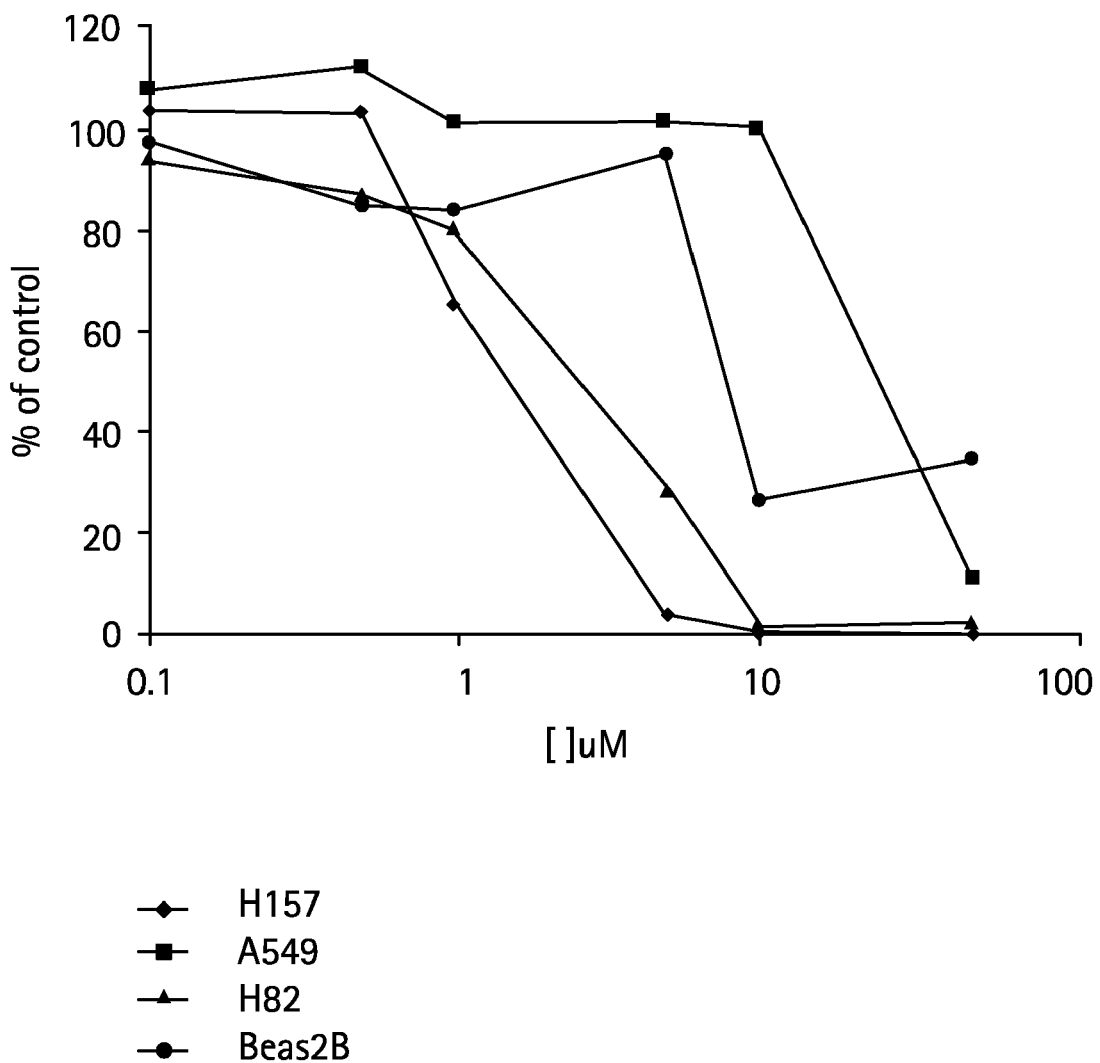
FIG. 10 depicts a 96 hr MTS dose response experiments for compound 46-TDW-35c in H157, A549, H82 and Beas2B cells.
Figure 12:
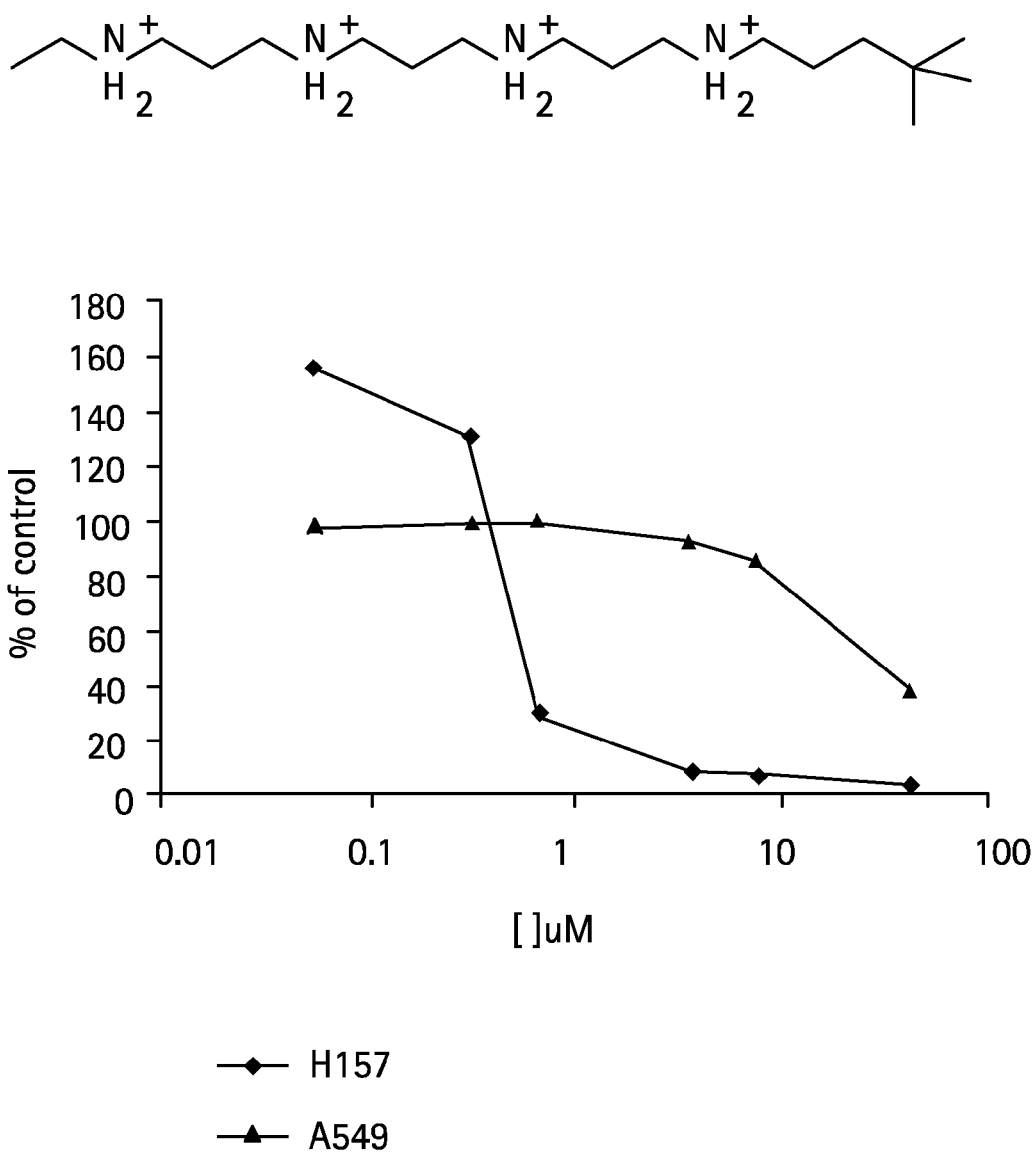
FIG. 12 depicts a 96 hr MTS dose response experiments for compound 39-TDW-12c in H157, and A549 cells.
Figure 13:
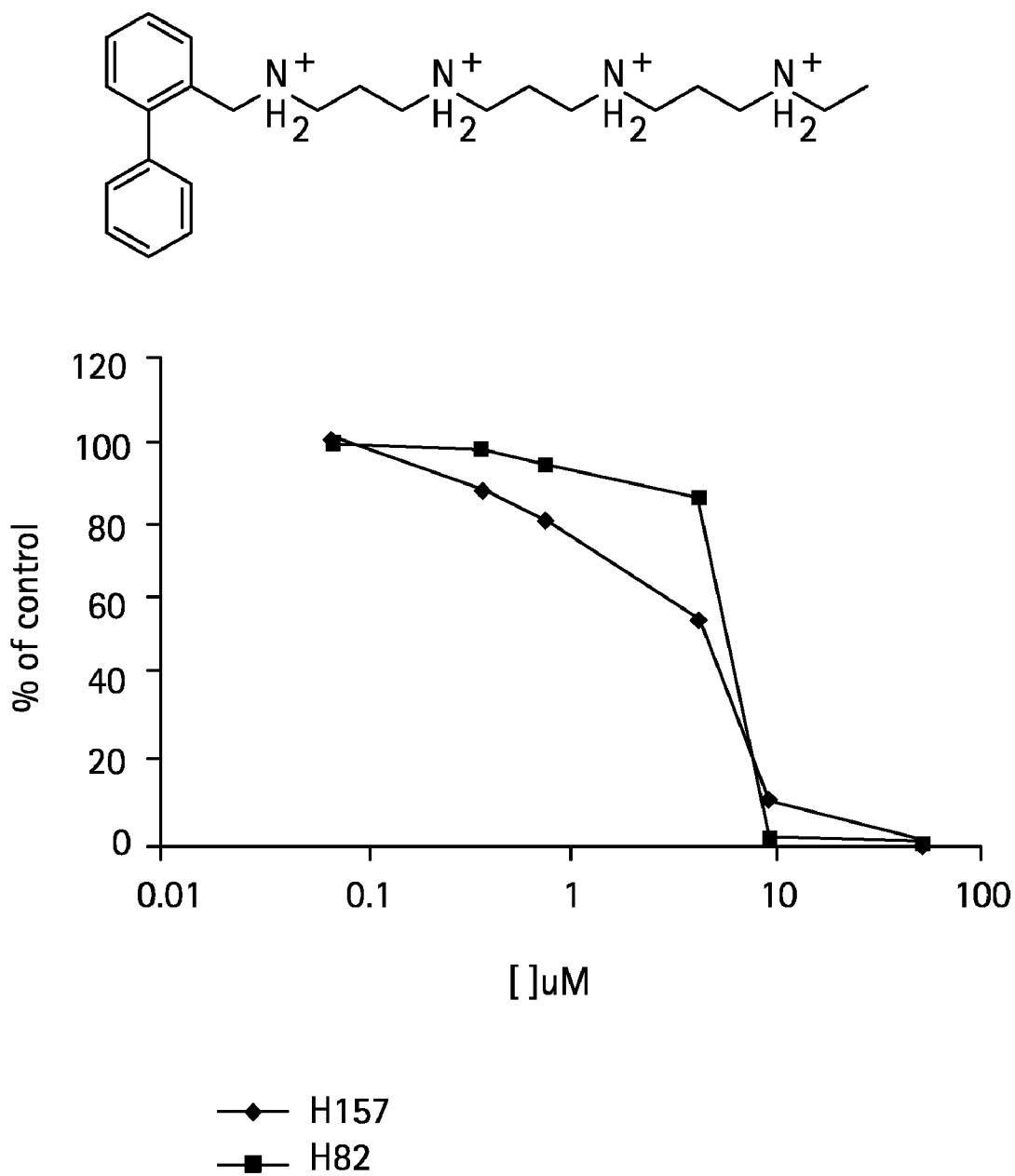
FIG. 13 depicts a 96 hr MTS dose response experiments for compound 39-IDW-20c in H157, and H82 cells.
Figure 15:
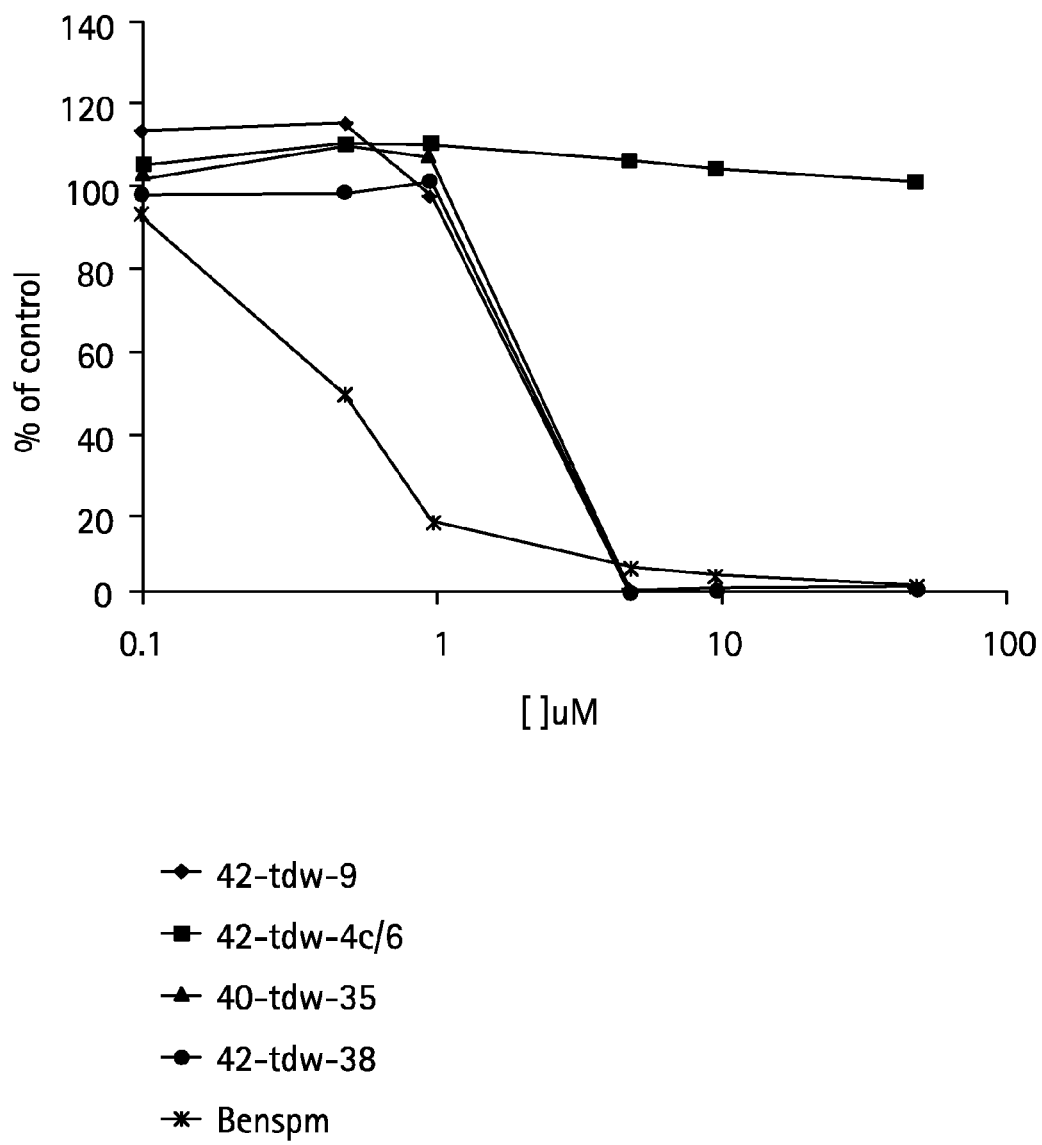
FIG. 15 depicts a 96 hr MTS dose response experiments for compounds 42-TDW-9, 42-TDW-4c/6, 40-TDW-35, 42-TDW-38 and BENSpm in H157 cells.
Figure 16:
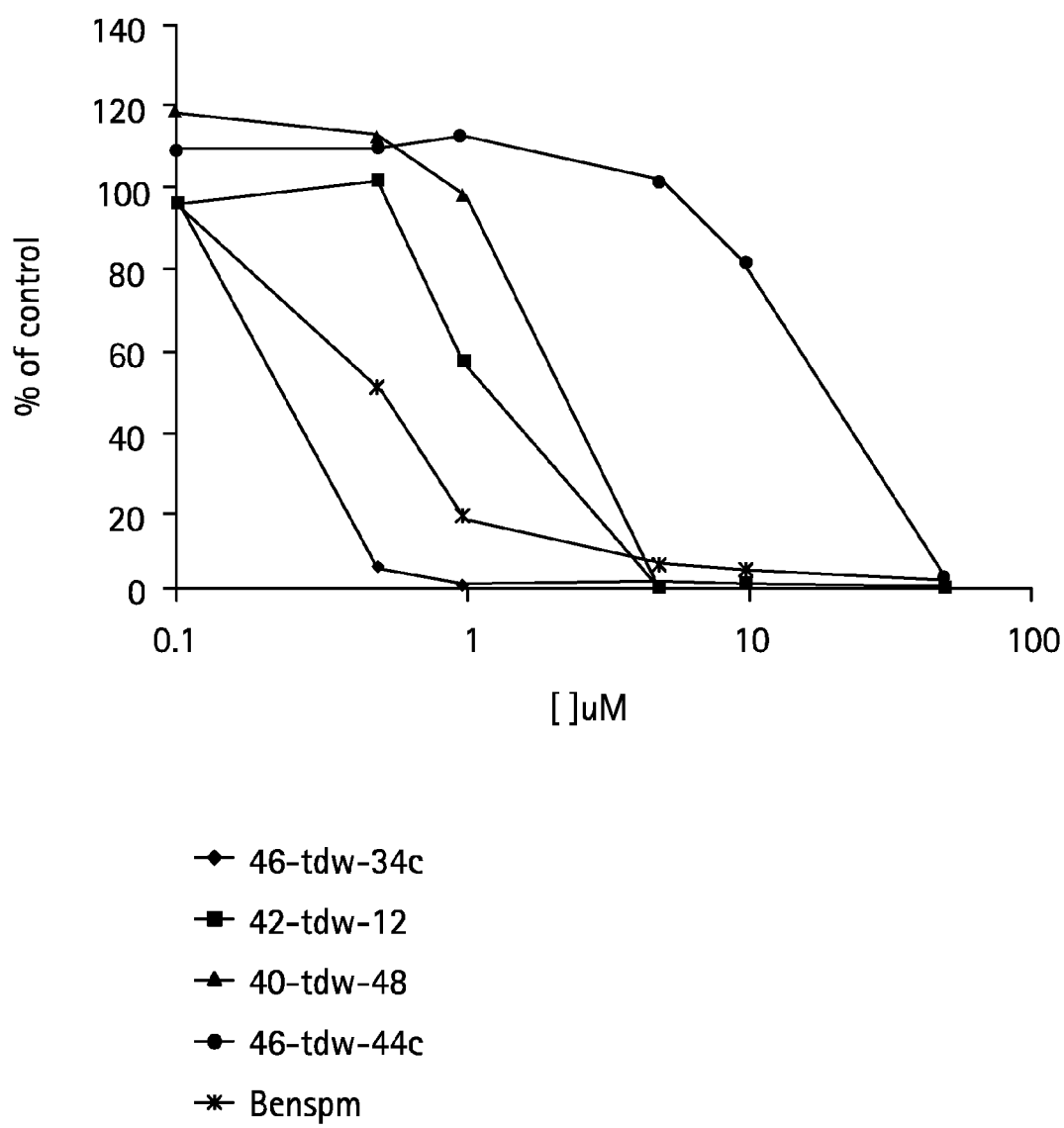
FIG. 16 depicts a 96 hr MTS dose response experiments for compounds 46-TDW-34c, 42-TDW-12, 40-TDW-48, 46-TDW-44c and BENSpm in H157 cells.
Figure 17:
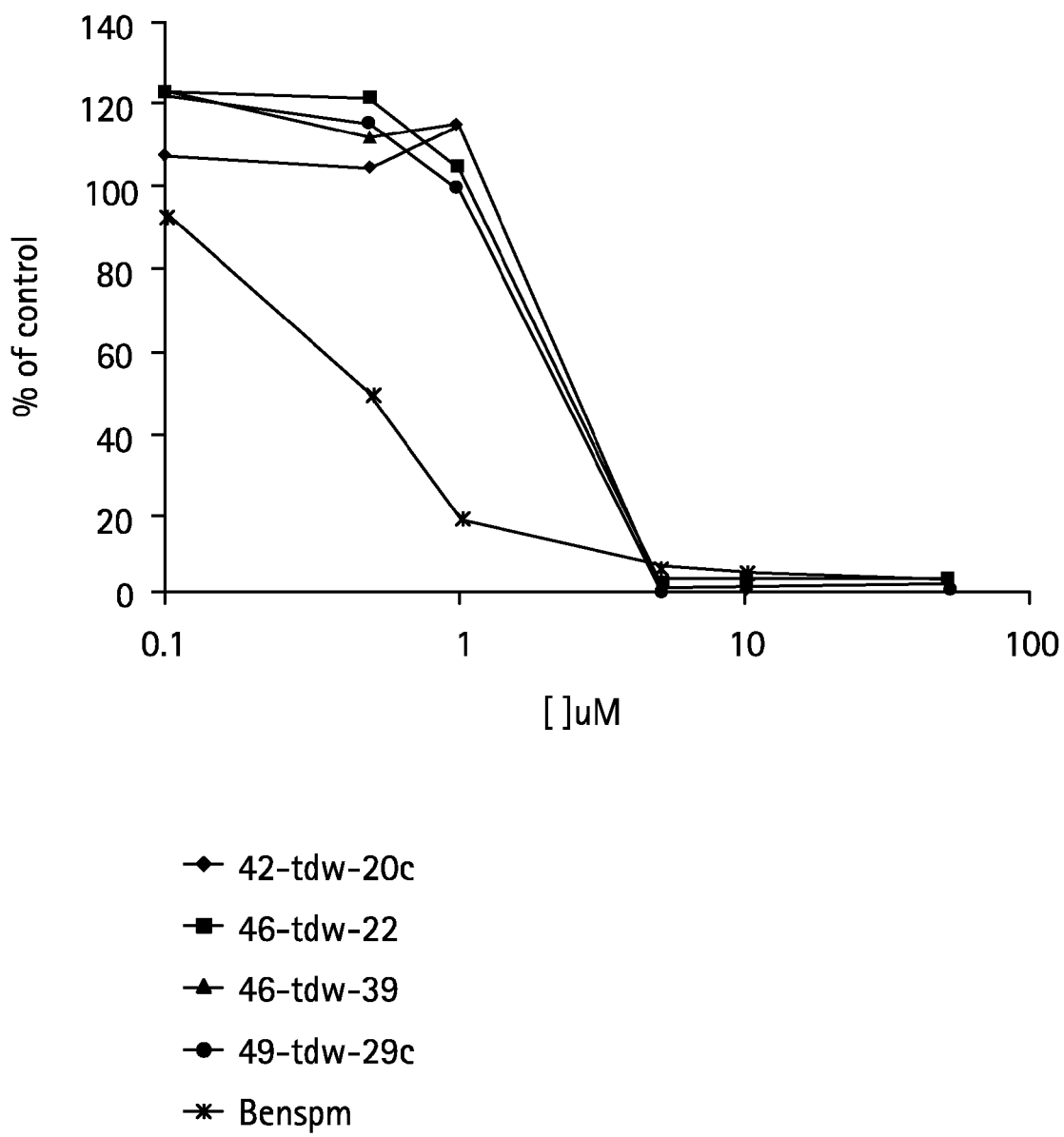
FIG. 17 depicts a 96 hr MTS dose response experiments for compounds 42-TDW-20c, 46-TDW-22, 46-TDW-39, 49-TDW-29c and BENSpm in H157 cells.
Figure 18:
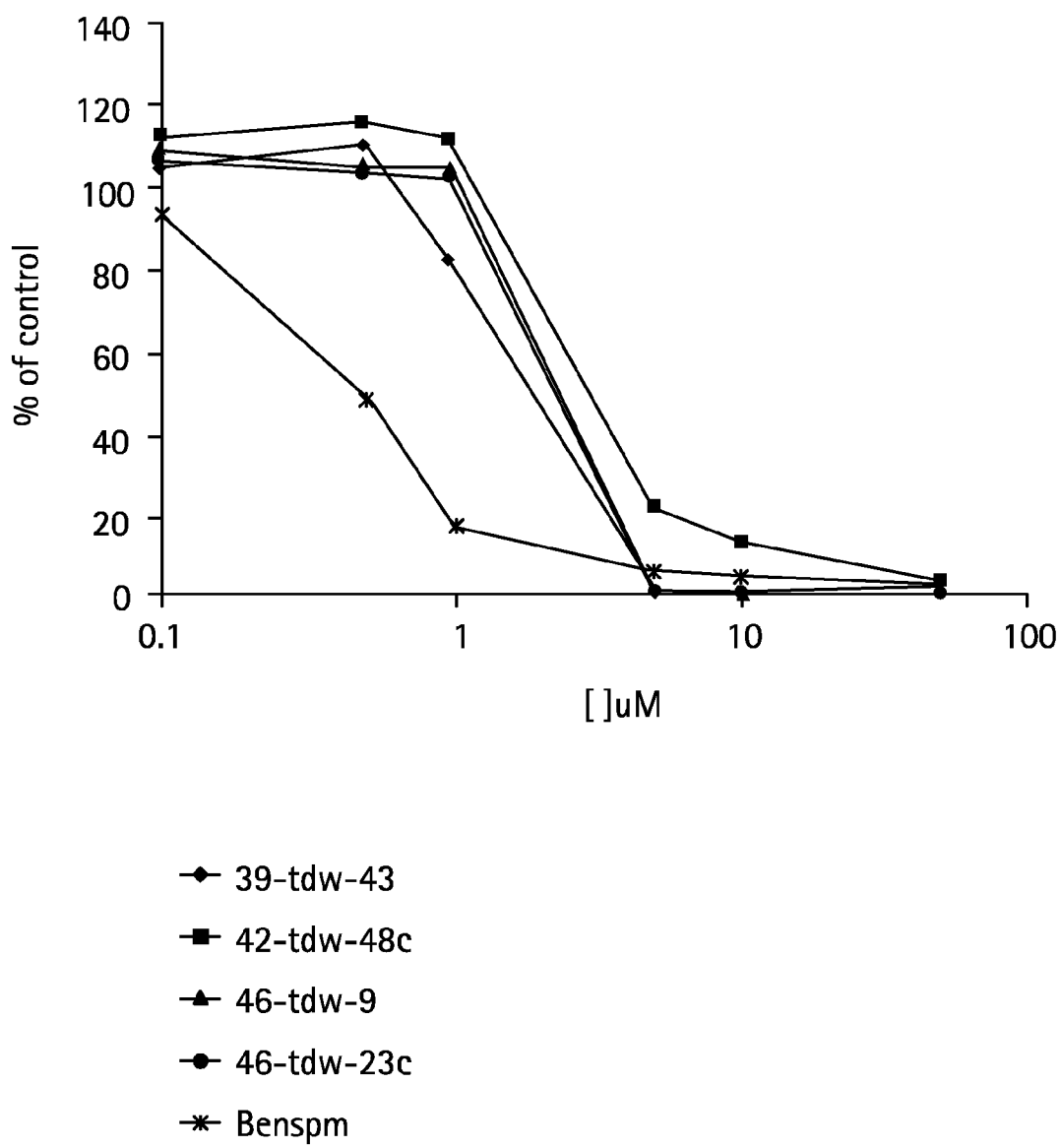
FIG. 18 depicts a 96 hr MTS dose response experiments for compounds 39-TDW-43, 42-TDW-48c, 46-TDW-9, 46-IDW-23c and BENSpm in H157 cells.
Figure 19:
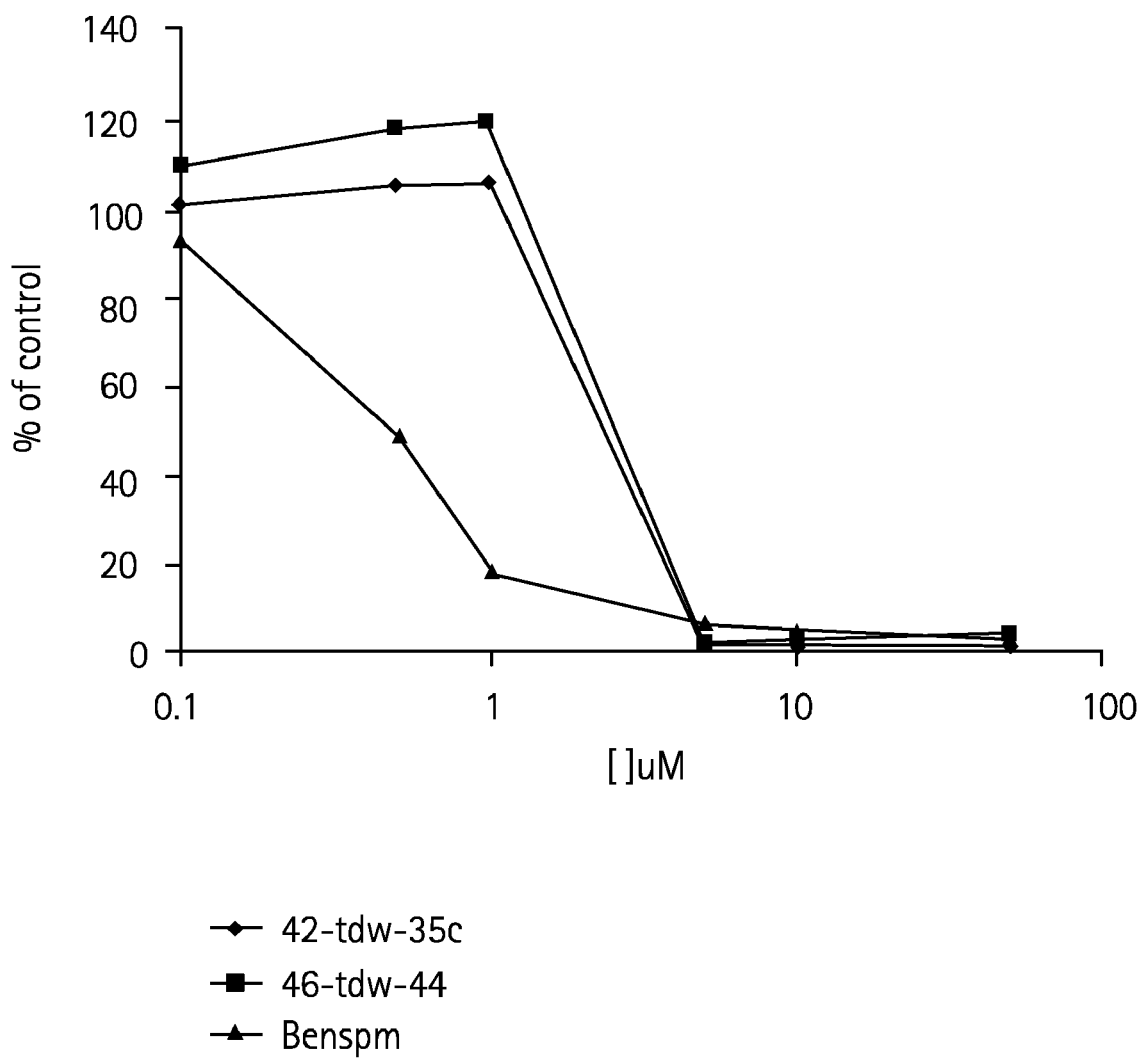
FIG. 19 depicts a 96 hr MTS dose response experiments for compounds 42-TDW-35c, 46-IDW-44 and BENSpm in H157 cells.

The results for H157, H82, and A549 cells are shown in Tables 2, 3 and 4 respectively. Note that the results for a 72 hr exposure in addition to the 96 hr exposure are shown for compound 49-TDW-29C in the H157 cells. The first column contains the compound identifier and the second column contains the IC$_{50}$ values (when a range is shown, e.g., 1-10 uM, this indicates that the IC$_{50}$ lies somewhere between the two endpoints of the range; the endpoints are the concentrations actually tested, one of which is lower than the IC$_{50}$ and one of which is higher). FIG. 1 depicts the results of a 96 hr MTS dose response experiments for compound 46-TDW-23c in H157, A549, H82 and Beas2B cells. FIG. 2 depicts the results of a 96 hr MTS dose response experiments for compound 49-TDW-9 in H157, A549, H82 and Beas2B cells. FIG. 3 depicts the results of a 96 hr MTS dose response experiments for compound 42-TDW-21c in H157, A549, H82 and Beas2B cells. FIG. 4 depicts the results of a 96 hr MTS dose response experiments for compound 46-TDW-19c in H157, A549, H82 and Beas2B cells. FIG. 5 depicts the results of a 96 hr MTS dose response experiments for compound 49-TDW-17c in H157, A549, H82 and Beas2B cells. FIG. 6 depicts the results of a 96 hr MTS dose response experiments for compound 40-TDW-37 in H157, A549, H82 and Beas2B cells. FIG. 7 depicts the results of a 96 hr MTS dose response experiments for compound 42-TDW-4 in H157, A549, H82 and Beas2B cells. FIG. 8 depicts the results of a 96 hr MTS dose response experiments for compound 49-TDW-29c in H157, A549, H82 and Beas2B cells. FIG. 9 depicts the results of a 96 hr MTS dose response experiments for compound 49-TDW-32c in H157, A549, H82 and Beas2B cells. FIG. 10 depicts the results of a 96 hr MTS dose response experiments for compound 46-TDW-35c in H157, A549, H82 and Beas2B cells. FIG. 11 depicts the results of a 96 hr MTS dose response experiments for compound 39-TDW-3 in H157, A549, and H82 cells. FIG. 12 depicts the results of a 96 hr MTS dose response experiments for compound 39-TDW-12c in 11157, and A549 cells. FIG. 13 depicts the results of a 96 hr MTS dose response experiments for compound 39-TDW-20c in H157, and H82 cells. FIG. 14 depicts the results of a 96 hr MTS dose response experiments for compounds 39-TDw-47c and 39-TDW-43 in H157 cells. FIG. 15 depicts the results of a 96 hr MTS dose response experiments for compounds 42-TDW-9, 42-TDW-4c/6, 40-TDW-35, 42-TDW-38 and BENSpm in H157 cells. FIG. 16 depicts the results of a 96 hr MTS dose response experiments for compounds 46-TDW-34c, 42-TDW-12, 40-TDW-48, 46-TDW-44c and BENSpm in H157 cells. FIG. 17 depicts the results of a 96 hr MTS dose response experiments for compounds 42-TDW-20c, 46-TDW-22, 46-TDW-39, 49-TDW-29c and BENSpm in H157 cells. FIG. 18 depicts the results of a 96 hr MTS dose response experiments for compounds 39-TDW-43, 42-TDW-48c, 46-TDW-9, 46-TDW-23c and BENSpm in H157 cells. FIG. 19 depicts the results of a 96 hr MTS dose response experiments for compounds 42-TDW-35c, 46-TDW-44 and BENSpm in H157 cells.

MTT dose response experiments in 235, MCF7, 435, and 10A cells were performed. MTT is a standard colorimetric assay used for measuring metabolic activity in cells. Briefly, about 200 ul of media not containing cells was added to column A of a 96 well plate and used as a blank. Next, 200 ul of media containing cells was added to the remaining wells and incubated overnight. The remaining wells contain about 4000-5000 MCF7 cells/well, 3000 231 cells/wells, 12,000 468 cells/well, or 9000 MCF 10A cells/well. Following incubation, the media in the wells was aspirated and replaced with 200 ul of fresh media in columns A and B of the 96 well plate. Column B was used as a control. Next 200 ul of fresh media containing the compound being tested was added to the remaining wells and incubated for 96 hrs. Compounds are routinely tested at concentrations ranging from 0.1 micromolar to 50 micromolar. Following incubation for 96 hrs, the media in each well was aspirated and replaced with 100 ul of 5 mg/ml MTT (3-(4,5-Dimethylthiazol-2-yl)-2,5-diphenyltetrazolium bromide) solution in Serum-Free media and incubated for 4 hours. Following incubation with MTT solution, the MTT solution was removed from the wells and replaced with 200 ul of a 1:1 Etoh+DMSO solution and incubated for 20 minutes. Following incubation with the Etoh+DMSO solution the plates were read at 540 nm and used to determine the metabolic activity of the cells in the presence of the test compound, relative to the control. IC$_{50}$ values for the test compounds were extracted based on the results.

Figure 20:
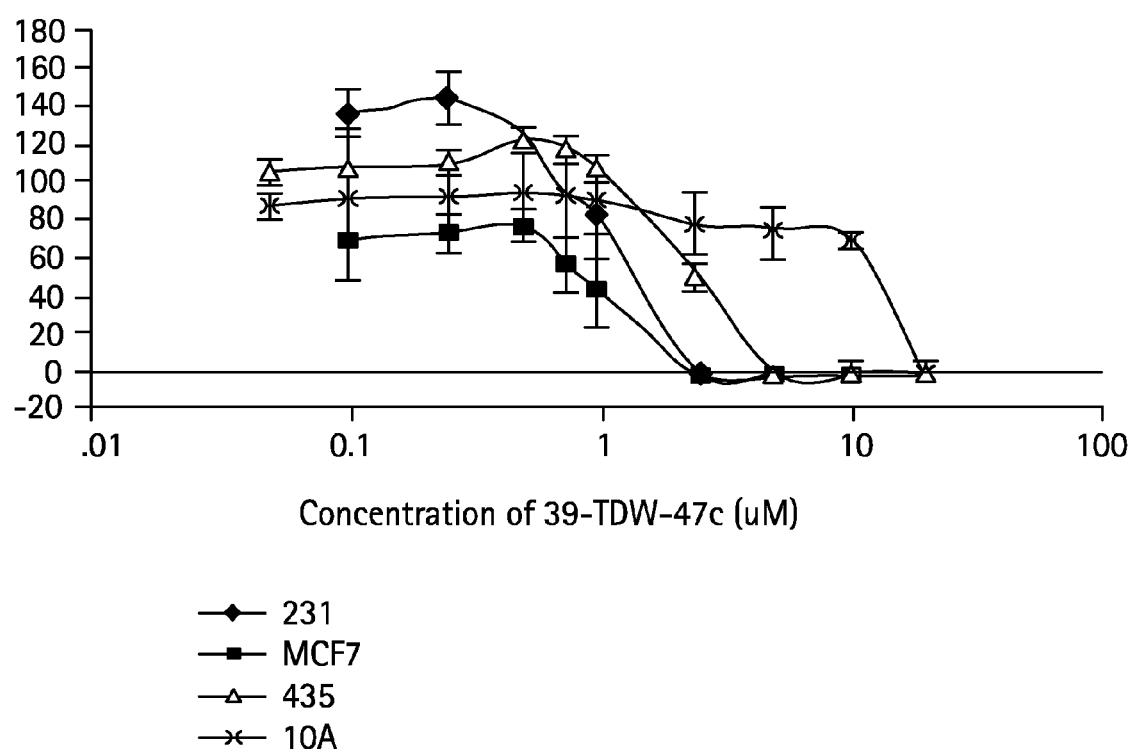
FIG. 20 depicts MIT assays after 96 hrs of treatment with compound 9-TDW-47c.
Figure 21:
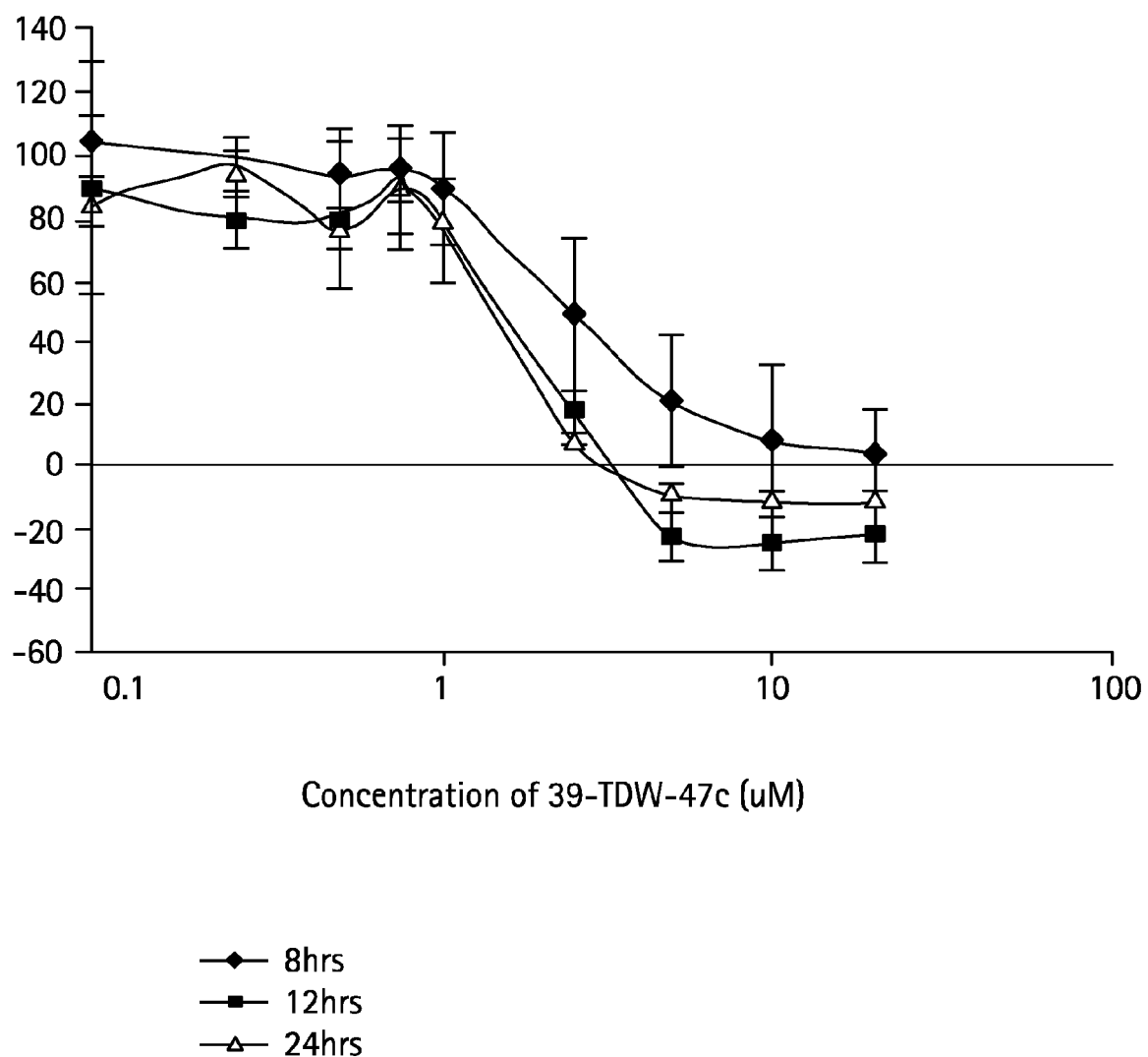
FIG. 21 depicts the time course for compound 39-IDW-47c in 231 cells.
Figure 22:
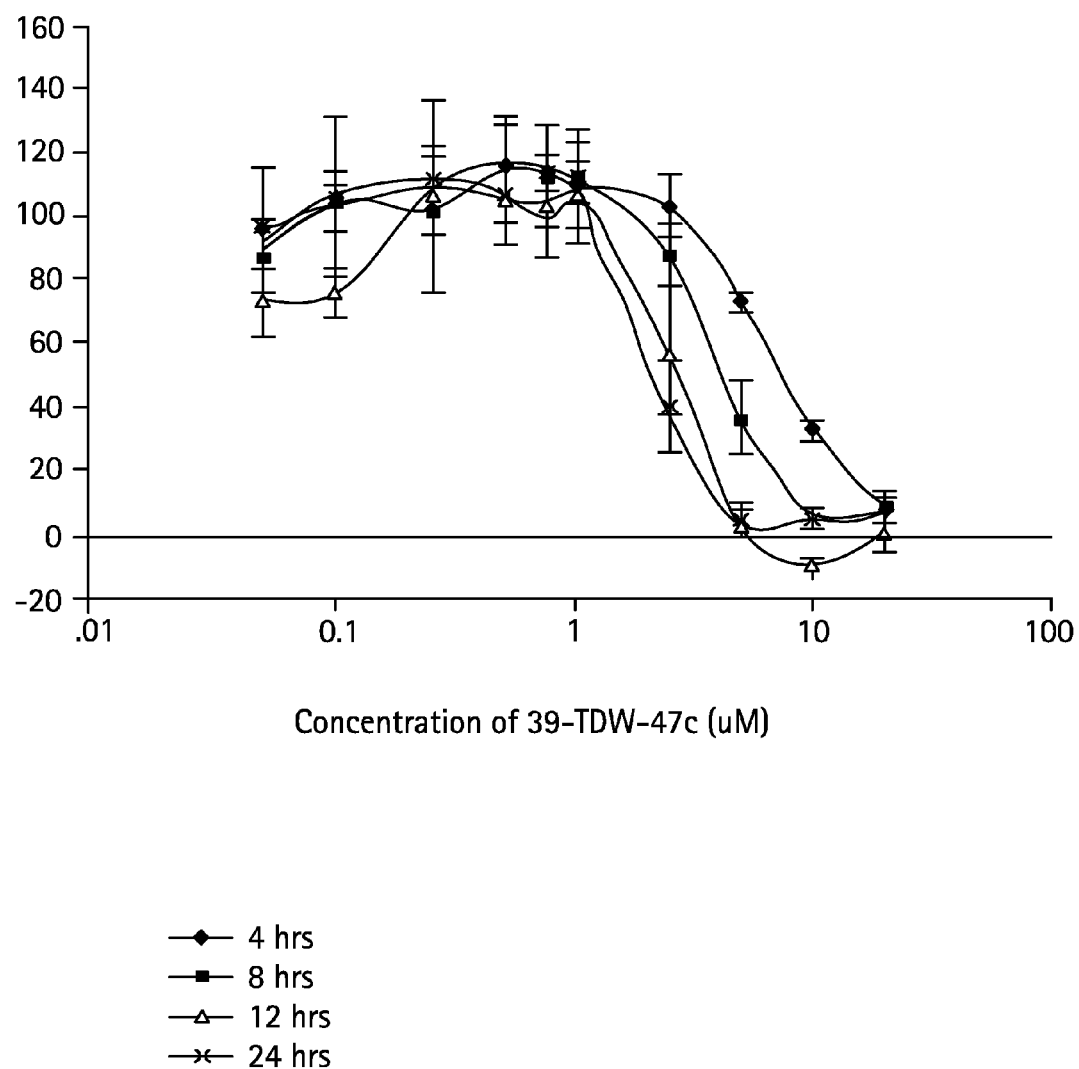
FIG. 22 depicts the time course for compound 39-TDW-47c in 435 cells.
Figure 23:
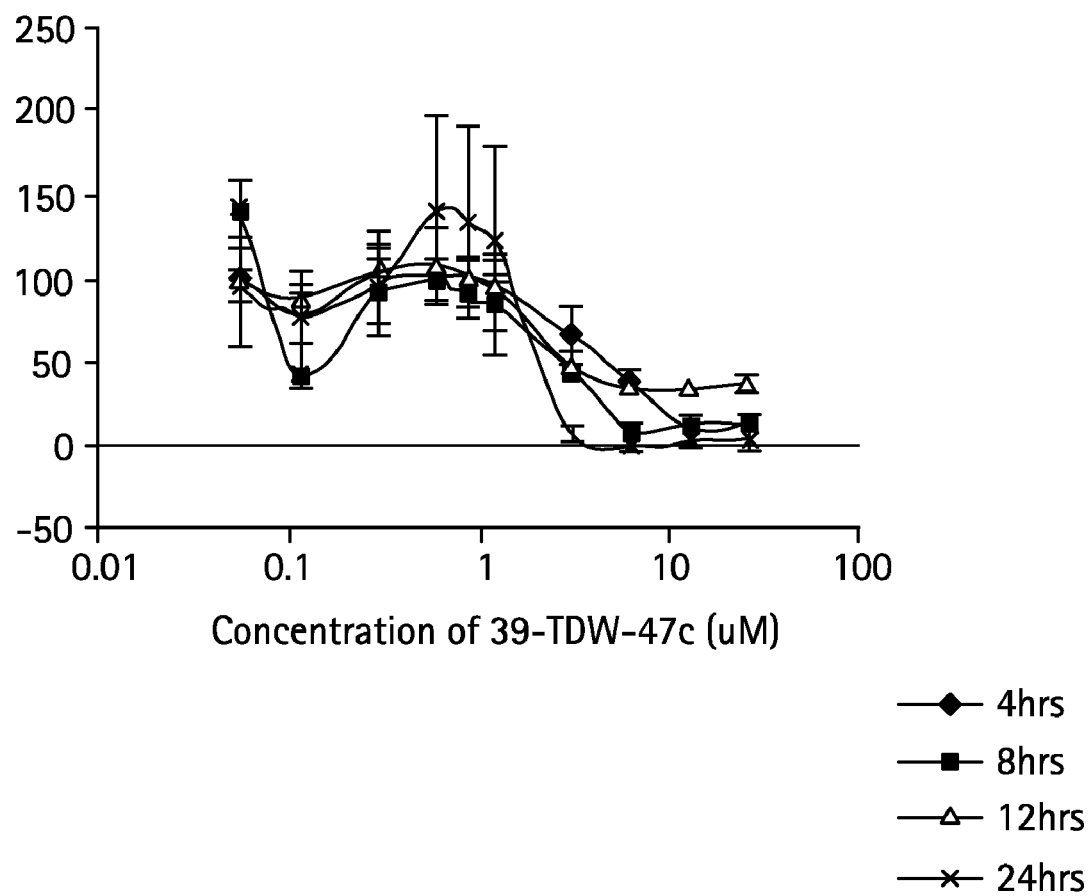
FIG. 23 depicts the time course for compound 39-IDW-47c in MCF7 cells.
Figure 24:
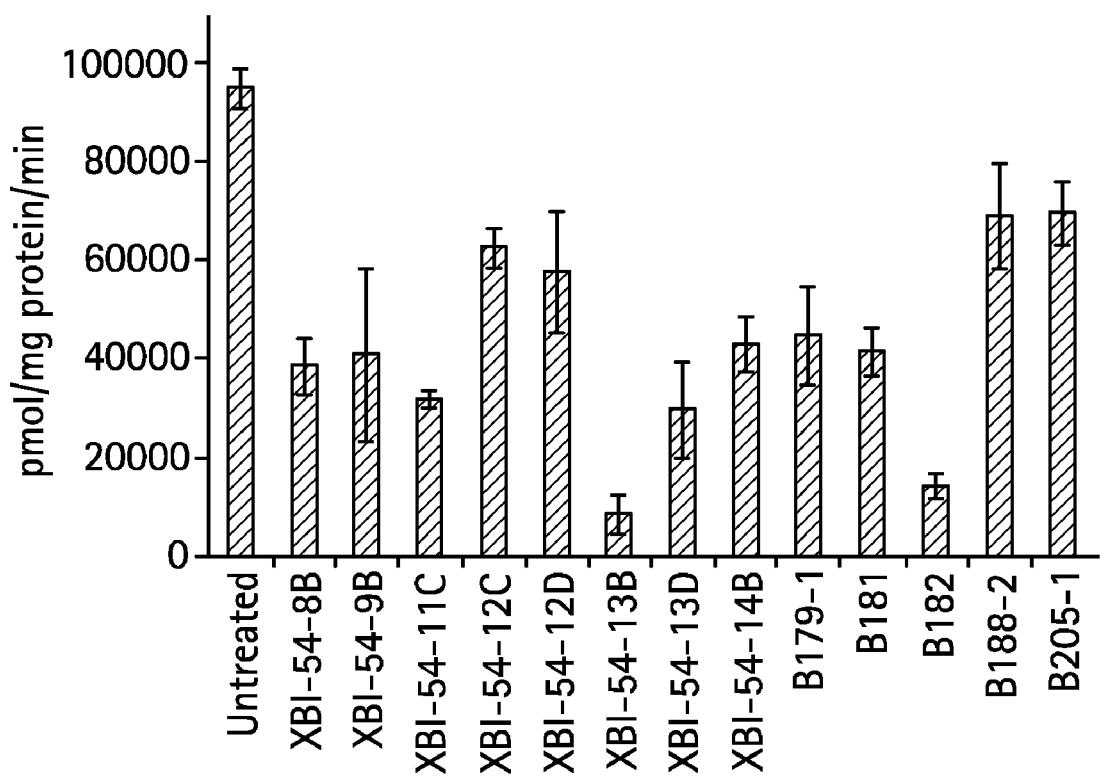
FIG. 24 depicts inhibition of LSD1 activities by certain polyaminoguanidines and polyaminobiguanides.
Figure 25:
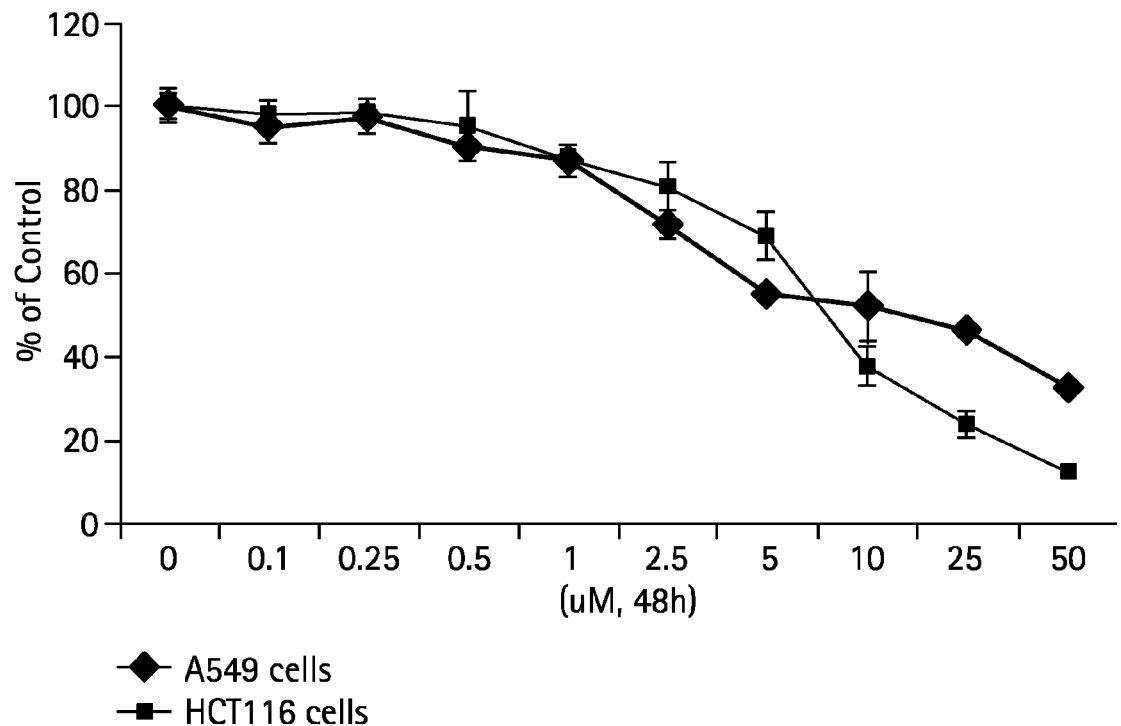
FIG. 25 depicts the effects of XB1-54-13B on tumor cell growth.
Figure 26:
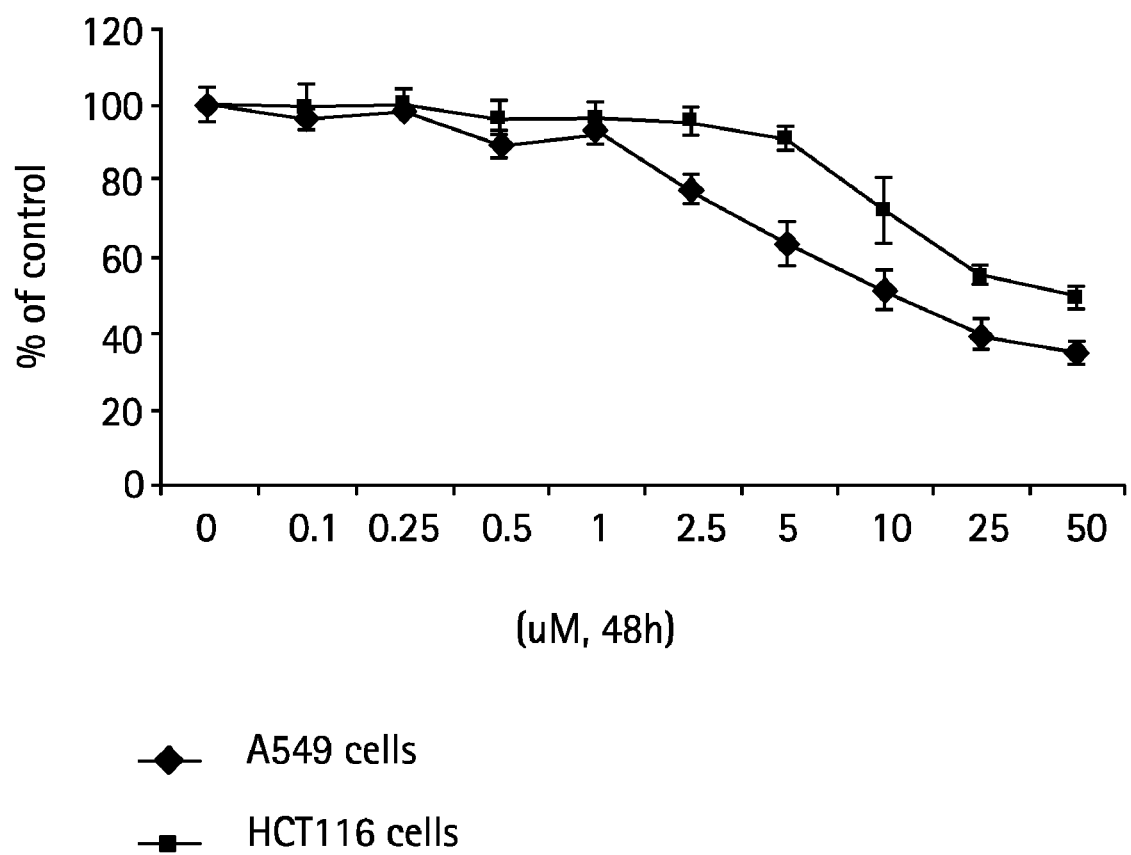
FIG. 26 depicts the effects of B182 on tumor cell growth.
Figure 27:
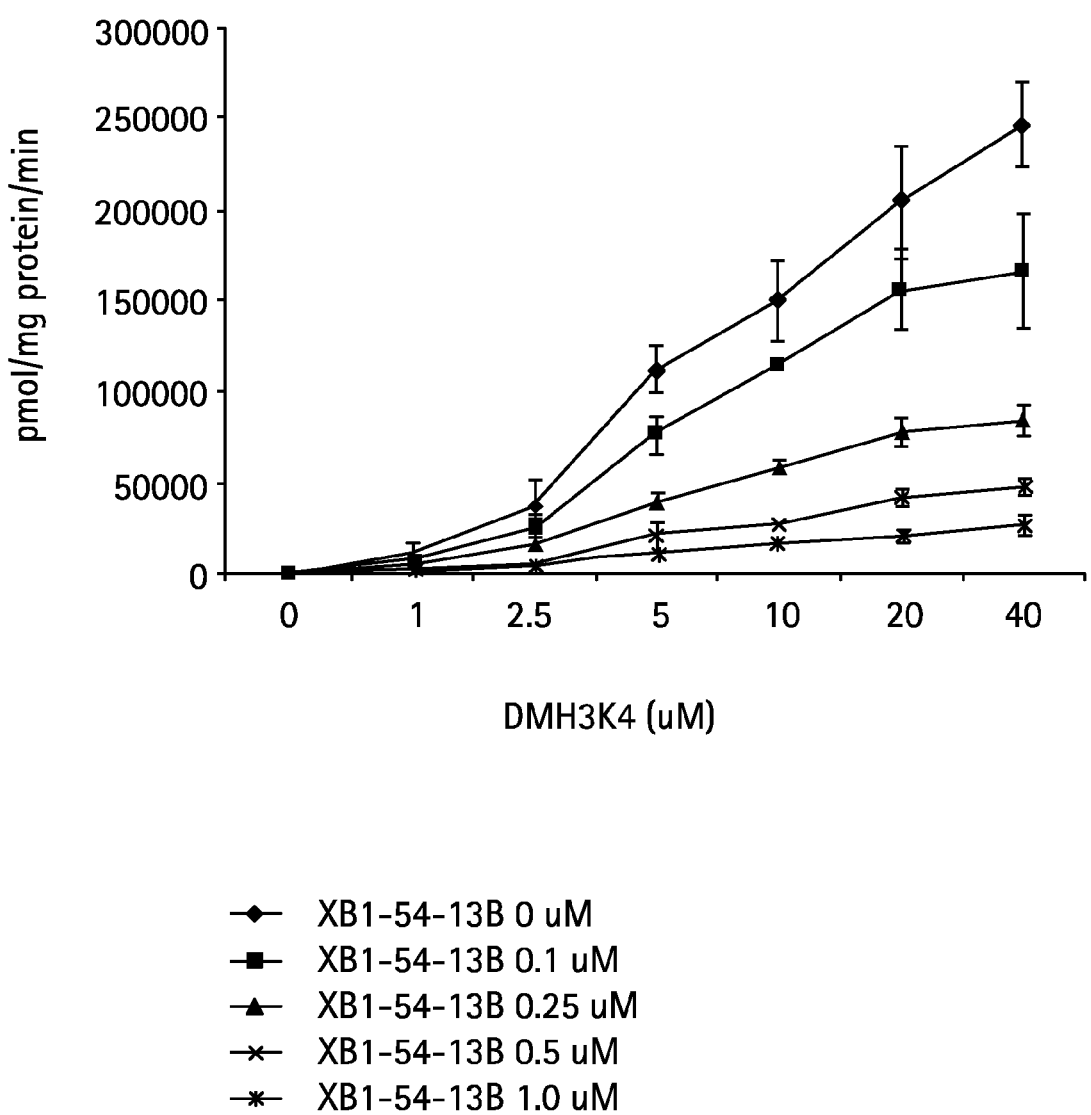
FIG. 27 depicts a kinetic assay of dose dependent inhibition of LSD1 activity by XBI-54-13B.
Figure 28:
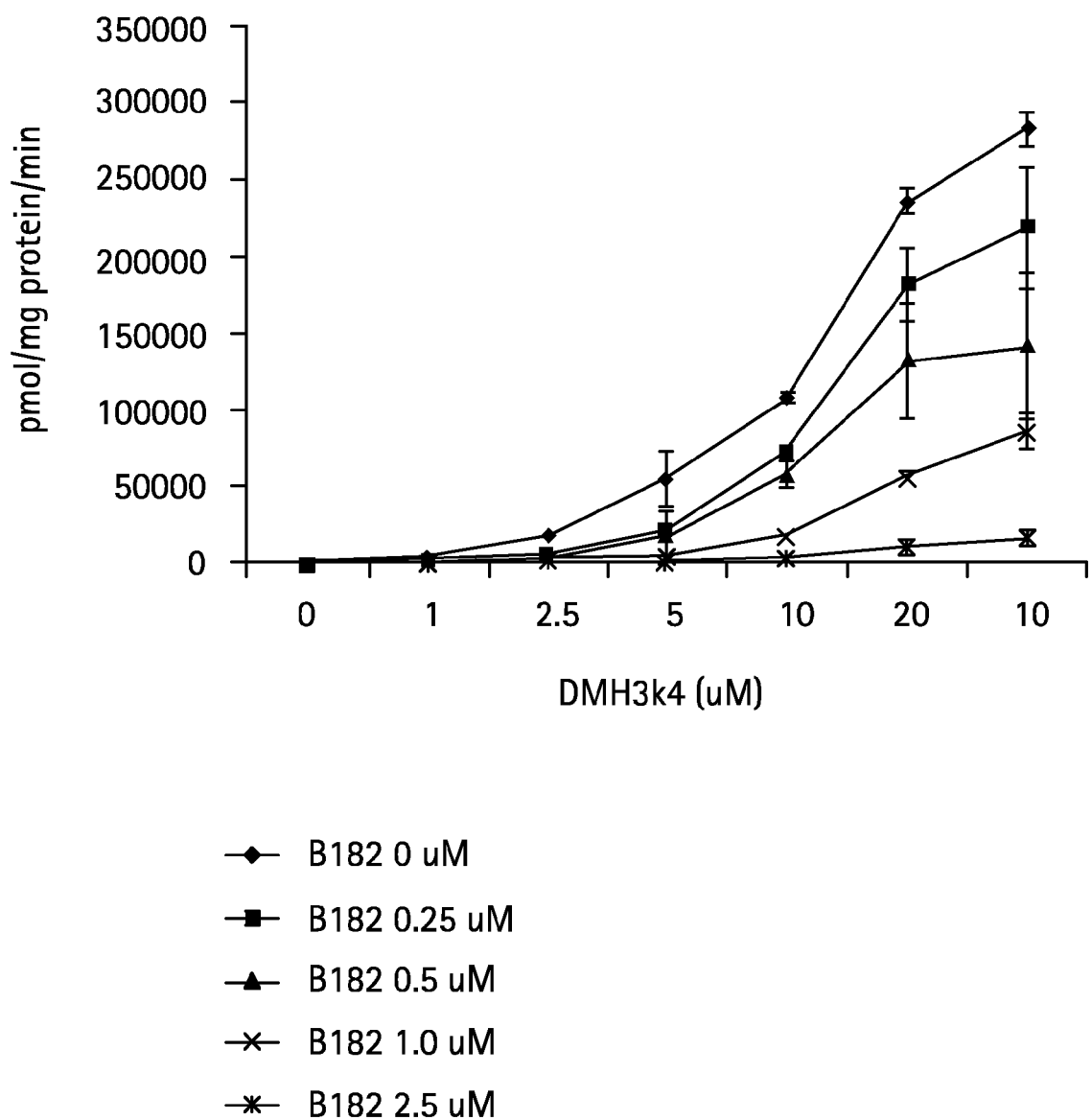
FIG. 28 depicts a kinetic assay of dose dependent inhibition of LSD1 activity by B182.
Figure 29:
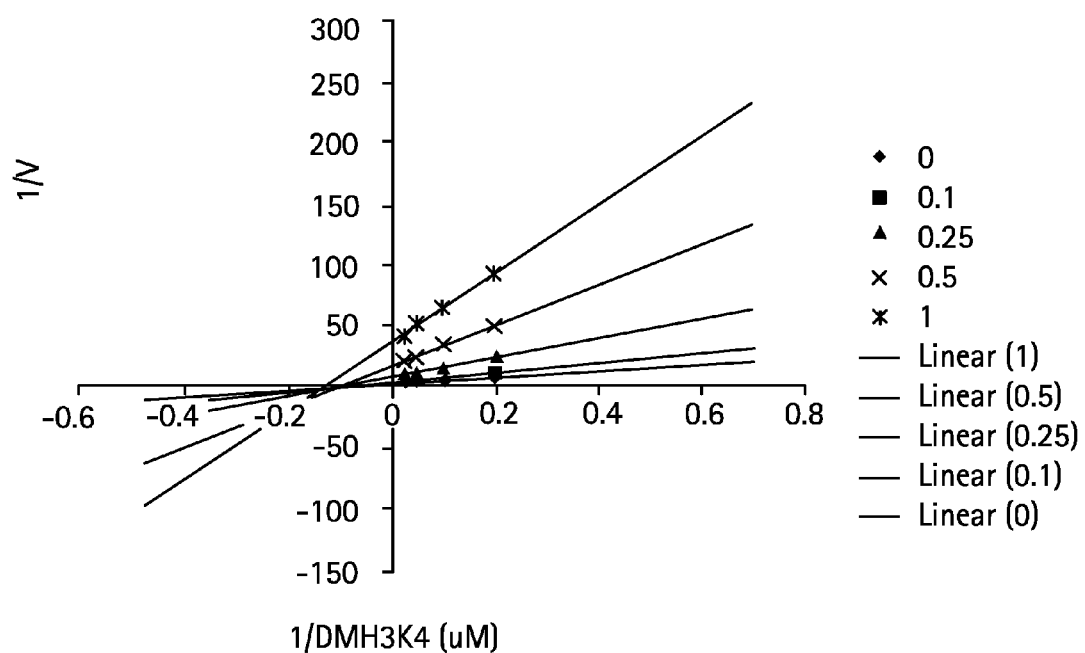
FIG. 29 depicts a Lineweaver-Burk plot for inhibition of LSD1 activity by XBI-54-13B and a table with $V_{max}$ (nmol/mg protein/min) and $K_M$ (uM) values.
Figure 30:
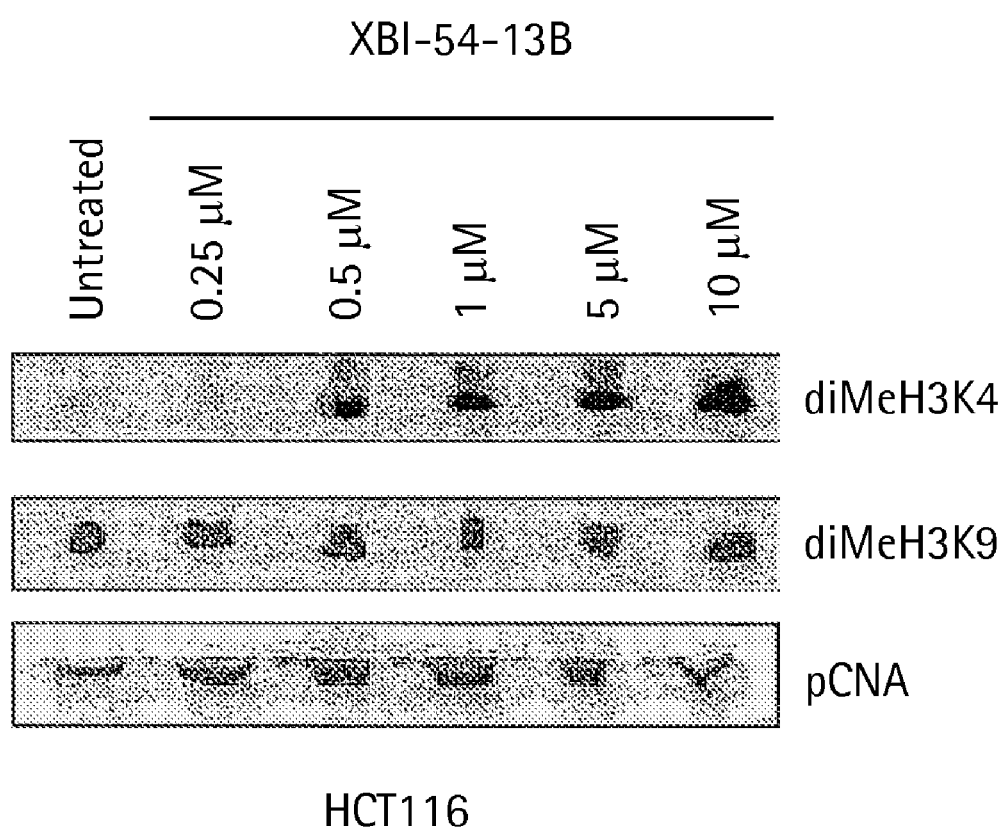
FIG. 30 depicts gels demonstrating the effect of XBI-54-13B on levels of dimethyl H3K4, dimethyl H3K9, and proliferating cell nuclear antigen.
Figure 31:
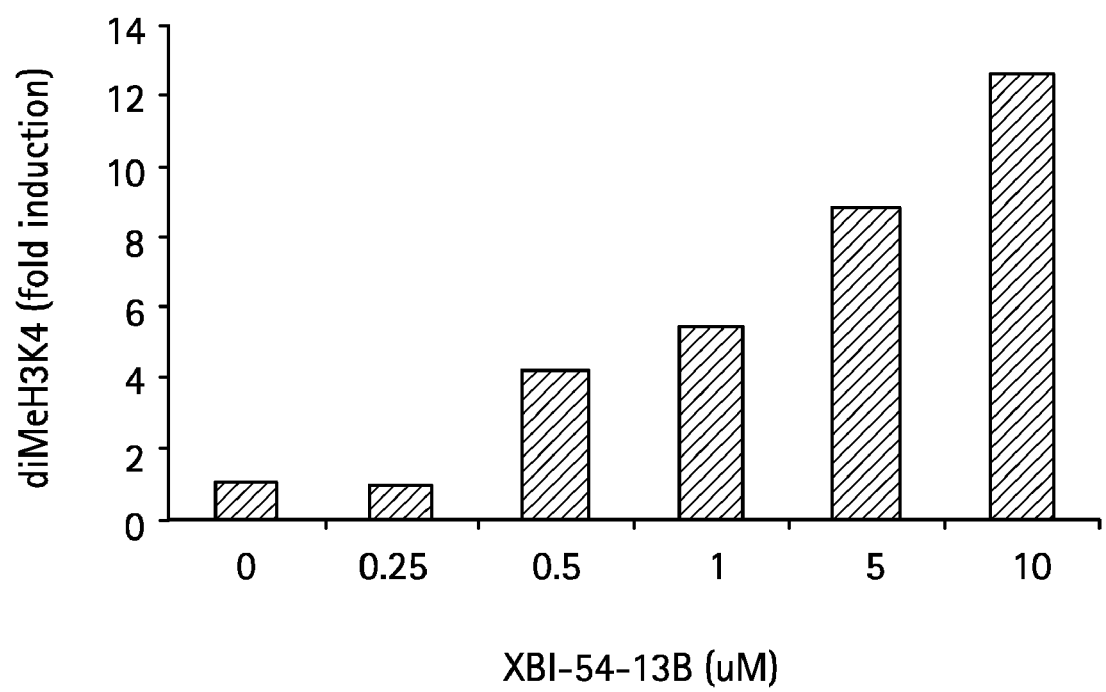
FIG. 31 depicts the quantitative effect of XBI-54-13B on levels of methylated histone H3K4.
Figure 32:
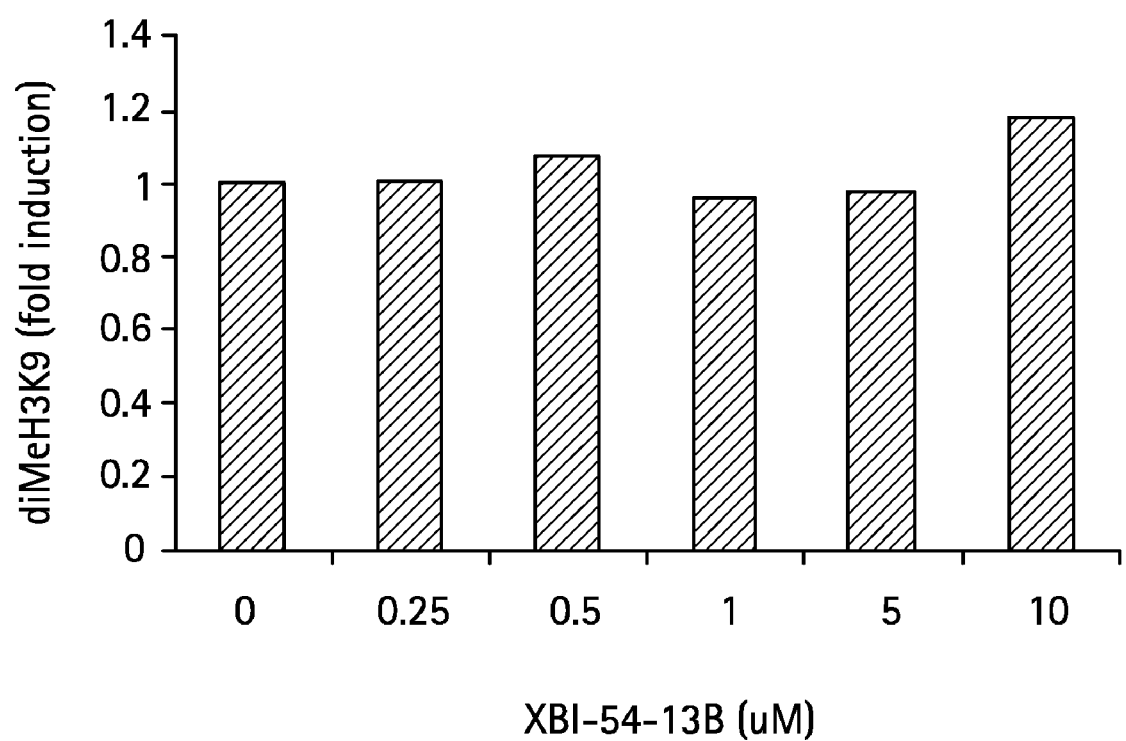
FIG. 32 depicts the quantitative effect of XBI-54-13B on levels of methylated histone H3K9.

The results of an MTT assay after 96 hrs of treatment with compound 39-TDW-47c at different concentrations in 231, MCF7, 435, and 10A cells is shown in FIG. 20. A time course experiment in 231 cells following 8, 12, and 24 hr exposure of compound 39-TDW-47c at differing concentrations in shown in FIG. 21. A time course experiment in 435 cells following 4, 8, 12, and 24 hr exposure of compound 39-TDW-47c at different concentrations in shown in FIG. 22. A time course experiment in MCF7 cells following 4, 8, 12, and 24 hr exposure of compound 39-TDW-47c at different concentrations in shown in FIG. 23.

SSAT (spermidine/spermine-N$^t$-acetyltransferase) activity experiments in H157, H82, and A549 cells following exposure to select compounds were performed. A detailed protocol for determining SSAT activity is described in Casero et al., Cancer Research, 49:3829 (1989). Briefly, the SSAT activity was measured by harvesting the treated cells at the exposure time. The cells were then lysed and treated with spermidine, and 1-[$^{14}$C]acetyl coenzyme A for 5 minutes. Enzyme activity was measured in term of picomoles of [$^{14}$C] acetylspermidine formed per mg of cell protein per min (pmol/mgP/min).

The results are show in tables 5 (H157), 9 (H82), and 12 (A549) respectively. In Tables 5 and 12, the compound identifier, treatment concentration, control activity, SSAT activity following exposure and exposure time are listed in columns 1, 2, 3, 4, and 5 respectively. The activity in Tables 5 and 12 is reported as picomoles of SSAT per mg of protein per min. Table 9 lists the compound identifier, the exposure concentration, the activity, and exposure time in columns 1, 2, 3 and 4 respectively. No SSAT induction was observed for H82 cells and thus the values of the control and activity following exposure are not listed.

Putrescine, spermidine, and spermine polyamine levels in H157 and H82 cells following exposure to select compounds were performed. Polyamine levels were determined using the precolumn dansylation labeling, reverse-phase high-pressure liquid chromatography method as described by Kabra et al., J. Chromotography, 380:19 (1986). The results are show in Tables 6 and 11 for H157 and H82 cells respectively. The compound identifier, treatment concentration, observed polyamine level, and exposure time are listed in columns 1, 2, 3, and 4 respectively. Polyamine levels are reported as increased (inc), decrease (dec), or no change (N/C). In some case the specific levels of putrescine, spermidine, and/or spermine are listed.

SMO (Spermine Oxidase) activity in H157 cells following treatment with compound 46-TDW-34C is shown in Table 7, A detailed protocol for measuring SMO activity is described in Wang et al., Cancer Research, 61:5370 (2001). The compound identifier, the treatment concentration, the control activity, the activity following treatment and the exposure time are listed in columns 1, 2, 3, 4, and 5 respectively. The activity results are reported in picomoles of spermine converted per mg of cell protein per min (pmol/mgP/min).

ODC (Ornithine decarboxylase) activity experiments in H157 were performed. A detailed protocol for measuring ODC activity is described in Pegg et al., Methods Enzymology, 94:158 (1983). The results are show in Table 10. The compound identifier, treatment concentration, control activity, activity following treatment, and exposure time are listed in columns 1, 2, 3, 4 and 5 respectively. The activity results are reported in picomoles of $CO_2$ released per mg of cell protein per hour (pmol/mgP/hr).

Treatment induced cell cycle measurements in H157 cells were performed. Following exposure of the cells to a compound of interest, at a concentration of 10 uM, for 24 hrs, the cells were harvested, prepared and transferred to a FACS for cell cycle analysis. (See Carlisle et al., Clinical Cancer Research 8:2684 (2002) and references therein.) The results are shown in Table 8. The results depict the percentage of cells which are in the G1 phase, S phase, and G2/M phases.

TABLE 2

96 Hr. MTS dose response experiment in H157
(non-small cell lung carcinoma) cells

| Compound | $IC_{50}$ |
|---|---|
| ZQW-36 | 1-10 uM |
| ZQW-35 | 1-10 uM |
| ZQW-35c | 1-10 uM |
| ZQW-44 | >13 uM |
| ZQW-46 | 13 uM |
| ZQW-35-7c | >10 uM |
| ZQW-35-8 | >10 uM |
| ZQW-35-8c | 1-10 uM |
| YZ33049c | 1-10 uM |
| YZ33035 | >10 uM |
| YZ33050c | ~1 uM |
| YZ33049 | ~1 uM |
| YZ33041 | >10 uM |
| YZ33046 | >10 uM |
| 39-TDW-11 | 1-5 uM |
| 39-TDW-3 | .53-2.7 uM |
| 39-TDW-10 | >50 uM |
| 39-TDW-12c | .25-.5 uM |
| 39-TDW-12 | >50 uM |
| 39-TDW-20c | 2.76-5.52 uM |
| 40-TDW-1 | 2.69-5.38 uM |
| 39-TDW-47c | .65-3.2 uM |
| 39-TDW-43 | .59-2.96 uM |
| 40-TDW-19 | 5.3-26.5 uM |
| 40-TDW-26c | 10-50 uM |
| 40-TDW-23 | 10-50 uM |
| 40-TDW-31c | 0-.1 uM |
| 40-TDW-29c | 10-50 uM |
| 40-TDW-30 | .1-.5 uM |
| 40-TDW-28 | 10-50 uM |
| 40-TDW-35 | 1-5 uM |
| 40-TDW-37 | 1-5 uM |
| 40-TDW-48 | 1-5 uM |
| 42-TDW-4 | 1-5 uM |
| 42-TDW-4c | 1-5 uM |
| 42-TDW-9 | 1-5 uM |
| 42-TDW-12 | 1-5 uM |
| 42-TDW-14 | 10-50 uM |
| 42-TDW-20c | 1-5 uM |
| 42-TDW-21c | 1-5 uM |
| 44-DHEJ-4c | >24 uM |
| 44-DHEJ-8c | 2.95-5.89 uM |
| 44-DHEJ-7c | >22 uM |
| 44-DHEJ-9 | >24 uM |

TABLE 2-continued

96 Hr. MTS dose response experiment in H157
(non-small cell lung carcinoma) cells

| Compound | $IC_{50}$ |
|---|---|
| 44-DHEJ-12c | >23 uM |
| 42-TDW-35c | 1-5 uM |
| 42-TDW-43 | 1-5 uM |
| 42-TDW-40c | 5-10 uM |
| 42-TDW-40 | 10-50 uM |
| 42-TDW-38 | 1-5 uM |
| 42-TDW-45 | >50 uM |
| 42-TDW-50 | 10-50 uM |
| 42-TDW-45C | .5-1 uM |
| 42-TDW-49 | >50 uM |
| 46-TDW-9C | >50 uM |
| 46-TDW-9 | 1-5 uM |
| 46-TDW-12C | >50 uM |
| 46-TDW-12 | >50 uM |
| 46-TDW-19C | 1-5 uM |
| 46-TDW-23C | 1-5 uM |
| 46-TDW-22 | 1-5 uM |
| 46-TDW-24 | 10-50 uM |
| 46-TDW-29 | 50-100 uM |
| 46-TDW-35 | 10-50 uM |
| 46-TDW-25C | 10-50 uM |
| 46-TDW-31C | 10-50 uM |
| 46-TDW-34C | 1-5 uM |
| 46-TDW-30 | 10-50 uM |
| 46-TDW-35C | 1-5 uM |
| 46-TDW-39 | 1-5 uM |
| 46-TDW-42 | 10-50 uM |
| 46-TDW-44 | 1-5 uM |
| 46-TDW-44C | 10-50 uM |
| 46-TDW-45 | 10-50 uM |
| 49-TDW-1C | 1-5 uM |
| 46-TDW-47 | 10-50 uM |
| 44-DHEJ-37 | 2.49-4.98 uM |
| 44-DHEJ-37C | 5.21-26.1 uM |
| 44-DHEJ-38 | 21.9 uM |
| 44-DHEJ-40C | >26.1 uM |
| 49-TDW-3C | 10-50 uM |
| 49-TDW-5C | 5-10 uM |
| 44-DHEJ-36 | >50 uM |
| 44-DHEJ-36C | >50 uM |
| 51-DHEJ-A | 10-50 uM |
| 51-DHEJ-B | >50 uM |
| 51-DHEJ-C | >50 uM |
| 44-DHEJ-35C | 10-50 uM |
| 44-DHEJ-48C | >50 uM |
| 44-DHEJ-49 | 1-5 uM |
| 44-DHEJ-5C | >31 uM |
| 44-DHEJ-10C | >29 uM |
| B188-2 | 5-10 uM |
| B205'-1 | 50 uM |
| B181 | 5-10 uM |
| B179-1 | 10-50 uM |
| B182 | 5-10 uM |
| 49-TDW-15 | .5-1 uM |
| 49-TDW-17C | .1-.5 uM |
| 49-TDW-29C | .1-.5 uM, .5-1 uM (72 hr MTS) |
| 44-DHEJ-41 | 7.16-35.8 uM |
| 44-DHEJ-41C | 5 uM |
| 51-DHEJ-15C | >29 uM |
| 51-DHEJ-16 | >36 uM |
| 51-DHEJ-2 | .5-1 uM |
| 51-DHEJ-2C | >50 uM |
| 50-DHEJ-3C | >50 uM |
| 49-TDW-31 | 10-50 uM |
| 51-DHEJ-19 | 10-50 uM |
| 51-DHEJ-18 | 10-50 uM |
| 51-DHEJ-20 | >50 uM |
| 53-SV-3C | 1-5 uM |
| YZ3604C | .5-1 uM |
| 53-SV-2C | >50 uM |
| B275 | 10 uM |
| B291 | 10-50 uM |
| B283-1 | >50 uM |
| B283-2 | >50 uM |
| B300 | 10-50 uM |

TABLE 2-continued

96 Hr. MTS dose response experiment in H157 (non-small cell lung carcinoma) cells

| Compound | $IC_{50}$ |
|---|---|
| B301 | 10-50 uM |
| B298 | 10-50 uM |
| B299 | 10-50 uM |
| 51-DHEJ-38C | 10-50 uM |
| 51-DHEJ-45 | 1-5 uM |
| 51-DHEJ-49C | >50 uM |
| XBI-54-9B | >50 uM |
| XBI-54-8B | >50 uM |
| XBI-54-11C | 10-50 uM |
| XBI-54-13B | 10-50 uM |
| XBI-54-12C | 10-50 uM |
| XBI-54-12D | 10-50 uM |
| XBI-54-14B | 10-50 uM |
| XBI-54-13D | 10-50 uM |
| 55-DHEJ-7C | >50 uM |
| 51-DHEJ-8 | >50 uM |
| DG-52-27C | .5-1 uM |
| DG-52-28 | 1 uM |
| DG-52-29C | >50 uM |
| SV-53-17C2 | 10-50 uM |
| SV-53-22C1 | 5-10 uM |
| SV-53-18C2 | 10-50 uM |
| 55-DHEJ-17C | >50 uM |
| 55-DHEJ-18 | >50 uM |
| 55-DHEJ-26 | >50 uM |
| 55-DHEJ-35C | 10-50 uM |
| 55-DHEJ-24C | >50 uM |
| 44-DHEJ-34C | >50 uM |
| 55-DHEJ-31C | >50 uM |
| 55-DHEJ-37C | >50 uM |

TABLE 3

96 Hr MTS dose response experiments in H82 (small lung cell carcinoma) cells

| Compound | $IC_{50}$ |
|---|---|
| ZQW-36 | 1-10 uM |
| ZQW-35 | <1 uM |
| ZQW-35c | 1-10 uM |
| 39-TDW-11 | >26 uM |
| 39-TDW-3 | .53-2.7 uM |
| 39-TDW-10 | 5-10 uM |
| 39-TDW-12c | 10-50 uM |
| 39-TDW-12 | >50 uM |
| 39-TDW-20c | 2.76-5.52 uM |
| 39-TDW-47c | 1-5 uM |
| 40-TDW-19 | 5-10 uM |
| 40-TDW-23 | 10-50 uM |
| 40-TDW-31c | 1-5 uM |
| 40-TDW-29c | 10-50 uM |
| 40-TDW-30 | 1-5 uM |
| 49-TDW-15 | 10-50 uM |
| 49-TDW-17C | 10-50 uM |

TABLE 4

96 Hr MTS dose response experiments in A549 cells.

| Compound | $IC_{50}$ |
|---|---|
| 39-TDW-11 | >10 uM |
| 39-TDW-3 | 1-10 uM |
| 39-TDW-10 | >10 uM |
| 39-TDW-12c | >10 uM |
| 39-TDW-12 | >10 uM |
| 39-TDW-20c | >10 uM |
| 46-TDW-34C | 1-5 uM |

TABLE 5

SSAT (spermidine/spermine-$N^1$-acetyltransferase) activity in H157 (non-small cell lung carcinoma) cells.

| Compound | Conc. | Fold induction | Exposure Time |
|---|---|---|---|
| UNS-31-11C, MLB-19-21 | 10 uM | 33.3 | 12 hr |
| MLB-19-30 | 10 uM | slight induction | 12 hr |
| FHB-24-14 | 10 uM | 75 | 12 hr |
| BENSpm | 10 uM | 1300 | 24 hr |
| FHB-26-26 | 10 uM | 22.5 | 24 hr |
| azaCHENSpd | 1 uM | 250 | 24 hr |
| ZQW-27-11C | 10 uM | no induc | 24 hr |
| ZQW-27-9 | 10 uM | no induc | 24 hr |
| MLB-19-30 | 10 uM | 1406 | 24 hr |
| ZQW-14c | 10 uM | no induc | 24 hr |
| ZQW-16c | 10 uM | no induc | 24 hr |
| ZQW-19 | 10 uM | 30 | 24 hr |
| UNS-30-42B | 10 uM | no induc | 24 hr |
| UNS-31-1c | 10 uM | no induc | 24 hr |
| UNS-31-7A | 10 uM | no induc | 24 hr |
| UNS-31-10c | 10 uM | no induc | 24 hr |
| UNS-31-18 | 10 uM | 15 | 24 hr |
| UNS-31-19c | 10 uM | no induc | 24 hr |
| CPCHENSpm | 10 uM | no induc | 24 hr |
| UNS-31-21c | 10 uM | 5.7 | 24 hr |
| BEPPSpd | 10 uM | 929 | 24 hr |
| alpha-methyl CHENspm | 10 uM | no induc | 24 hr |
| ZQW-36 | 10 uM | no induc | 24 hr |
| ZQW-35 | 4 uM | no induc | 24 hr |
| ZQW-35c | 10 uM | no induc | 24 hr |
| ZQW-44 | 10 uM | 45 | 24 hr |
| ZQW-46 | 10 uM | 21,500 | 24 hr |
| ZQW-35-7c | 10 uM | 105 | 24 hr |
| ZQW-35-8 | 10 uM | no induc | 24 hr |
| ZQW-35-8c | 10 uM | 217 | 24 hr |
| 39-TDW-11 | 10 uM | no induc | 24 hr |
| 39-TDW-10 | 10 uM | no induc | 24 hr |
| 39-TDW-12c | 10 uM | 189 | 24 hr |
| 39-TDW-12 | 10 uM | no induc | 24 hr |
| 39-TDW-20c | 10 uM | no induc | 24 hr |
| 40-TDW-1 | 10 uM | no induc | 24 hr |
| 39-TDW-47c | 10 uM | no induc | 24 hr |
| 39-TDW-43 | 10 uM | no induc | 24 hr |
| 40-TDW-19 | 10 uM | no induc | 24 hr |
| 40-TDW-26c | 10 uM | no induc | 24 hr |
| 40-TDW-23 | 10 uM | no induc | 24 hr |
| 40-TDW-31c | 10 uM | 966 | 24 hr |
| 40-TDW-29c | 10 uM | no induc | 24 hr |
| 40-TDW-30 | 10 uM | 136 | 24 hr |
| 40-TDW-28 | 10 uM | no induc | 24 hr |
| 42-TDW-4c | 10 uM | 36 | 24 hr |
| 42-TDW-12 | 10 uM | no induc | 24 hr |
| 42-TDW-14 | 10 uM | no induc | 24 hr |
| 42-TDW-20c | 10 uM | no induc | 24 hr |
| 42-TDW-21c | 10 uM | no induc | 24 hr |
| 42-TDW-35c | 10 uM | no induc | 24 hr |
| 42-TDW-43 | 10 uM | 15 | 24 hr |
| 42-TDW-40c | 10 uM | no induc | 24 hr |
| 42-TDW-40 | 10 uM | no induc | 24 hr |
| 42-TDW-38 | 10 uM | no induc | 24 hr |
| 46-TDW-34C | 10 uM | 671 | 24 hr |
| 53-SV-3C | 5 uM | 327 | 24 hr |
|  | 10 uM |  |  |
| YZ3604C | 5 uM | 454 | 24 hr |
|  | 10 uM |  |  |
| 53-SV-2C | 10 uM | 3 | 24 hr |

TABLE 6

Polyamine levels in H157 (non-small cell lung carcinoma) cells following treatment.

| Compound | Treatment Conc. | Level | Exposure time |
|---|---|---|---|
| FHB-24-11 | 10 uM | slight inc | 24 hr |
| Et-3-3-3-OH | 10 uM | slight dec | 24 hr |
| RHW-50-53 | 10 uM | N/C | 24 hr |

TABLE 6-continued

Polyamine levels in H157 (non-small cell lung carcinoma) cells following treatment.

| Compound | Treatment Conc. | Level | Exposure time |
|---|---|---|---|
| RHW-69-68C | 10 uM | slight dec | 24 hr |
| BENSpm | 10 uM | N/C | 24 hr |
| FHB-26-26 | 10 uM | very slight dec | 24 hr |
| azaCHENSpd | 1 uM | very slight inc. | 24 hr |
| ZQW-27-11C | 10 uM | N/C | 96 hr |
| ZQW-27-9 | 10 uM | N/C | 24 hr |
| ZQW-14c | 10 uM | slowly dec | 24 hr |
| ZQW-16c | 10 uM | slowly inc | 24 hr |
| ZQW-19 | 1 uM | N/C | 24 hr |
|  | 10 uM | dec ~50% |  |
| UNS-30-42B | 10 uM | slightly dec | 24 hr |
| UNS-31-1c | 10 uM | N/C | 24 hr |
| UNS-31-7A | 10 uM | slight dec | 24 hr |
| UNS-31-10c | 10 uM | slight inc | 24 hr |
| UNS-31-18 | 10 uM | N/C | 24 hr |
| UNS-31-19c | 10 uM | N/C | 24 hr |
|  | 10 uM | inc ~50% |  |
| CPCHENSpm | 10 uM | slight dec | 24 hr |
|  | Spm | inc |  |
| UNS-31-21c | 10 uM | dec | 24 hr |
|  | Spm | same |  |
| alpha-methyl CHENspm | 5 uM | N/C | 24 hr |
|  | 10 uM | N/C |  |
| ZQW-36 | 10 uM | slight dec | 24 hr |
|  | spm | inc |  |
| ZQW-35 | 4 uM | N/C | 24 hr |
| ZQW-44 | 10 uM | N/C | 24 hr |
| ZQW-46 | 10 uM | N/C | 24 hr |
| ZQW-35-7c | 5 uM | slight dec | 24 hr |
|  | 10 uM | dec |  |
| ZQW-35-8 | 10 uM | N/C | 24 hr |
| ZQW-35-8c | 10 uM | dec | 24 hr |
|  | spd, spm | 1 g dec |  |
| 46-TDW-34C | 10 uM | dec ~6-10 fold | 24 hr |

TABLE 7

SMO (Spermine Oxidase) activity in H157 (non-small cell lung carcinoma) cells

| Compound | Treatment Conc. | Cntrl (pmol/mgP/min) | Activity (pmol/mgP/min) | Exposure Time |
|---|---|---|---|---|
| 46-TDW-34C | 10 uM | 22.77 | 68.24 | 24 hr |

TABLE 8

Drug induced cell cycle measurements in H157 (non-small cell lung carcinoma) cells.

| 53-SV-3C | FACS 24 hr 10 uM: Ctrl: G1 = 30.50%, S = 16.55%, G2 = 27.06% 10 uM: G1 = 14.92%, S = 17.39%, G2 = 40.87% |
| YZ3604C | FACS 24 hr 10 uM: Ctrl: G1 = 30.50%, S = 16.55%, G2 = 27.06% 10 uM: G1 = 14.70%, S = 14.55%, G2 = 33.70% |
| 53-SV-2C | FACS 24 hr 10 uM: Ctrl: G1 = 30.50%, S = 16.55%, G2 = 27.06% 10 uM: G1 = 32.25%, S = 10.72%, G2 = 25.05% |

TABLE 9

SSAT activity in H82 (Small Cell Lung Carcinoma) cells

| Compound | Treatment Conc. | Activity | Exposure Time |
|---|---|---|---|
| BENSpm | 10 uM | no induc | 72 hr |
| FHB-26-26 | 10 uM | no induc | 24 hr |
| azaCHENSpd | 10 uM | no induc | 24 hr |
| ZQW-27-11C | 10 uM | no induc | 24 hr |
| ZQW-27-9 | 10 uM | no induc | 24 hr |
| MLB-19-30 | 10 uM | slight dec | 24 hr |
| ZQW-14c | 10 uM | no induc | 24 hr |
| ZQW-16c | 10 uM | no induc | 24 hr |
| ZQW-19 | 10 uM | no induc | 24 hr |
| UNS-30-42B | 10 uM | no induc | 24 hr |
| UNS-31-1c | 10 uM | no induc | 24 hr |
| UNS-31-7A | 10 uM | no induc | 24 hr |
| UNS-31-10c | 10 uM | no induc | 24 hr |
| UNS-31-18 | 10 uM | no induc | 24 hr |
| UNS-31-19c | 10 uM | no induc | 24 hr |
| CPCHENSpm | 10 uM | no induc | 24 hr |
| UNS-31-21c | 10 uM | no induc | 24 hr |
| alpha-methyl CHENspm | 10 uM | no induc | 24 hr |
| ZQW-44 | 10 uM | no induc | 24 hr |
| ZQW-46 | 10 uM | no induc | 24 hr |
| ZQW-35-7c | 10 uM | no induc | 24 hr |
| ZQW-35-8 | 10 uM | no induc | 24 hr |
| ZQW-35-8c | 10 uM | no induc | 24 hr |

TABLE 10

ODC (Ornithine decarboxylase) activity in H82 (Small Cell Lung Carcinoma) cells.

| Compound | Treatment Conc. | Ctrl (pmol/mgP/hr) | Activity (pmol/mgP/hr) | Exposure Time |
|---|---|---|---|---|
| 39-TDW-11 | 10 uM | 667 | 520 | 24 hr |
| 39-TDW-3 | 10 uM | 667 | 3720 | 24 hr |
| 39-TDW-10 | 10 uM | 869 | 541 | 24 hr |
| 39-TDW-12c | 10 uM | 831 | 584 | 24 hr |
| 39-TDW-12 | 10 uM | 831 | 755 | 24 hr |
| 39-TDW-20c | 10 uM | 869 | 393 | 24 hr |
| 40-TDW-1 | 10 uM | 1462 | 1385 | 24 hr |
| 39-TDW-47c | 10 uM | 1462 | 1955 | 24 hr |
| 40-TDW-19 | 10 uM | 667 | 528 | 24 hr |
| 40-TDW-23 | 10 uM | 869 | 707 | 24 hr |
| 40-TDW-29c | 10 uM | 831 | 903 | 24 hr |
| 42-TDW-4 | 10 uM | 667 | 44 | 24 hr |
| 42-TDW-4c | 10 uM | 1462 | 1671 | 24 hr |
| 42-TDW-12 | 10 uM | 667 | 650 | 24 hr |
| 42-TDW-14 | 10 uM | 869 | 530 | 24 hr |
| 44-DHEJ-4c | 10 uM | 1462 | 1426 | 24 hr |
| 44-DHEJ-8c | 10 uM | 1462 | 949 | 24 hr |
| 44-DHEJ-7c | 10 uM | 1462 | 348 | 24 hr |
| 44-DHEJ-9 | 10 uM | 1462 | 1353 | 24 hr |
| 44-DHEJ-12c | 10 uM | 1462 | 1784 | 24 hr |
| 42-TDW-40c | 10 uM | 869 | 426 | 24 hr |
| 42-TDW-38 | 10 uM | 864 | 576 | 24 hr |

TABLE 11

Polyamine levels in H82 cells following treatment.

| Compound | Treatment Conc. | Level | Exposure Time |
|---|---|---|---|
| FHB-26-26 | 10 uM | slight dec | 24 hr |
| azaCHENSpd | 10 uM | N/C | 24 hr |
| ZQW-27-11C | 10 uM | dec ~50% | 24 hr |
| ZQW-27-9 | 10 uM | dec | 24 hr |
| ZQW-14c | 10 uM | slowly dec | 24 hr |
| ZQW-16c | 0-10 uM | slight inc | 24 hr |
|  | 10 uM | dec ~50% |  |

TABLE 11-continued

Polyamine levels in H82 cells following treatment.

| Compound | Treatment Conc. | Level | Exposure Time |
|---|---|---|---|
| ZQW-19 | 0-10 uM | slow dec | 24 hr |
|  | 10 uM | dec ~50% |  |
| UNS-30-42B | 10 uM | slight inc | 24 hr |
| UNS-31-1c | 10 uM | N/C | 24 hr |
| UNS-31-7A | 10 uM | slight dec | 24 hr |
| UNS-31-10c | 10 uM | slight dec | 24 hr |
| UNS-31-18 | 10 uM | N/C | 24 hr |
| UNS-31-19c | 10 uM | slight dec | 24 hr |
| CPCHENSpm | 10 uM | slight inc, N/C | 24 hr |
| UNS-31-21c | 10 uM | slight inc | 24 hr |
| alpha-methyl CHENspm | 10 uM | slight inc | 24 hr |
| ZQW-44 | 50 uM | inc | 24 hr |
| ZQW-46 | 5-uM | dec | 24 hr |
| ZQW-35-7c | 10 uM | N/C | 24 hr |
| ZQW-35-8 | 10 uM | N/C, slight inc | 24 hr |
| ZQW-35-8c | 10 uM | N/C, slight inc | 24 hr |

TABLE 12

SSAT activity in A549 cells.

| Compound | Treatment Conc. | Ctrl (pmol/mgP/min) | Activity (pmol/mgP/min) | Exposure Time |
|---|---|---|---|---|
| 46-TDW-34C | 10 uM | 3.73 | 10435.87 | 24 hr |

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound having the formula (I):

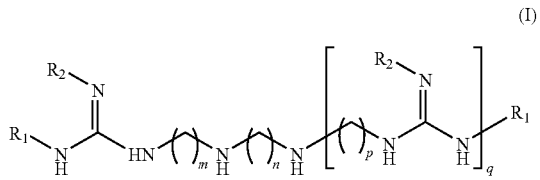

or a salt thereof, wherein:
n is an integer from 1 to 12;
m and p are independently an integer from 1 to 5;
q is 0 or 1;
each $R_1$ is independently selected from the group consisting of;
$C_1$-$C_8$ substituted or unsubstituted alkyl, $C_4$-$C_{15}$ substituted or unsubstituted cycloalkyl, $C_3$-$C_{15}$ substituted or unsubstituted branched alkyl, $C_6$-$C_{20}$ substituted or unsubstituted aryl, $C_6$-$C_{20}$ substituted or unsubstituted heteroaryl, $C_7$-$C_{24}$ substituted or unsubstituted aralkyl, and $C_7$-$C_{24}$ substituted or unsubstituted heteroaralkyl and,
each $R_2$ is independently selected from hydrogen or a $C_1$-$C_8$ substituted or unsubstituted alkyl.

2. The compound of claim 1, wherein the compound is a compound listed in Table A.

3. A pharmaceutical composition comprising the compound of claim 1 and a pharmaceutically acceptable carrier.

4. A kit comprising the compound of claim 1 and instructions for use as an anticancer or antiparasitic agent.

5. A method of inhibiting a histone demethylase, comprising administering an amount of a compound of claim 1, wherein the amount of the compound is sufficient to inhibit the histone demethylase by at least about 50%.

6. A method of treating a parasitic infection, comprising administering a compound of claim 1 in a therapeutically effective amount.

7. The method of claim 5, wherein the enzyme is lysine-specific demethylase-1.

8. A compound of claim 1, wherein the compound is

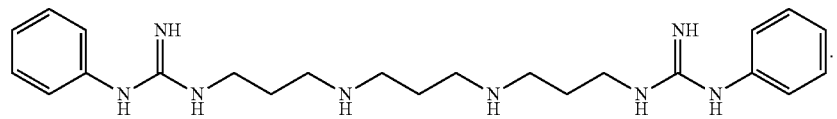

9. A pharmaceutical composition of claim 3 wherein the compound is

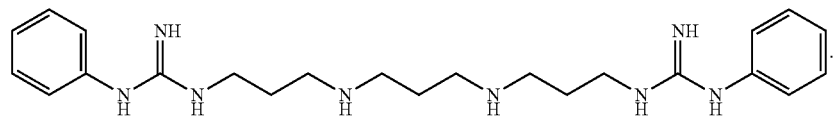

10. A kit of claim 4 wherein the compound is
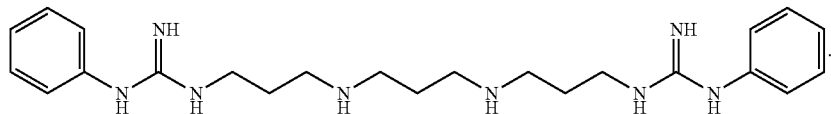
11. A method of claim 5 wherein the compound is:
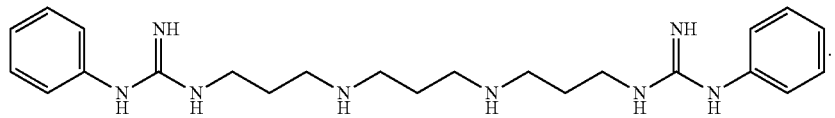
12. A method of claim 6 wherein the compound is:
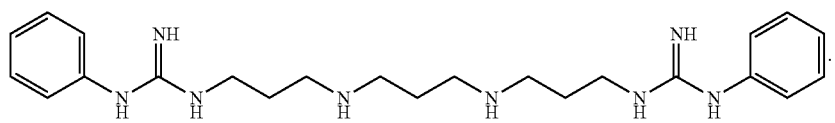
* * * * *